US007678886B2

(12) United States Patent
Zalevsky et al.

(10) Patent No.: US 7,678,886 B2
(45) **Date of Patent: *Mar. 16, 2010**

(54) PHARMACEUTICAL COMPOSITIONS OF ADIPONECTIN VARIANTS AND METHODS OF STORAGE

(75) Inventors: Jonathan Zalevsky, Riverside, CA (US); Duc-Hanh Thi Nguyen, Sylmar, CA (US); Gregory L. Moore, Monrovia, CA (US); Sergei A. Ezhevsky, San Diego, CA (US); John R. Desjarlais, Pasadena, CA (US); Arthur J. Chirino, Camarillo, CA (US); Darian Cash, Los Angeles, CA (US); Matthew J. Bernett, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/421,061

(22) Filed: May 30, 2006

(65) Prior Publication Data

US 2006/0276395 A1 Dec. 7, 2006

Related U.S. Application Data

(63) Continuation-in-part of application No. 11/328,901, filed on Jan. 9, 2006.

(60) Provisional application No. 60/642,476, filed on Jan. 7, 2005, provisional application No. 60/650,411, filed on Feb. 3, 2005, provisional application No. 60/698,358, filed on Jul. 11, 2005, provisional application No. 60/720,768, filed on Sep. 26, 2005, provisional application No. 60/733,137, filed on Oct. 2, 2005, provisional application No. 60/790,220, filed on Apr. 7, 2006, provisional application No. 60/781,509, filed on Mar. 9, 2006, provisional application No. 60/777,825, filed on Mar. 1, 2006.

(51) Int. Cl.

| | |
|---|---|
| ***C07K 14/00*** | (2006.01) |
| ***C07K 1/00*** | (2006.01) |
| ***C07K 17/00*** | (2006.01) |
| ***C07K 16/00*** | (2006.01) |
| ***A61K 38/24*** | (2006.01) |
| ***A61K 38/27*** | (2006.01) |

(52) U.S. Cl. ....................... 530/350; 530/395; 530/397; 530/399

(58) Field of Classification Search ....................... None
See application file for complete search history.

(56) References Cited

U.S. PATENT DOCUMENTS

| | | | |
|---|---|---|---|
| 5,869,330 | A | 2/1999 | Scherer et al. |
| 6,344,441 | B1 | 2/2002 | Bihain et al. |
| 6,461,821 | B1 | 10/2002 | Matsuzawa et al. |
| 6,566,332 | B2 | 5/2003 | Fruebis et al. |
| 6,579,852 | B2 | 6/2003 | Fruebis et al. |
| 6,716,965 | B2 | 4/2004 | Fox et al. |
| 6,946,444 | B2 | 9/2005 | Bihain et al. |
| 6,967,091 | B2 | 11/2005 | Fruebis et al. |
| 2002/0132773 | A1 | 9/2002 | Kincade et al. |
| 2003/0166551 | A1 | 9/2003 | Matsuzawa et al. |
| 2003/0176328 | A1 | 9/2003 | Rasmussen et al. |
| 2004/0023854 | A1 | 2/2004 | Cooper et al. |
| 2004/0067881 | A1 | 4/2004 | Fruebis et al. |
| 2004/0180818 | A1 | 9/2004 | Matsuzawa et al. |
| 2004/0241802 | A1 | 12/2004 | Kadowaki et al. |
| 2006/0052292 | A1 | 3/2006 | Rasmussen et al. |

FOREIGN PATENT DOCUMENTS

| | | |
|---|---|---|
| WO | 03/055918 | 7/2003 |
| WO | 2004/063711 | 7/2004 |
| WO | WO 2005/113599 A1 | 12/2005 |

OTHER PUBLICATIONS

Witkowski et al., Biochemistry, 38, 11643-11650, 1999.*

Wishart et al., Journal of Biological Chemistry, vol. 270, No. 45, pp. 26782-26785, 1995.*

Kisselev, Structure, vol. 10, pp. 8-9, 2002.*

Ngo et al,. in The Protein Folding Problem and Tertiary Structure Prediction, 1994, Merz et al. (ed.), Birkhauser, Boston, MA, pp. 433 and 492-495.*

Golovanov et al., A Simple Method for Improving Protein Solubility and Long-Term Stability, J. Am. Chem. Soc., vol. 126, No. 29, 2004, published on Jul. 1, 2004.*

Dahiyat et al., De Novo Protein Design: Fully Automated Sequence Selection, 1997, Science 278: 82-7.*

Retrieved from the Internet <URL:http://www.peprotech.com/product.
asp?product%5Fid=450%2D24%28PeproTech+Base+Catalog%29
&category%5Fname=Display%28PeproTech+Base+Catalog%29
&search=450-24&cookie%5Ftest=1>.*

(Continued)

*Primary Examiner*—Nashaat T Nashed
*Assistant Examiner*—Jae W Lee
(74) *Attorney, Agent, or Firm*—Morgan Lewis & Bockius LLP; Robin M. Silva, Esq.; David C. Foster, Esq.

(57) ABSTRACT

A composition comprising an adiponectin variant at a concentration of at least 2.0 mg/mL, and a pharmaceutically acceptable carrier, wherein less than 20% of said adiponectin variant would aggregate after storage at 4° C. for one week in 10 mM $PO_4$, 150 mM NaCl buffer.

8 Claims, 50 Drawing Sheets

OTHER PUBLICATIONS

Takashi Kadowaki, et al, "Adiponectin and Adiponectin Receptors" Endocrine Reviews 26(3):439-451, 2005.
K. Staiger, et al., "Adiponectin is functionally active in human islets but does not affect insulin secretory function or beta-cell lipoapoptosis" Journal of Clinical Endocrinology & Metabolism. First published Oct. 4, 2005 as doi:10.1210/jc.2005-0467.
Tsatsanis, et al., "Adiponectin induces TNF-*a* and IL-6 in macrophages and promotes tolerance to itself and other pro-inflammatory stimuli", Biochemical and Biophysical Research Communications 335 (2005) 1254-1263.
I. Rakatzi, et al., "Adiponectin counteracts cytokine- and fatty acid-induced apoptosis in the pancreatic beta-cell line INS-1" Diabetologia (2004) 47:249-258.
Moller, et al., "Metabolic Syndrome: A Clinical and Molecular Perspective", Annu. Rev. Med. 2005. 56:45-62.
Bråkenhielm, et al., "Adiponectin-induced antiangiogenesis and antitumor activity involve caspase-mediated endothelial cell apoptosis", 2476-2481, PNAS, Feb. 24, 2004 , vol. 101, No. 8.
Hida, et al., "Visceral adipose tissue-derived serine protease inhibitor: A unique insulin-sensitizing adipocytokine in obesity", 10610-10615, PNAS, Jul. 26, 2005, vol. 102, No. 30.
Waki, et al., "Impaired Multimerization of Human Adiponectin Mutants Associated with Diabetes : Molecular Structure and Multimer Formation of Adiponectin", The Journal of Biological Chemistry vol. 278, No. 41, Issue of Oct. 10, pp. 40352-40363, 2003.
Wang, et al., "Hydroxylation and Glycosylation of the Four Conserved Lysine Residues in the Collagenous Domain of Adiponectin : Potential Role in the Modulation of Its Insulin-Sensitizing Activity", The Journal of Biological Chemistry vol. 277, No. 22, Issue of May 31, pp. 19521-19529, 2002.
Wang, et al., "Adiponectin Inhibits Cell Proliferation by Interacting with Several Growth Factors in an Oligomerization-dependent Manner", The Journal of Biological Chemistry vol. 280, No. 18, Issue of May 6, pp. 18341-18347, 2005.
Wong, et al., "A family of Acrp30_adiponectin structural and functional paralogs" , 10302-10307, PNAS, Jul. 13, 2004, vol. 101, No. 28.
Wu, et al., "Involvement of AMP-Activated Protein Kinase in Glucose Uptake Stimulated by the Globular Domain of Adiponectin in Primary Rat Adipocytes", Diabetes, vol. 52, Jun. 2003, 1355-1363.
Xu, et al., "Streptococcal Scl1 and Scl2 Proteins Form Collagen-like Triple Helices", The Journal of Biological Chemistry vol. 277, No. 30, Issue of Jul. 26, pp. 27312-27318, 2002.
Yamauchi, et al., "Globular Adiponectin Protected ob/ob Mice from Diabetes and ApoE-deficient Mice from Atherosclerosis", The Journal of Biological Chemistry vol. 278, No. 4, Issue of Jan. 24, pp. 2461-2468, 2003.
Yamauchi, et al., "Cloning of adiponectin receptors that mediate antidiabetic metabolic effects", Nature | vol. 423 | Jun. 12, 2003 |www.nature.com/nature.
Yamauchi, et al., "The fat-derived hormone adiponectin reverses insulin resistance associated with both lipoatrophy and obesity", 2001 Nature Publishing Group http://medicine.nature.com, Nature Medicine • vol. 7 • No. 8 • Aug. 2001, 941-946.
Shimada, et al. "Adiponectin and atherosclerotic disease", Clinica Chimica Acta 344 (2004) 1-12.
Tomas, et al., "Enhanced muscle fat oxidation and glucose transport by ACRP30 globular domain: Acetyl—CoA carboxylase inhibition and AMP-activated protein kinase activation", PNAS_Dec. 10, 2002_vol. 99_No. 25_16309-16313.
Tsao, et al., "ACRP30, a new hormone controlling fat and glucose metabolism", European Journal of Pharmacology 440 (2002) 213-221.
Tsao, et al., "Role of Disulfide Bonds in Acrp30/Adiponectin Structure and Signaling Specificity Different Oligomers Activate Different Signal Transduction Pathways", The Journal of Biological Chemistry vol. 278, No. 50, Issue of Dec. 12, pp. 50810-50817, 2003.
Tsao, et al., "Oligomerization State-dependent Activation of NF-_B Signaling Pathway by Adipocyte Complement-related Protein of 30 kDa (Acrp30)", The Journal of Biological Chemistry vol. 277, No. 33, Issue of Aug. 16, pp. 29359-29362, 2002.
Ukkola, et al., "Mutations in the Adiponectin Gene in Lean and Obese Subjects From the Swedish Obese Subjects Cohort", *Metabolism*, vol. 52, No. 7 Jul. 2003: pp. 881-884.
Arita, et al., "Paradoxical Decrease of an Adipose-Specific Protein, Adiponectin, in Obesity", Biochemical and Biophysical Research Communications 257, 1999, pp. 79-83.
Berg, et al., "ACRP30/adiponectin: an adipokine regulating glucose and lipid metabolism", TRENDS in Endocrinology & Metabolism, vol. 13, No. 2, Mar. 2002, pp. 84-89.
Hu, et al., "AdipoQ Is a Novel Adipose-specific Gene Dysregulated in Obesity*", The Journal of Biological Chemistry, vol. 271, No. 18, May 3, 1996, pp. 10697-10703.
Maeda, et al., cDNA Cloning and Expression of a Novel Adipose Specific Collagen-like Factor, apM1 (Adipose Most Abundant Gene Transcript 1), Biochemical and Biophysical Research Communications, vol. 221, 1996, pp. 286-289.
Qi, et al., "Adiponectin acts in the brain to decrease body weight," Nature Medicine, vol. 10, No. 5, May 2004, 524-529.
Ryo et al., "Adiponectin as a Biomarker of the Metabolic Syndrome," Circulation Journal, vol. 68, Nov. 2004, pp. 975-981.
Scherer, et al., "A Novel Serum Protein Similar to C1q, Produced Exclusively in Adipocytes," The Journal of Biological Chemistry, vol. 270, No. 45, Nov. 10, 1995, pp. 26746-26749.
Shapiro, et al., "The crystal structure of a complement-1q family protein suggests an evolutionary link to tumor necrosis factor," Current Biology, vol. 8, No. 6, 1998, pp. 335-338.
Shibata, et al., "Adiponectin-mediated modulation of hypertrophic signals in the heart," Nature Medicine, vol. 10, No. 12, Dec. 2004, pp. 1384-1389.
Shibata, et al., Adiponectin protects against myocardial ischemia-reperfusion injury through AMPK- and COX-2-dependent mechanisms, Nature Medicine, vol. 11, No. 10, Oct. 2005, pp. 1096-1103.
Sullivan, et al., "Characerisation of 5'-Amp-Activated Protein Kinase in Human Liver Using Specific Peptide Substrates and the Effects of 5'-Amp Analogues on Enzyme Activity," Biochemical and Biophysical Research Communications, vol. 200, No. 3, May 16, 1994, pp. 1551-1556.
Violand, Bernard, "Generation of Novel Protein Therapeutics," Pfizer, IBC's Next Generation Protein Therapeutics (NGPT) meeting held Nov. 8-9, 2005 in Basel, Switzerland, 33 pages.
Weekes, et al., "Specificity determinants for the AMP-activated protein kinase and its plant homologue analysed using synthetic peptides," Federation of European Biochemical Societies, vol. 334, No. 3, Nov. 1993, pp. 335-339.
Witters, et al., "Insulin Activation of Acetyl-CoA Carboxylase Accompanied by Inhibition of the 5'-AMP-activated Protein Kinase," The Journal of Biological Chemistry, vol. 267, No. 5, Feb. 15, 1992, pp. 2864-2867.
Yamauchi, et al., "Adiponectin stimulates glucose utilization and fatty-acid oxidation by activating AMP-activated protein kinase", Nature Medicine • vol. 8 • No. 11 • Nov. 2002, 1288-1295.
Yokota, et al., "Adiponectin, a new member of the family of soluble defense collagens, negatively regulates the growth of myelomonocytic progenitors and the functions of macrophages", Blood, Sep. 1, 2000 z vol. 96, No. 5, 1723-1732.
Berg, et al., "The adipocyte-secreted protein Acrp30 enhances hepatic insulin action", Nature Medicine • vol. 7 • No. 8 • Aug. 2001, 947-953.
Boutin, et al., "GAD2 on Chromosome 10p12 Is a Candidate Gene for Human Obesity", PLoS Biology | http://biology.plosjournals.org, vol. 1 | Issue 3, 1-11, 2003.
Cancello, et al., "Adiposity signals, genetic and body weight regulation in humans", Diabetes Metab 2004,30,215-27.
Pineiro, et al., "Adiponectin is synthesized and secreted by human and murine cardiomyocytes", FEBS Letters 579 (2005) 5163-5169.
Ceddia, et al., "Globular adiponectin increases GLUT4 translocation and glucose uptake but reduces glycogen synthesis in rat skeletal muscle Cells", Diabetologia (2005) 48: 132-139.
Chen, et al., "Impaired Activation of AMP-Kinase and Fatty Acid Oxidation by Globular Adiponectin in Cultured Human Skeletal Muscle of Obese Type 2 Diabetics", The Journal of Clinical Endocrinology & Metabolism 90(6):3665-3672, 2005.

Chinetti, et al., Expression of adiponectin receptors in human macrophages and regulation by agonists of the nuclear receptors PPARa, PPARc, and LXR, Biochemical and Biophysical Research Communications 314 (2004) 151-158.

Combs, et al., "Endogenous glucose production is inhibited by the adipose-derived protein Acrp30", The Journal of Clinical Investigation | Dec. 2001 | vol. 108 | No. 12, 1875-1881.

Di'ez, et al., "The role of the novel adipocyte-derived hormone adiponectin in human disease", European Journal of Endocrinology (2003) 148 293-300.

Waki, et al., "Generation of Globular Fragment of Adiponectin by Leukocyte Elastase Secreted by Monocytic Cell Line THP-1", Endocrinology 146(2):790-796, 2005.

Fruebis, et al., "Proteolytic cleavage product of 30-kDa adipocyte complement-related protein increases fatty acid oxidation in muscle and causes weight loss in mice", PNAS, Feb. 13, 2001, vol. 98, No. 4, 2005-2010.

Gil-Campos, et al., "Adiponectin, the missing link in insulin resistance and obesity", www.elsevier.com/locate/clnu, Clinical Nutrition (2004) 23, 963-974.

Goldstein, et al., "Adiponectin: A Novel Adipokine Linking Adipocytes and Vascular Function", The Journal of Clinical Endocrinology & Metabolism 89(6):2563-2568, 2004.

D Grahame Hardie, "New roles for the LKB1!AMPK pathway", www.sciencedirect.com Current Opinion in Cell Biology 2005, 17:167-173.

Hardie, et al., "Management of cellular energy by the AMP-activated protein kinase system", FEBS Letters 546 (2003) 113-120.

Kobayashi, et al., "Selective Suppression of Endothelial Cell Apoptosis by the High Molecular Weight Form of Adiponectin", http://circres.ahajournals.org/cgi/content/full/94/4/e27 ; Downloaded from circres.ahajournals.org by on Oct. 18, 2005.

Hotta, et al., "Circulating Concentrations of the Adipocyte Protein Adiponectin Are Decreased in Parallel With Reduced Insulin Sensitivity During the Progression to Type 2 Diabetes in Rhesus Monkeys", Diabetes, vol. 50, May 2001, 1126-1133.

Hug, et al., "T-cadherin is a receptor for hexameric and high-molecular-weight forms of Acrp30_adiponectin", 10308-10313, PNAS Jul. 13, 2004 vol. 101 No. 28 www.pnas.org_cgi_doi_10.1073_pnas.0403382101.

Hug, et al., "The role of the adipocyte hormone adiponectin in cardiovascular disease", www.sciencedirect.com Current Opinion in Pharmacology 2005, 5:129-134.

Huypens, et al., "Adiponectin-mediated stimulation of AMP-activated protein kinase (AMPK) in pancreatic beta cells", www.elsevier.com/locate/lifescie; Life Sciences 77 (2005) 1273-1282.

Wilkes et al., "Topiramate Treatment Causes Skeletal Muscle Insulin Sensitization And Increased Acrp30 Secretion in High-Fat-Fed Male Wistar Rats", Articles in PresS. Am J Physiol Endocrinol Metab (Jul. 19, 2005).

Wilkes, et al., "Topiramate is an insulin-sensitizing compound in vivo with direct effects on adipocytes in female ZDF rats", *AJP—Endo* 288:617-624, 2005. First published Nov. 9, 2004.

Juge-Aubry, et al., "Adipose tissue: a regulator of inflammation", Best Practice & Research Clinical Endocrinology & Metabolism vol. 19, No. 4, pp. 547-566, 2005.

Kahn, et al., "Obesity and insulin resistance", The Journal of Clinical Investigation | Aug. 2000 | vol. 106 | No. 4, 473-481.

Kahn, et al., "AMP-activated protein kinase: Ancient energy Review gauge provides clues to modern understanding of metabolism", Cell Metabolism : Jan. 2005 • vol. 1 • 15-25.

Kishida, et al., "Disturbed secretion of mutant adiponectin associated with the metabolic syndrome", Biochemical and Biophysical Research Communications 306 (2003) 286-292.

Kobayashi, et al., "Selective Suppression of Endothelial Cell Apoptosis by the High Molecular Weight Form of Adiponectin", *Circulation Research* is available at http://www.circresaha.org ; DOI: 10.1161/01.RES.0000119921.86460.37, 2004.

Koerner, et al., "Adipocytokines: leptin—the classical, resistin—the controversical, adiponectin—the promising, and more to come", Best Practice & Research Clinical Endocrinology & Metabolism vol. 19, No. 4, pp. 525-546, 2005.

Kondo, et al., "Association of Adiponectin Mutation With Type 2 Diabetes A Candidate Gene for the Insulin Resistance Syndrome", Diabetes, vol. 51, Jul. 2002, 2325-2328.

Kubota, et al., "Disruption of Adiponectin Causes Insulin Resistance and Neointimal Formation", The Journal of Biological Chemistry vol. 277, No. 29, Issue of Jul. 19, pp. 25863-25866, 2002.

Kumada, et al., "Adiponectin Specifically Increased Tissue Inhibitor of Metalloproteinase-1 Through Interleukin-10 Expression in Human Macrophages", *Circulation* is available at http://www.circulationaha.org DOI: 10.1161/01.CIR.0000127953.98131.ED, 2004.

Lebovitz, et al., "Treatment of insulin resistance in diabetes mellitus", European Journal of Pharmacology 490 (2004)135-146.

Tonelli, et al., "Mechanisms of Early Insulin-Sensitizing Effects of Thiazolidinediones in Type 2 Diabetes", Diabetes, vol. 53, Jun. 2004, 1621-1629.

Masaki, et al., "Adiponectin Protects LPS-Induced Liver Injury Through Modulation of TNF-_ in KK-Ay Obese Mice", Hepatology, Jul. 2004, 177-184.

Matsuda, et al., "Role of Adiponectin in Preventing Vascular Stenosis The Missing Link of Adipo-Vascular Axis", The Journal of Biological Chemistry vol. 277, No. 40, issue of Oct. 4, pp. 37487-37491, 2002.

Motoshima, et al., "Adiponectin suppresses proliferation and superoxide generation and enhances eNOS activity in endothelial cells treated with oxidized LDL", Biochemical and Biophysical Research Communications 315 (2004) 264-271.

Combs, et al., "A Transgenic Mouse with a Deletion in the Collagenous Domain of Adiponectin Displays Elevated Circulating Adiponectin and Improved Insulin Sensitivity", Endocrinology 145(1):367-383, 2004.

Nakano, et al., "Isolation and Characterization of GBP28, a Novel Gelatin-Binding Protein Purified from Human Plasma", J. Biochem. 120 803-812 (1996).

Nawrocki, et al., "The delicate balance between fat and muscle: adipokines in metabolic disease and musculoskeletal inflammation", www.sciencedirect.com Current Opinion in Pharmacology 2004, 4:281-289.

Pajvani, et al., "Complex Distribution, Not Absolute Amount of Adiponectin, Correlates with Thiazolidinedione-mediated Improvement in Insulin Sensitivity", The Journal of Biological Chemistry vol. 279, No. 13, Issue of Mar. 26, pp. 12152-12162, 2004.

Narasimhan, et al., "Osmotin Is a Homolog of Mammalian Adiponectin and Controls Apoptosis in Yeast through a Homolog of Mammalian Adiponectin Receptor", Molecular Cell, vol. 17, 171-180, Jan. 21, 2005.

Ouchi, et al., "Adiponectin Stimulates Angiogenesis by Promoting Cross-talk between AMP-activated Protein Kinase and Akt Signaling in Endothelial Cells", The Journal of Biological Chemistry vol. 279, No. 2, Issue of Jan. 9, pp. 1304-1309, 2004.

Ouchi, et al., "Adipocyte-Derived Plasma Protein, Adiponectin, Suppresses Lipid Accumulation and Class A Scavenger Receptor Expression in Human Monocyte-Derived Macrophages", *Circulation* is available at http://www.circulationaha.org; 1057-1063, 2002.

Pajvani, et al., "Structure-Function Studies of the Adipocyte-secreted Hormone Acrp30/Adiponectin Implications for Metabolic Regulation and Bioactivity", The Journal of Biological Chemistry vol. 278, No. 11, Issue of Mar. 14, pp. 9073-9085, 2003.

Vavvas, et al., "Contraction-induced Changes in Acetyl-CoA Carboxylase and 5*-AMP-activated Kinase in Skeletal Muscle", The Journal of Biological Chemistry vol. 272, No. 20, Issue of May 16, pp. 13255-13261, 1997.

Persikov, et al., "Prediction of Collagen Stability from Amino Acid Sequence", The Journal of Biological Chemistry vol. 280, No. 19, Issue of May 13, pp. 19343-19349, 2005.

Rasmussen, et al., "Genome-based Identification and Analysis of Collagen-related Structural Motifs in Bacterial and Viral Proteins", The Journal of Biological Chemistry vol. 278, No. 34, Issue of Aug. 22, pp. 32313-32316, 2003.

Ruan, et al., "Insulin resistance in adipose tissue: direct and indirect effects of tumor necrosis factor-α", Cytokine & Growth Factor Reviews 14 (2003) 447-455.

Ruderman, et al., "Minireview: Malonyl CoA, AMP-Activated Protein Kinase, and Adiposity", Endocrinology 144(12):5166-5171, 2003.

Satoh, et al., "Adenovirus-Mediated Adiponectin Expression Augments Skeletal Muscle Insulin Sensitivity in Male Wistar Rats", Diabetes, vol. 54, May 2005, 1304-1313.

Motoshima, et al., "Adiponectin suppresses proliferation and superoxide generation and enhances eNOS activity in endothelial cells treated with oxidized LDL", Biochemical and Biophysical Research Communications 315 (2004) 264-271.

Marshall, et al., "Rational Design and Engineering of Therapeutic Proteins," Drug Discovery Today, vol. 8, No. 5 (2003), pp. 212-221.

* cited by examiner

Figure 1 – (SEQ ID NO:1)

```
1    MLLLGAVLLL LALPGHDQET TTQGPGVLLP LPKGACTGWM AGIPGHPGHN 50
51   GAPGRDGRDG TPGEKGEKGD PGLIGPKGDI GETGVPGAEG PRGFPGIQGR 100
101  KGEPGEGAYV YRSAFSVGLE TYVTIPNMPI RFTKIFYNQQ NHYDGSTGKF 150
151  HCNIPGLYYF AYHITVYMKD VKVSLFKKDK AMLFTYDQYQ ENNVDQASGS 200
201  VLLHLEVGDQ VWLQVYGEGE RNGLYADNDN DSTFTGFLLY HDTN 244
```

Figure 2

```
human   MLLLGAVLLLLALPGHDQ---ETTTQGPGVLLPLPKGACTGWMAGIPGHP 47
macaque M-LLGAVLLLLALPSHGQ---DTTTQGPGVLLPLPKGACTGWMAGIPGHP 46
dog     MLLLRAVLLLLVLPAHGQ---DSVAEGPGVLLPLPKGACPGWMAGIPGHP 47
boar    MLLLGAVLLLLALPSLGQ---ETTEK-PGALLPMPKGACAGWMAGIPGHP 46
cow     MLLQGALLLLLALPSHGE---DNMEDP-----PLPKGACAGWMAGIPGHP 42
rat     MLLLQALLFLLILPSHEG--I-TATEGPGALVPPPKETCAGWMAGIPGYP 47
mouse   MLLLQALLFLLILPSHAEDDVTTTEELAPALVPPPKGTCAGWMAGIPGHS 50
chicken MRGSVGFLLCSLLLALSG-----TEMADQADQSDPKMSCANWMGGAPGHP 45

human   GHNGAPGRDGRDGTPGEKGEKGDPGLIGPKGDIGETGVPGAEGPRGFPGI 97
macaque GHNGVPGRDGRDGTPGEKGEKGDPGLIGPKGDTGETGVTGAEGPRGFPGI 96
dog     GHNGTPGRDGRDGTPGEKGEKGDAGLVGPKGDTGETGVTGVEGPRGFPGT 97
boar    GHNGTPGRDGRDGVPGEKGEKGDTGLTGPKGDTGESGVTGVEGPRGFPGI 96
cow     GHNGTPGRDGRDGTPGEKGEKGDAGLLGPKGETGDVGMTGAEGPRGFPGT 92
rat     GHNGIPGRDGRDGTPGEKGEKGDAGVLGPKGDPGDAGMTGAEGPRGFPGT 97
mouse   GHNGTPGRDGRDGTPGEKGEKGDAGLLGPKGETGDVGMTGAEGPRGFPGT 100
chicken GHNGLPGRDGKDGKDGQKGDKGEPGLQGVKGDTGEKGATGAEGPRGFPGH 95

human   QGRKGEPGEGAYVYRSAFSVGLETYVTIPNMPIRFTKIFYNQQNHYDGST 147
macaque QGRKGEPGEGAYVYRSAFSVGLETYVTVPNMPIRFTKIFYNQQNHYDGST 146
dog     PCRKGEPGESAYVHRSAFSVGLESRITVPNVPIRFTKIFYNLQNHYDGTT 147
boar    PGRKGEPGESAYVYRSAFSVGLETRVTVPNMPIRFTKIFYNQQNHYDVTT 146
cow     PGRKGEPGEAAYVYRSAFSVGLETRVTVPNVPIRFTKIFYNQQNHYDGST 142
rat     PGRKGEPGEAAYMYHSAFSVGLETRVTVPNVPIRFTKIFYNQQNHYDGST 147
mouse   PGRKGEPGEAAYMYRSAFSVGLETRVTVPNVPIRFTKIFYNQQNHYDGST 150
chicken MGMKGQKGESSYVYRSAFSVGLTERAPHPNVPIRFTKIFYNEQNHYDSST 145

human   GKFHCNIPGLYYFAYHITVYMKDVKVSLFKKDKAMLFTYDQYQENNVDQA 197
macaque GKFHCNIPGLYYFAYHITVYMKDVKVSLFKKDKAMLFTYDQYQENNVDQA 196
dog     GKFHCNIPGLYYFSYHITVYLKDVKVSLYKKDKAMLFTYDQYQEKNVDQA 197
boar    GKFHCNIPGLYYFSFHITVYLKDVKVSLYKKDKAVLFTYDQYQDKNVDQA 196
cow     GKFYCNIPGLYYFSYHITVYMKDVKVSLFKKDKAVLFTYDQYQEKNVDQA 192
rat     GKFHCNIPGLYYFSYHITVYMKDVKVSLFKKDKAVLFTYDQYQEKNVDQA 197
mouse   GKFYCNIPGLYYFSYHITVYMKDVKVSLFKKDKAVLFTYDQYQEKNVDQA 200
chicken GKFLCSIPGTYFFAYHLTVYMTDVKVSLYKKDKAVIFTYDQFQENNVDQA 195

human   SGSVLLHLEVGDQVWLQVYGEGERNGLYADNDNDSTFTGFLLYHDTN-- 244
macaque SGSVLLHLEVGDQVWLQVYGEGERNGLYADNDNDSTFTGFLLYHDTN-- 243
dog     SGSVLLHLEVGDQVWLQVYGDGDSYGIYADNVNDSTFTGFLLYHDTN-- 244
boar    SGSVLLYLEKGDQVWLQAYGDEENNGVYADNVNDSIFTGFLLYHNIE-- 243
cow     SGSVLLHLEVGDQVWLQVYEGENHNGVYADNVNDSTFTGFLLYHNIVE- 240
rat     SGSMLLHLEVGDQVWLQVYGEGDNNGLYADNVNDSTFTGFLLYHDTN-- 244
mouse   SGSVLLHLEVGDQVWLQVYGDGDHNGLYADNVNDSTFTGFLLFHDTN-- 247
chicken SGSVLLHLSLGDEVWLQVYGEGNNNGVYADNINDSTFMGFLLYPDTDDR 244
```

Figure 3. Exposed Hydrophobic Residues in Ad Collagen Region and Alternative Polar Residues

| Residue # | WT | Accessible Surface Area | HEI | Alternative Polar Residues |
|---|---|---|---|---|
| 43 | ILE | 89.59 | 0.891 | D, E, H, K, N, Q, R, S |
| 53 | PRO | 83.5 | 0.41 | D, E, H, K, N, Q, R, S |
| 73 | LEU | 119.19 | 1.049 | D, E, H, K, N, Q, R, S |
| 74 | ILE | 73.07 | 0.727 | D, E, H, K, N, Q, R, S |
| 76 | PRO | 83.75 | 0.411 | D, E, H, K, N, Q, R, S |
| 80 | ILE | 100.8 | 1.002 | D, E, H, K, N, Q, R, S |
| 85 | VAL | 91.22 | 0.677 | D, E, H, K, N, Q, R, S |
| 94 | PHE | 110.3 | 0.886 | D, E, H, K, N, Q, R, S |
| 97 | ILE | 100.49 | 0.999 | D, E, H, K, N, Q, R, S |

Figure 4. Alternative Polar Residues from Ortholog Alignment

| Residue # | WT | Ortholog Residues | Alternative Polar Residues |
|---|---|---|---|
| 43 | ILE | ALA | None |
| 53 | PRO | None | None |
| 73 | LEU | VAL | None |
| 74 | ILE | LEU, VAL, THR, GLN | THR, GLN |
| 76 | PRO | VAL | None |
| 80 | ILE | THR, PRO | THR |
| 85 | VAL | MET, ALA | None |
| 94 | PHE | None | None |
| 97 | ILE | THR, HIS | THR, HIS |

Fig. 5A. Regions of High Electrostatic Potential in Ad Collagen Region and Compensating Substitutions

| | | Electrostatic Potential | | | |
|---|---|---|---|---|---|
| Residue # | WT | Chain A | Chain B | Chain C | Compensating Substitutions |
| 55 | ARG | -0.74 | -0.86 | -0.25 | Not needed |
| 56 | ASP | 0.31 | 0.66 | 0.91 | Not needed |
| 57 | GLY | -0.94 | -0.88 | -0.50 | ARG, HIS, LYS |
| 58 | ARG | -1.01 | -0.61 | -0.64 | Not needed |
| 59 | ASP | 0.03 | 0.55 | 0.24 | Not needed |
| 60 | GLY | -0.66 | -0.75 | -1.00 | ARG, HIS, LYS |
| 61 | THR | -0.36 | -0.42 | -0.74 | ARG, HIS, LYS |
| 62 | PRO | -0.58 | -0.37 | -0.48 | ARG, HIS, LYS |
| 63 | GLY | -0.51 | -0.54 | -0.61 | ARG, HIS, LYS |
| 65 | LYS | -1.02 | -0.93 | -0.90 | Not needed |
| 66 | GLY | 0.09 | -0.11 | -0.56 | ARG, HIS, LYS |
| 67 | GLU | 0.41 | 0.58 | 0.36 | Not needed |
| 68 | LYS | -0.82 | -1.19 | -1.09 | Not needed |
| 70 | ASP | 0.30 | 0.30 | 0.54 | Not needed |
| 71 | PRO | -0.33 | -0.72 | -0.78 | ARG, HIS, LYS |

Fig. 5B. Regions of High Electrostatic Potential in Ad Collagen Region and Compensating Substitutions

| | | Electrostatic Potential | | | |
|---|---|---|---|---|---|
| **Residue #** | **WT** | **Chain A** | **Chain B** | **Chain C** | **Compensating Substitutions** |
| 77 | LYS | -0.83 | -0.60 | -0.64 | Not needed |
| 80 | ILE | -0.78 | -0.91 | -0.77 | ARG, HIS, LYS |
| 81 | GLY | -0.93 | -0.92 | -0.73 | ARG, HIS, LYS |
| 83 | THR | -0.59 | -0.82 | -0.81 | ARG, HIS, LYS |
| 84 | GLY | -0.54 | -0.65 | -0.74 | ARG, HIS, LYS |
| 87 | GLY | -0.54 | -0.49 | -0.43 | ARG, HIS, LYS |
| 88 | ALA | -0.59 | -0.59 | -0.45 | ARG, HIS, LYS |
| 90 | GLY | -0.20 | -0.48 | -0.66 | ARG, HIS, LYS |
| 91 | PRO | 0.29 | -0.08 | -0.51 | ARG, HIS, LYS |
| 93 | GLY | 0.73 | 0.67 | 0.20 | ASP, GLU |
| 94 | PHE | 0.62 | 0.37 | 0.34 | ASP, GLU |
| 95 | PRO | 0.55 | 0.40 | 0.30 | ASP, GLU |
| 96 | GLY | 0.56 | 0.43 | 0.52 | ASP, GLU |
| 97 | ILE | 0.59 | 0.41 | 0.51 | ASP, GLU |
| 98 | GLN | 0.69 | 0.62 | 0.74 | ASP, GLU |
| 99 | GLY | 1.00 | 0.99 | 0.83 | ASP, GLU |
| 101 | LYS | -0.53 | -0.06 | 0.46 | Not needed |
| 102 | GLY | 0.09 | 0.40 | 0.61 | ASP, GLU |
| 103 | GLU | 0.17 | 0.33 | 0.64 | Not needed |
| 104 | PRO | -0.60 | -0.77 | -0.37 | ARG, HIS, LYS |
| 105 | GLY | -0.82 | -0.82 | -0.67 | ARG, HIS, LYS |
| 107 | GLY | -0.67 | -0.94 | -1.00 | ARG, HIS, LYS |
| 108 | ALA | -0.31 | -0.63 | -0.71 | ARG, HIS, LYS |

Figure 6. Hydroxyprolines in Ad Collagen Region and Appropriate Substitutions

| **Residue #** | **WT** | **Appropriate Substitutions** |
|---|---|---|
| 44 | PRO | THR, GLN |
| 47 | PRO | THR, GLN |
| 53 | PRO | THR, GLN |
| 62 | PRO | THR, GLN |
| 71 | PRO | THR, GLN |
| 86 | PRO | THR, GLN |
| 95 | PRO | THR, GLN |
| 104 | PRO | THR, GLN |

Figure 7A. Aromatic Amino Acids in Ad Collagen Region and Appropriate Substitutions

| **Residue #** | **WT** | **Appropriate Substitutions** |
|---|---|---|
| 46 | HIS | PRO, ASP, GLU, LYS |

Figure 7B. Aromatic Amino Acids in Ad Collagen Region and Appropriate Substitutions

| Residue # | WT | Appropriate Substitutions |
|---|---|---|
| 49 | HIS | PRO, ASP, GLU, LYS |
| 94 | PHE | PRO, ASP, GLU, LYS |

Figure 8. Especially Preferred Substitutions in Ad Collagen Region

| Residue # | WT | Substitutions |
|---|---|---|
| 40 | MET | ALA, LEU |
| 43 | ILE | PRO, GLU |
| 44 | PRO | THR, GLN, ARG, LYS |
| 46 | HIS | PRO, ASP, GLU |
| 47 | PRO | THR, GLN, ARG, LYS |
| 49 | HIS | PRO |
| 53 | PRO | THR, GLN |
| 62 | PRO | THR, GLN, LYS |
| 71 | PRO | THR, GLN, ARG, LYS |
| 73 | LEU | PRO, ASP, GLU |
| 74 | ILE | THR, GLN, ARG, LYS |
| 80 | ILE | THR, GLN, ARG, LYS |
| 83 | THR | LYS |
| 85 | VAL | PRO |
| 86 | P | THR, GLN, ARG |
| 94 | F | PRO, ASP, GLU |
| 95 | P | THR, GLN, ARG, LYS |
| 97 | I | PRO, ASP, GLU |
| 104 | P | THR, GLN, ARG, LYS |

Figure 9. Exposed Hydrophobic Residues in gAd

| Residue # | WT | Accessible Surface Area | HEI |
|---|---|---|---|
| 109 | TYR | 163.4 | 0.66 |
| 110 | VAL | 72.2 | 0.54 |
| 111 | TYR | 112.7 | 0.46 |
| 122 | TYR | 131.9 | 0.53 |
| 125 | ILE | 64.3 | 0.64 |
| 135 | ILE | 91.3 | 0.91 |
| 184 | PHE | 50.8 | 0.41 |
| 207 | VAL | 93.6 | 0.69 |
| 224 | LEU | 184.7 | 1.63 |
| 225 | TYR | 104.6 | 0.42 |

Figure 11. Exposed Hydrophobic Residues in Ad Globular Region and Alternative Polar Residues

| Residue # | WT | Alternative Polar Residues (ΔE <2 kcal/mol) |
|---|---|---|
| 109 | Y | D, E, H, K, N, Q, R |
| 110 | V | D, E, H, K, N, Q, R, S |
| 111 | Y | D, E, H, K, N, Q, R |
| 122 | Y | D, E, H, N, R, S |
| 125 | I | D, E, H, K, N, Q, R, S |
| 135 | I | D, E, H, K, N, Q, R |
| 184 | F | D, H, K, N, R |
| 207 | V | D, E, H, K, N, Q, R, S |
| 224 | L | D, E, H, K, N, Q, R, S |
| 225 | Y | D, E, H, K, N, Q, R, S |

Figure 12. Alternative Polar Residues from Ortholog Alignment

| Residue # | WT | Ortholog Residues | Alternative Polar Residue |
|---|---|---|---|
| 109 | TYR | TYR | None |
| 110 | VAL | MET, VAL | None |
| 111 | TYR | HIS, TYR | HIS |
| 122 | TYR | TYR, ARG | ARG |
| 125 | ILE | HIS, ILE, VAL | HIS |
| 135 | ILE | ILE | None |
| 184 | PHE | PHE | None |
| 207 | VAL | LEU, LYS, VAL | LYS |
| 224 | LEU | ILE, LEU, VAL | None |
| 225 | TYR | TYR | None |

Figure 13A. Energies of Most Favorable Polar Substitutions for gAd Solvent-exposed Hydrophobic Positions

| | | Chain A | Chain B | Chain C |
|---|---|---|---|---|
| 109 | TYR | H: 0.33<br>K: 1.56<br>N: 1.89<br>Q: 0.56<br>R: 0.80 | D: 1.71<br>E: 1.95<br>H: 0.49<br>K: 1.75<br>N: 1.47<br>Q: 0.36<br>R: 1.36 | D: 1.86<br>E: 1.92<br>H: 0.52<br>N: 1.72<br>Q: 0.57<br>R: 1.67 |

Figure 13B. Energies of Most Favorable Polar Substitutions for gAd Solvent-exposed Hydrophobic Positions

| | | Chain A | Chain B | Chain C |
|---|---|---|---|---|
| 110 | VAL | D: 0.80<br>E: 1.22<br>H: 0.43<br>K: 0.27<br>N: 0.72<br>Q: 0.00<br>R: 0.96<br>S: 1.44 | D: 0.00<br>E: 0.29<br>H: 0.85<br>K: 1.19<br>N: 1.39<br>Q: 0.61<br>R: 1.23 | D: 0.00<br>E: 0.27<br>H: 0.78<br>K: 1.59<br>N: 1.30<br>Q: 0.16<br>R: 1.70<br>S: 1.83 |
| 111 | TYR | H: 0.96 | D: 1.44<br>E: 1.00<br>H: 0.18<br>K: 1.84<br>N: 1.72<br>Q: 1.02<br>R: 1.48 | H: 0.37<br>N: 1.53<br>R: 1.56 |
| 122 | TYR | H: 1.77 | D: 1.4<br>H: 1.51<br>N: 1.73<br>S: 1.42 | E: 1.77<br>H: 1.43<br>N: 1.93<br>R: 1.87<br>S: 1.85 |
| 125 | ILE | D: 0.63<br>E: 0.00<br>H: 0.25<br>K: 0.78<br>N: 0.45<br>Q: 0.03<br>R: 0.49<br>S: 1.43 | D: 1.34<br>E: 0.00<br>H: 0.83<br>N: 1.30<br>Q: 1.12<br>R: 1.84 | E: 0.00<br>H: 1.46<br>K: 1.92<br>N: 1.76<br>Q: 1.63 |
| 135 | ILE | D: 1.69<br>E: 0.16<br>H: 0.29<br>K: 1.61<br>N: 1.57<br>Q: 0.63<br>R: 1.02 | D: 1.34<br>E: 0.70<br>H: 0.48<br>K: 1.15<br>N: 1.61<br>Q: 0.57<br>R: 1.26 | D: 1.61<br>E: 0.38<br>H: 0.39<br>K: 0.88<br>N: 1.72<br>Q: 0.91<br>R: 0.65 |
| 184 | PHE | D: 1.68<br>H: 0.85<br>N: 0.92<br>R: 2.00 | H: 0.00<br>K: 0.74<br>N: 1.28<br>R: 1.35 | K: 1.70<br>R: 0.00 |

Figure 13C. Energies of Most Favorable Polar Substitutions for gAd Solvent-exposed Hydrophobic Positions

| | | Chain A | Chain B | Chain C |
|---|---|---|---|---|
| 207 | VAL | D: 0.99<br>E: 1.03<br>H: 1.38<br>K: 1.03<br>N: 0.84<br>Q: 0.09<br>R: 0.69<br>S: 1.87 | D: 0.61<br>E: 0.68<br>H: 0.32<br>K: 0.39<br>N: 0.32<br>Q: 0.00<br>R: 0.19<br>S: 1.74 | D: 1.32<br>E: 1.06<br>H: 1.34<br>K: 1.10<br>N: 1.00<br>Q: 0.00<br>R: 0.30 |
| 224 | LEU | D: 1.39<br>E: 1.23<br>H: 0.00<br>K: 0.93<br>N: 0.87<br>Q: 0.52<br>R: 0.20<br>S: 1.78 | D: 1.13<br>E: 0.89<br>H: 0.01<br>K: 0.68<br>N: 0.56<br>Q: 0.13<br>R: 0.00<br>S: 1.48 | D: 1.47<br>E: 1.25<br>H: 0.00<br>K: 1.04<br>N: 0.87<br>Q: 0.57<br>R: 0.22<br>S: 1.86 |
| 225 | TYR | D: 0.87<br>E: 1.50<br>H: 0.61<br>K: 0.99<br>N: 0.53<br>Q: 1.18<br>R: 0.60<br>S: 0.70 | D: 0.99<br>E: 1.91<br>H: 1.37<br>K: 1.76<br>N: 0.74<br>Q: 1.66<br>R: 1.44<br>S: 0.96 | D: 0.00<br>E: 0.98<br>H: 0.18<br>K: 0.67<br>N: 0.14<br>Q: 0.88<br>R: 0.80<br>S: 0.95 |

Figure 14. Alternative Polar Residues

| Residue # | WT | Alternative Polar Residues |
|---|---|---|
| 109 | Y | D, E, H, K, N, Q, R |
| 110 | V | D, E, H, K, N, Q, R, S |
| 111 | Y | D, E, H, K, N, Q, R |
| 122 | Y | D, E, H, N, R, S |
| 125 | I | D, E, H, K, N, Q, R, S |
| 135 | I | D, E, H, K, N, Q, R |
| 184 | F | D, H, K, N, R |
| 207 | V | D, E, H, K, N, Q, R, S |
| 224 | L | D, E, H, K, N, Q, R, S |
| 225 | Y | D, E, H, K, N, Q, R, S |

Figure 15A. Regions of High Electrostatic Potential in gAd

| | | Electrostatic Potential | | |
|---|---|---|---|---|
| Residue Number | Residue Name | Chain A | Chain B | Chain C |

Figure 15B. Regions of High Electrostatic Potential in gAd

| | | Electrostatic Potential | | |
|---|---|---|---|---|
| Residue Number | Residue Name | Chain A | Chain B | Chain C |
| 110 | VAL | 0.67 | 0.60 | 0.61 |
| 129 | PRO | 0.49 | 0.53 | 0.48 |
| 134 | LYS | -0.84 | -0.88 | -0.85 |
| 144 | ASP | 0.45 | 0.49 | 0.53 |
| 165 | THR | -0.82 | -0.82 | -0.83 |
| 166 | VAL | -0.68 | -0.66 | -0.68 |
| 167 | TYR | -0.52 | -0.56 | -0.55 |
| 168 | MET | -0.60 | -0.59 | -0.59 |
| 169 | LYS | -0.61 | -0.49 | -0.46 |
| 171 | VAL | -1.00 | -0.94 | -0.99 |
| 172 | LYS | -1.14 | -1.07 | -1.17 |
| 173 | VAL | -0.76 | -0.70 | -0.74 |
| 182 | MET | 0.52 | 0.56 | 0.54 |
| 184 | PHE | -0.62 | -0.58 | -0.80 |
| 185 | THR | -0.91 | -0.89 | -0.89 |
| 186 | TYR | -0.83 | -0.71 | -0.87 |
| 187 | ASP | -0.81 | -0.70 | -0.79 |
| 188 | GLN | -0.55 | -0.32 | -0.75 |
| 189 | TYR | -1.41 | -1.32 | -1.37 |
| 190 | GLN | -1.13 | -1.08 | -1.22 |
| 192 | LYS | -0.73 | -0.47 | -0.49 |
| 194 | VAL | -0.41 | -0.58 | -0.52 |
| 195 | ASP | -0.79 | -0.72 | -0.79 |
| 196 | GLN | -1.06 | -1.07 | -1.03 |
| 197 | ALA | -1.22 | -1.19 | -1.19 |
| 204 | HIS | -0.51 | -0.50 | -0.52 |
| 208 | GLY | 0.51 | 0.38 | 0.36 |
| 209 | ASP | 0.67 | 0.70 | 0.67 |
| 210 | GLN | 0.72 | 0.74 | 0.74 |
| 212 | TRP | 0.49 | 0.51 | 0.50 |
| 222 | ASN | -0.44 | -0.50 | -0.35 |
| 227 | ASP | -0.45 | -0.47 | -0.54 |
| 229 | ASP | -0.61 | -0.59 | -0.64 |
| 230 | ASN | -0.59 | -0.58 | -0.60 |
| 240 | TYR | 0.55 | 0.54 | 0.54 |

Figure 16. Energies of Most Favorable Positively Charged Residues to Replace Aspartate 227 and 229 in gAd

| Residue Number | Residue Name | Chain A | Chain B | Chain C |
|---|---|---|---|---|
| 227 | ASP | **H : 0.00**<br>K : 0.90<br>R : 1.32 | H : 1.54<br>**K : 0.00**<br>R : 0.81 | H : 0.48<br>**K : 0.00**<br>R : 0.30 |
| 229 | ASP | H : 0.66<br>K : 1.27<br>R : 0.50 | **H : 0.00**<br>K : 0.18<br>R : 0.37 | H : 0.52<br>K : 0.67<br>R : 0.66 |

Figure 17. Energies of Most Favorable Non-glycine Residues to Replace Cysteine 152 in Ad

| Residue Number | Residue Name | Chain A | Chain B | Chain C |
|---|---|---|---|---|
| 152 | CYS | T: 1.78<br>S: 2.08<br>A: 3.56<br>N: 4.89 | T: 1.13<br>S: 2.39<br>A: 3.85<br>V: 4.20<br>N: 4.27 | T: 1.22<br>S: 1.78<br>A: 3.32<br>V: 4.78 |

Figure 18A. Energies of Most Favorable Non-glycine, Polar Residues to Replace Methionine 128 and 182 in Ad

| Residue Number | Residue Name | Chain A | Chain B | Chain C |
|---|---|---|---|---|
| 128 | MET | A : 1.52<br>D : 1.03<br>E : 1.46<br>**H : 0.00**<br>K : 1.96<br>M : 0.80<br>N : 0.98<br>Q : 0.88<br>R : 1.40<br>S : 1.32<br>T : 1.04 | A : 1.21<br>D : 1.04<br>E : 0.83<br>H : 0.06<br>K : 2.70<br>M : 1.85<br>N : 1.32<br>Q : 1.01<br>R : 1.51<br>S : 1.59<br>T : 0.81 | A : 1.22<br>D : 1.06<br>E : 0.92<br>**H : 0.00**<br>K : 1.80<br>M : 1.61<br>N : 0.99<br>Q : 0.71<br>R : 1.22<br>S : 1.37<br>T : 0.78 |

Figure 18B. Energies of Most Favorable Non-glycine, Polar Residues to Replace Methionine 128 and 182 in Ad

| Residue Number | Residue Name | Chain A | Chain B | Chain C |
|---|---|---|---|---|
| 182 | MET | A : 2.18<br>D : 3.79<br>**E : 0.00**<br>K ; 3.48<br>M : 0.37<br>N : 3.45<br>Q : 1.17<br>R : 2.89<br>S : 1.39<br>T : 0.20 | A : 2.66<br>D : 3.60<br>E : 2.18<br>K : 3.16<br>M : 2.13<br>N : 2.45<br>Q : 2.66<br>R : 2.74<br>S : 2.63<br>T : 1.21 | A : 2.22<br>D : 2.23<br>E : 1.68<br>K : 3.31<br>M : 2.40<br>N : 3.12<br>Q : 2.35<br>R : 3.27<br>S : 2.61<br>T : 1.22 |

Figure 19. Energies of Favored Coupled Substitutions at Positions 109, 110 and 111

| 109 | 110 | 111 | $\Delta$E | | | 109 | 110 | 111 | $\Delta$E | | |
|---|---|---|---|---|---|---|---|---|---|---|---|
| Y | V | Y | Chain A | Chain B | Chain C | Y | V | Y | Chain A | Chain B | Chain C |
| H | D | H | 1.14 | 0.23 | 0.38 | D | D | H | | 1.13 | |
| H | E | H | 1.55 | 0.43 | 0.83 | E | E | H | | 1.17 | |
| H | H | H | 1.02 | 0.71 | 1.08 | H | A | H | 1.64 | | |
| H | K | H | 1.12 | 1.16 | 1.20 | H | H | E | 1.65 | | |
| H | Q | H | 0.52 | 0.27 | 0.59 | H | K | E | 1.54 | | |
| H | R | H | 1.64 | 0.98 | 1.08 | H | N | H | 1.27 | | |
| H | T | H | 1.67 | 1.17 | 1.15 | K | D | E | | | 0.98 |
| Q | D | H | 1.51 | 0.33 | 0.57 | K | E | E | | | 0.88 |
| R | D | E | 1.50 | 1.16 | 1.01 | K | R | E | | | 0.70 |
| E | D | H | | 0.72 | 0.78 | K | T | E | | | 0.93 |
| E | Q | H | 1.38 | 1.00 | | N | D | H | | 1.06 | |
| H | Q | E | 0.99 | 0.95 | | Q | A | E | 1.52 | | |
| K | H | E | 1.17 | | 0.60 | Q | A | H | | 1.11 | |
| K | K | E | 1.17 | | 0.74 | Q | E | H | | 0.76 | |
| K | N | E | 1.54 | | 1.22 | Q | H | E | | | 1.13 |
| K | Q | E | 0.88 | | 0.45 | Q | K | H | 1.44 | | |
| Q | H | H | 1.33 | 1.12 | | Q | T | E | | | 1.10 |
| Q | Q | E | 1.40 | | 1.24 | R | N | E | 1.41 | | |
| Q | T | H | | 0.91 | 1.12 | R | Q | H | 1.70 | | |
| R | E | E | | 1.13 | 1.13 | | | | | | |
| R | H | E | 1.18 | | 0.96 | | | | | | |
| R | K | E | 1.25 | | 1.09 | | | | | | |
| R | Q | E | 0.80 | | 0.70 | | | | | | |
| R | R | E | 1.70 | | 0.93 | | | | | | |

Figure 20. Energies of Favored Coupled Substitutions at Positions 122 and 125

| 122 | 125 | ΔE | | | 122 | 125 | ΔE | | |
|---|---|---|---|---|---|---|---|---|---|
| Y | I | Chain A | Chain B | Chain C | Y | I | Chain A | Chain B | Chain C |
| D | H | 1.60 | 0.81 | 1.17 | R | E | 0.22 | 0.16 | 0.35 |
| D | K | 0.84 | 0.35 | 1.21 | R | H | 1.48 | 1.16 | 1.13 |
| D | N | 1.70 | 0.89 | 1.60 | R | N | 1.59 | 1.38 | 1.44 |
| D | Q | 1.16 | 0.35 | 1.65 | R | Q | 1.08 | 0.80 | 1.40 |
| D | R | 0.78 | 0.71 | 1.17 | R | R | 1.46 | 1.62 | 1.80 |
| D | T | 1.67 | 0.91 | 1.36 | R | T | 1.57 | 1.30 | 1.26 |
| E | H | 1.77 | 0.46 | 0.00 | S | A | 1.55 | 0.59 | 1.02 |
| E | K | 1.62 | 1.12 | 0.93 | S | D | 1.26 | 0.31 | 1.42 |
| E | Q | 1.25 | 0.93 | 1.28 | S | E | 0.91 | 0.21 | 1.29 |
| E | R | 1.05 | 0.93 | 0.56 | S | H | 1.00 | 0.82 | 1.14 |
| H | A | 1.40 | 0.86 | 1.11 | S | N | 1.08 | 0.57 | 1.21 |
| H | D | 0.79 | 0.49 | 1.07 | S | Q | 0.59 | 0.00 | 1.37 |
| H | E | 0.00 | 0.28 | 0.47 | S | R | 0.92 | 0.76 | 1.43 |
| H | H | 0.85 | 0.81 | 0.78 | S | S | 1.78 | 0.95 | 1.41 |
| H | N | 0.82 | 0.89 | 1.29 | S | T | 1.08 | 0.51 | 1.04 |
| H | Q | 0.45 | 0.29 | 0.90 | D | A | | 0.93 | 1.33 |
| H | R | 0.81 | 1.07 | 1.61 | D | D | 1.98 | 0.81 | |
| H | S | 1.57 | 1.19 | 1.54 | D | E | 1.64 | 0.74 | |
| H | T | 0.91 | 0.77 | 1.08 | D | S | | 1.35 | 1.74 |
| K | A | 1.85 | 1.42 | 1.82 | E | A | | 1.51 | 1.35 |
| K | D | 1.38 | 0.12 | 1.33 | E | N | | 1.47 | 1.55 |
| K | E | 0.27 | 0.18 | 0.19 | E | S | | 1.83 | 1.72 |
| K | H | 1.28 | 1.54 | 1.70 | E | T | | 1.37 | 1.24 |
| K | N | 1.38 | 1.42 | 2.00 | H | K | 1.15 | 1.43 | |
| K | Q | 0.89 | 0.83 | 1.96 | K | R | 1.28 | 1.66 | |
| K | T | 1.37 | 1.32 | 1.83 | N | K | 1.54 | 1.48 | |
| N | A | 1.81 | 0.91 | 1.15 | N | S | | 1.29 | 1.55 |
| N | D | 1.55 | 0.67 | 1.57 | Q | A | | 1.40 | 1.43 |
| N | E | 0.97 | 0.57 | 1.32 | Q | K | 1.93 | 1.95 | |
| N | H | 1.28 | 1.10 | 1.30 | Q | S | | 1.76 | 1.85 |
| N | N | 1.37 | 0.90 | 1.37 | R | A | | 1.39 | 1.25 |
| N | Q | 0.85 | 0.33 | 1.52 | R | K | 1.81 | 1.98 | |
| N | R | 1.19 | 1.09 | 1.63 | R | S | | 1.74 | 1.66 |
| N | T | 1.36 | 0.86 | 1.18 | S | K | 1.27 | 1.11 | |
| Q | D | 1.78 | 1.09 | 1.79 | A | D | | 1.82 | |
| Q | E | 0.81 | 0.90 | 1.22 | A | E | | 1.73 | |
| Q | H | 1.63 | 1.54 | 1.52 | A | Q | | 1.53 | |
| Q | N | 1.70 | 1.39 | 1.62 | E | D | | 1.57 | |

Figure 20 (cont.) Energies of Favored Coupled Substitutions at Positions 122 and 125

| 122 | 125 | ΔE | | | 122 | 125 | ΔE | | |
|---|---|---|---|---|---|---|---|---|---|
| Y | I | Chain A | Chain B | Chain C | Y | I | Chain A | Chain B | Chain C |
| Q | Q | 0.76 | 0.81 | 1.66 | E | E | | 1.49 | |
| Q | R | 1.58 | 1.58 | 1.82 | K | K | 1.63 | | |
| Q | T | 1.71 | 1.31 | 1.45 | K | S | | 1.75 | |

Figure 21. Energies of Favored Coupled Substitutions at Positions 224 and 225

| 224 | 225 | ΔE | | | 224 | 225 | ΔE | | |
|---|---|---|---|---|---|---|---|---|---|
| L | Y | Chain A | Chain B | Chain C | L | Y | Chain A | Chain B | Chain C |
| H | A | 1.35 | 0.22 | 1.51 | H | K | | 1.90 | |
| H | D | 1.15 | **0.00** | 1.22 | H | Q | | 1.20 | |
| H | E | 1.86 | 1.10 | 1.99 | H | R | | 1.61 | |
| H | H | 1.23 | 0.86 | 1.80 | K | A | | 1.22 | |
| H | N | 1.44 | 0.29 | 1.64 | K | D | | 0.66 | |
| H | S | 1.55 | 0.43 | 1.69 | K | N | | 0.97 | |
| H | T | 1.67 | 0.56 | 1.83 | K | Q | | 1.93 | |
| Q | D | 1.73 | 0.46 | 1.85 | K | S | | 1.27 | |
| Q | N | 1.63 | 0.41 | 1.93 | K | T | | 1.40 | |
| R | D | 1.65 | 0.28 | 1.90 | N | A | | 0.98 | |
| R | E | 1.41 | 0.59 | 1.62 | N | D | | 1.40 | |
| R | H | 1.17 | 0.81 | 1.76 | N | N | | 1.18 | |
| K | E | 1.87 | 0.89 | | N | R | | 1.90 | |
| K | H | 1.89 | 1.23 | | N | S | | 1.11 | |
| N | H | 1.78 | 1.80 | | N | T | | 1.26 | |
| Q | H | 1.48 | 1.10 | | Q | A | | 0.73 | |
| R | A | 1.95 | 0.13 | | Q | E | | 1.59 | |
| R | N | 1.83 | 0.46 | | Q | Q | | 1.48 | |
| R | S | 1.96 | 0.48 | | Q | R | | 1.27 | |
| D | A | | 1.59 | | Q | S | | 0.66 | |
| D | N | | 1.75 | | Q | T | | 0.70 | |
| D | S | | 1.65 | | R | K | | 1.56 | |
| D | T | | 1.76 | | R | Q | | 1.11 | |
| E | A | | 1.48 | | R | R | | 1.44 | |
| E | H | | 1.57 | | R | T | | 0.62 | |
| E | N | | 1.62 | | S | A | | 1.97 | |
| E | S | | 1.54 | | S | S | | 1.98 | |
| E | T | | 1.64 | | | | | | |

Figure 22. Energies of Favored Substitutions at Core Positions within gAd

| | | 115 | 123 | 130 | 132 | 150 | 160 | 164 | 166 | 171 | 173 | 175 | 205 | 211 | 213 | 215 | 234 |
|---|---|---|---|---|---|---|---|---|---|---|---|---|---|---|---|---|---|
| WT | | F | V | I | **F** | F | F | I | V | **V** | V | L | **L** | **V** | L | V | **F** |
| 1 | 0.00 | --- | --- | V | --- | --- | --- | V | F | --- | --- | --- | --- | --- | --- | --- | --- |
| 2 | 0.10 | --- | --- | --- | --- | --- | --- | V | F | --- | --- | --- | --- | --- | --- | --- | --- |
| 3 | 0.28 | --- | --- | V | --- | --- | --- | V | F | --- | --- | --- | --- | --- | I | --- | --- |
| 4 | 1.22 | --- | I | V | --- | --- | --- | --- | --- | --- | --- | --- | --- | --- | --- | --- | --- |
| 5 | 1.94 | --- | --- | --- | --- | --- | --- | V | F | --- | --- | --- | --- | --- | V | --- | --- |
| 6 | 2.07 | --- | I | --- | --- | --- | --- | --- | --- | --- | --- | --- | --- | --- | --- | --- | --- |
| 7 | 2.58 | --- | --- | --- | --- | --- | --- | --- | --- | --- | --- | --- | --- | --- | --- | --- | --- |
| 8 | 2.83 | --- | --- | V | --- | --- | --- | --- | --- | --- | --- | --- | --- | --- | --- | --- | --- |
| 9 | 2.88 | --- | I | V | --- | --- | --- | --- | --- | --- | --- | --- | --- | --- | I | --- | --- |
| 10 | 3.49 | --- | --- | --- | --- | --- | --- | V | F | --- | --- | --- | --- | --- | I | --- | --- |
| 11 | 3.88 | --- | I | V | --- | --- | --- | V | --- | --- | --- | --- | --- | --- | --- | --- | --- |
| 12 | 3.99 | --- | --- | V | --- | --- | --- | V | --- | --- | --- | --- | --- | --- | --- | --- | --- |
| 13 | 4.26 | --- | I | V | --- | --- | --- | V | --- | --- | --- | --- | --- | --- | I | --- | --- |
| 14 | 4.28 | --- | --- | V | --- | --- | --- | V | F | --- | --- | --- | --- | --- | V | --- | --- |
| 15 | 4.43 | --- | I | --- | --- | --- | --- | V | --- | --- | --- | --- | --- | --- | --- | --- | --- |
| 16 | 4.68 | --- | I | V | --- | --- | --- | V | --- | --- | --- | --- | --- | --- | V | --- | --- |
| 17 | 4.76 | --- | --- | V | --- | --- | --- | --- | F | --- | --- | --- | --- | --- | V | --- | --- |
| 18 | 4.83 | --- | I | V | --- | --- | --- | --- | --- | --- | --- | --- | --- | --- | --- | I | --- |
| 19 | 5.03 | --- | I | V | --- | --- | --- | --- | --- | --- | --- | --- | --- | --- | V | --- | --- |
| 20 | 5.12 | --- | I | --- | --- | --- | --- | --- | --- | --- | --- | --- | --- | --- | I | --- | --- |
| 21 | 5.38 | --- | --- | V | --- | --- | --- | --- | --- | --- | --- | --- | --- | --- | I | --- | --- |
| 22 | 5.39 | --- | --- | --- | --- | --- | --- | V | --- | --- | --- | --- | --- | --- | --- | --- | --- |
| 23 | 5.39 | --- | --- | V | --- | --- | --- | V | --- | --- | --- | --- | --- | --- | I | --- | --- |
| 24 | 5.50 | --- | --- | V | --- | --- | --- | --- | --- | --- | --- | --- | --- | --- | --- | I | --- |
| 25 | 5.59 | --- | --- | V | --- | --- | --- | --- | --- | --- | --- | --- | --- | --- | V | --- | --- |
| 26 | 5.61 | --- | I | V | --- | --- | --- | --- | --- | --- | --- | V | --- | --- | --- | --- | --- |
| 27 | 5.61 | --- | I | V | --- | --- | --- | --- | --- | --- | --- | V | --- | --- | I | --- | --- |
| 28 | 5.75 | --- | --- | V | --- | --- | --- | --- | F | --- | --- | --- | --- | --- | --- | --- | --- |
| 29 | 5.97 | --- | --- | --- | --- | --- | --- | L | --- | --- | --- | --- | --- | --- | --- | --- | --- |
| 30 | 6.15 | --- | --- | V | --- | --- | --- | V | --- | --- | --- | --- | --- | --- | V | --- | --- |
| 31 | 6.32 | --- | --- | --- | --- | L | --- | V | F | --- | --- | --- | --- | --- | --- | --- | --- |
| 32 | 6.32 | --- | --- | V | --- | --- | --- | V | --- | --- | --- | --- | --- | --- | --- | I | --- |
| 33 | 6.40 | --- | --- | --- | --- | --- | --- | --- | --- | --- | --- | --- | --- | --- | V | --- | --- |
| 34 | 6.42 | --- | --- | V | --- | --- | --- | --- | --- | --- | --- | V | --- | --- | --- | --- | --- |
| 35 | 6.49 | --- | --- | V | --- | --- | --- | --- | F | --- | --- | --- | --- | --- | I | --- | --- |
| 36 | 6.65 | --- | --- | V | --- | --- | --- | --- | --- | --- | --- | V | --- | --- | I | --- | --- |
| 37 | 6.77 | --- | --- | V | --- | --- | --- | L | --- | --- | --- | --- | --- | --- | --- | --- | --- |
| 38 | 6.93 | --- | I | --- | --- | --- | --- | --- | --- | --- | --- | --- | --- | --- | --- | I | --- |

Figure 22 (cont.) Energies of Favored Substitutions at Core Positions within gAd

| | | 115 | 123 | 130 | 132 | 150 | 160 | 164 | 166 | 171 | 173 | 175 | 205 | 211 | 213 | 215 | 234 |
|---|---|---|---|---|---|---|---|---|---|---|---|---|---|---|---|---|---|
| WT | | F | V | I | F | F | F | I | V | V | V | L | L | V | L | V | F |
| 39 | 7.08 | --- | --- | V | --- | L | --- | V | F | --- | --- | --- | --- | --- | --- | --- | --- |
| 40 | 7.35 | --- | --- | V | --- | --- | --- | V | --- | --- | --- | --- | --- | --- | I | I | --- |
| 41 | 7.37 | --- | --- | --- | --- | --- | --- | --- | F | --- | --- | --- | --- | --- | --- | --- | --- |
| 42 | 7.50 | I | --- | V | --- | --- | --- | V | F | --- | --- | --- | --- | --- | I | --- | --- |
| 43 | 7.50 | --- | I | V | --- | L | --- | --- | --- | --- | --- | --- | --- | --- | --- | --- | --- |
| 44 | 7.65 | L | --- | V | --- | --- | --- | V | F | --- | --- | --- | --- | --- | I | --- | --- |
| 45 | 7.80 | --- | --- | V | --- | --- | --- | L | --- | --- | --- | --- | --- | --- | --- | I | --- |
| 46 | 7.82 | --- | --- | V | --- | --- | --- | L | --- | --- | --- | --- | --- | --- | I | --- | --- |
| 47 | 7.83 | --- | --- | L | --- | --- | --- | --- | --- | --- | --- | --- | --- | --- | --- | --- | --- |
| 48 | 7.86 | --- | --- | --- | --- | --- | --- | V | F | --- | --- | V | --- | --- | --- | --- | --- |
| 49 | 7.86 | --- | I | V | --- | --- | --- | L | --- | --- | --- | --- | --- | --- | V | --- | --- |
| 50 | 7.93 | --- | --- | --- | --- | --- | L | V | F | --- | --- | --- | --- | --- | --- | --- | --- |
| 51 | 7.99 | --- | --- | V | --- | --- | --- | L | --- | --- | --- | --- | --- | --- | V | --- | --- |
| 52 | 7.99 | --- | --- | V | --- | --- | --- | V | --- | --- | --- | --- | --- | --- | V | I | --- |
| 53 | 8.08 | --- | I | --- | --- | L | --- | --- | --- | --- | --- | --- | --- | --- | --- | --- | --- |
| 54 | 8.09 | --- | --- | --- | --- | --- | --- | --- | --- | --- | --- | --- | --- | --- | --- | I | --- |
| 55 | 8.13 | --- | --- | V | --- | --- | --- | --- | --- | --- | --- | --- | --- | --- | I | I | --- |
| 56 | 8.14 | I | --- | V | --- | --- | --- | V | F | --- | --- | --- | --- | --- | --- | --- | --- |
| 57 | 8.19 | --- | --- | V | --- | --- | --- | L | --- | --- | --- | --- | --- | --- | I | I | --- |
| 58 | 8.27 | V | --- | V | --- | --- | --- | V | F | --- | --- | --- | --- | --- | --- | --- | --- |
| 59 | 8.27 | --- | --- | V | --- | L | --- | V | F | --- | --- | --- | --- | --- | I | --- | --- |
| 60 | 8.29 | --- | --- | --- | --- | L | --- | V | F | --- | --- | --- | --- | --- | I | --- | --- |
| 61 | 8.31 | I | --- | V | --- | --- | --- | V | F | --- | --- | --- | --- | --- | V | --- | --- |
| 62 | 8.36 | --- | I | V | --- | L | --- | --- | --- | --- | --- | --- | --- | --- | I | --- | --- |
| 63 | 8.49 | --- | I | V | --- | --- | --- | --- | --- | --- | --- | --- | --- | --- | I | I | --- |
| 64 | 8.58 | --- | --- | --- | --- | L | --- | --- | --- | --- | --- | --- | --- | --- | --- | --- | --- |
| 65 | 8.64 | --- | --- | V | --- | L | --- | --- | --- | --- | --- | --- | --- | --- | --- | --- | --- |
| 66 | 8.64 | --- | I | V | --- | --- | L | --- | --- | --- | --- | --- | --- | --- | --- | --- | --- |
| 67 | 8.75 | --- | I | V | --- | --- | --- | V | --- | --- | --- | V | --- | --- | I | --- | --- |
| 68 | 8.84 | --- | I | --- | --- | --- | --- | L | --- | --- | --- | --- | --- | --- | --- | --- | --- |
| 69 | 8.85 | --- | --- | --- | --- | --- | I | --- | --- | --- | --- | --- | --- | --- | --- | --- | --- |
| 70 | 8.88 | --- | I | V | --- | --- | I | --- | --- | --- | --- | --- | --- | --- | --- | --- | --- |
| 71 | 8.90 | --- | I | --- | --- | --- | --- | V | --- | --- | --- | --- | --- | --- | --- | I | --- |
| 72 | 8.99 | --- | I | V | --- | L | --- | V | --- | --- | --- | --- | --- | --- | --- | --- | --- |
| 73 | 8.99 | --- | --- | V | --- | --- | I | V | F | --- | --- | --- | --- | --- | I | --- | --- |
| 74 | 9.00 | V | --- | V | --- | --- | --- | V | F | --- | --- | --- | --- | --- | I | --- | --- |
| 75 | 9.01 | --- | I | V | --- | L | --- | V | --- | --- | --- | --- | --- | --- | I | --- | --- |
| 76 | 9.07 | --- | I | V | --- | --- | --- | --- | --- | --- | --- | V | --- | --- | V | --- | --- |
| 77 | 9.09 | --- | --- | V | --- | --- | --- | --- | --- | --- | --- | V | --- | --- | V | --- | --- |
| 78 | 9.13 | --- | --- | --- | --- | --- | --- | --- | --- | --- | --- | --- | --- | --- | I | --- | --- |

Figure 22 (cont.) Energies of Favored Substitutions at Core Positions within gAd

| | | 115 | 123 | 130 | 132 | 150 | 160 | 164 | 166 | 171 | 173 | 175 | 205 | 211 | 213 | 215 | 234 |
|---|---|---|---|---|---|---|---|---|---|---|---|---|---|---|---|---|---|
| 79 | 9.21 | --- | --- | V | --- | --- | V | V | F | --- | --- | --- | --- | --- | I | --- | --- |
| 80 | 9.27 | V | --- | V | --- | --- | --- | V | F | --- | --- | --- | --- | --- | V | --- | --- |
| 81 | 9.28 | W | I | V | --- | --- | V | V | --- | --- | --- | --- | --- | --- | --- | --- | --- |
| 82 | 9.33 | L | I | --- | --- | --- | --- | --- | --- | --- | --- | --- | --- | --- | --- | --- | --- |
| 83 | 9.34 | --- | I | V | --- | --- | --- | V | --- | --- | --- | F | --- | --- | --- | --- | --- |
| 84 | 9.34 | --- | --- | --- | --- | --- | --- | V | --- | --- | --- | --- | --- | --- | I | --- | --- |
| 85 | 9.39 | --- | --- | V | --- | L | --- | --- | --- | --- | --- | --- | --- | --- | I | --- | --- |
| 86 | 9.40 | --- | --- | V | --- | --- | --- | V | F | --- | --- | V | --- | --- | I | --- | --- |
| 87 | 9.43 | --- | I | V | --- | --- | --- | V | --- | --- | --- | F | --- | --- | I | --- | --- |
| 88 | 9.45 | --- | --- | --- | --- | --- | --- | V | --- | --- | --- | --- | --- | --- | V | --- | --- |
| 89 | 9.54 | --- | I | V | --- | --- | --- | L | --- | --- | --- | --- | --- | --- | --- | --- | --- |
| 90 | 9.56 | W | I | V | --- | --- | I | V | --- | --- | --- | --- | --- | --- | --- | --- | --- |
| 91 | 9.60 | --- | --- | --- | --- | --- | --- | V | F | --- | --- | F | --- | --- | V | --- | --- |
| 92 | 9.62 | --- | --- | V | --- | L | --- | V | --- | --- | --- | --- | --- | --- | I | --- | --- |
| 93 | 9.63 | --- | I | V | --- | --- | --- | V | --- | --- | --- | --- | --- | --- | --- | I | --- |
| 94 | 9.64 | I | --- | V | --- | --- | --- | --- | F | --- | --- | --- | --- | --- | I | --- | --- |
| 95 | 9.69 | I | --- | V | --- | --- | --- | --- | F | --- | --- | --- | --- | --- | V | --- | --- |
| 96 | 9.70 | --- | I | --- | --- | L | --- | V | --- | --- | --- | --- | --- | --- | --- | --- | --- |
| 97 | 9.71 | --- | --- | --- | --- | L | --- | V | --- | --- | --- | --- | --- | --- | --- | --- | --- |
| 98 | 9.71 | --- | I | V | --- | --- | I | --- | --- | --- | --- | --- | --- | --- | I | --- | --- |
| 99 | 9.74 | --- | I | V | --- | --- | --- | V | --- | --- | --- | --- | --- | --- | I | I | --- |
| 100 | 9.83 | --- | I | V | --- | L | --- | --- | --- | --- | --- | --- | --- | --- | V | --- | --- |

**Figure 25 – Vector for gAd Expression in *E. coli***

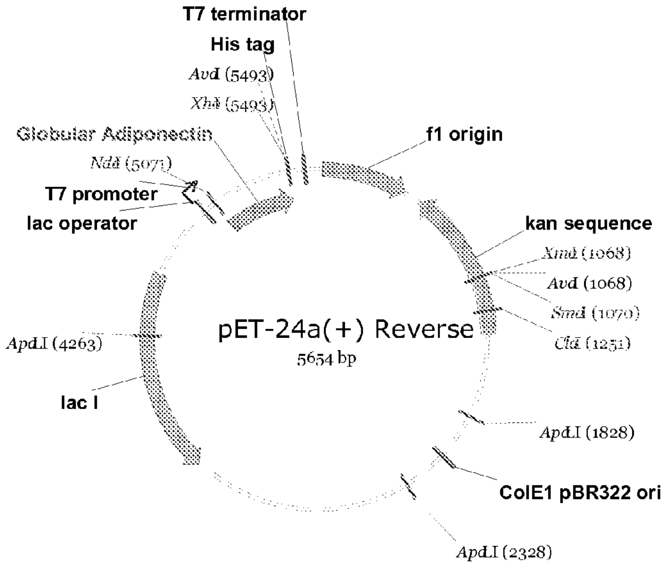

Figure 26 – gAd Variant Library #1

| Native residue | Position | Variant residue | Codon | Variant name |
|---|---|---|---|---|
| Y | 122 | E | GAA | Y122E |
| Y | 122 | H | CAC | Y122H |
| Y | 122 | S | TCC | Y122S |
| I | 125 | E | GAA | I125E |
| I | 125 | H | CAC | I125H |
| I | 125 | R | CGC | I125R |
| I | 125 | T | ACC | I125T |
| I | 135 | E | GAA | I135E |
| I | 135 | H | CAC | I135H |
| I | 135 | Q | CAG | I135Q |
| I | 135 | R | CGC | I135R |
| I | 135 | T | ACC | I135T |
| F | 184 | E | GAA | F184E |
| F | 184 | H | CAC | F184H |
| F | 184 | R | CGC | F184R |
| F | 184 | T | ACC | F184T |
| V | 207 | A | GCT | V207A |

Figure 26 – gAd Variant Library #1

| Native residue | Position | Variant residue | Codon | Variant name |
|---|---|---|---|---|
| V | 207 | E | GAA | V207E |
| V | 207 | K | AAA | V207K |
| V | 207 | Q | CAG | V207Q |
| V | 207 | T | ACC | V207T |
| L | 224 | E | GAA | L224E |
| L | 224 | H | CAC | L224H |
| L | 224 | Q | CAG | L224Q |
| L | 224 | R | CGC | L224R |
| L | 224 | S | TCC | L224S |
| Y | 225 | E | GAA | Y225E |
| Y | 225 | H | CAC | Y225H |
| Y | 225 | R | CGC | Y225R |
| Y | 225 | S | TCC | Y225S |
| D | 227 | R | CGC | D227R |
| D | 229 | R | CGC | D229R |
| Y | 122 | R | CGC | Y122R |

Figure 27a. SDS-PAGE Loading to Screen the Soluble or Insoluble Fractions of Library #1 Variants

Figure 27a

| Lane # | Variant | Fraction: [S]oluble, [I]nsoluble, or [T]otal |
|---|---|---|
| 1 | Y122E | T |
| 2 | Y122E | I |
| 3 | Y122E | S |
| 4 | I135H | T |
| 5 | I135H | I |
| 6 | I135H | S |
| 7 | V207D | T |
| 8 | V207D | I |
| 9 | V207D | S |
| 10 | L224R | I |
| 11 | L224R | S |
| 12 | NATIVE | I |
| 13 | NATIVE | S |
| 14 | I135Q | I |
| 15 | I135Q | S |
| 16 | V207E | I |
| 17 | V207E | S |
| 18 | L224S | I |
| 19 | L224S | S |
| 20 | Y122R | I |
| 21 | Y122R | S |
| 22 | Y122S | I |
| 23 | Y122S | S |
| 24 | I135R | I |
| 25 | I135R | S |
| 26 | V207K | I |
| 27 | V207K | S |
| 28 | Y225E | I |
| 29 | Y225E | S |
| 30 | pET-17b | I |
| 31 | pET-17b | S |
| 32 | I125E | I |
| 33 | I125E | S |
| 34 | I135T | I |
| 35 | I135T | S |
| 36 | V207Q | I |
| 37 | V207Q | S |

Figure 27a (cont.)

| Lane # | Variant | Fraction: [S]oluble, [I]nsoluble, or [T]otal |
|---|---|---|
| 38 | Y225H | I |
| 39 | Y225H | S |
| 40 | NATIVE | I |
| 41 | NATIVE | S |
| 42 | I125H | I |
| 43 | I125H | S |
| 44 | F184E | I |
| 45 | F184E | S |
| 46 | V207T | I |
| 47 | V207T | S |
| 48 | Y225R | I |
| 49 | Y225R | S |
| 50 | I125T | I |
| 51 | I125T | S |
| 52 | F184R | I |
| 53 | F184R | S |
| 54 | L224H | I |
| 55 | L224H | S |
| 56 | D227R | I |
| 57 | D227R | S |
| 58 | I135E | I |
| 59 | I135E | S |
| 60 | F184T | I |
| 61 | F184T | S |
| 62 | L224Q | I |
| 63 | L224Q | S |
| 64 | D229R | I |
| 65 | D229R | S |
| 66 | Y122H | I |
| 67 | I125R | I |
| 68 | I125R | S |
| 69 | F184H | I |
| 70 | F184H | S |
| 71 | L224E | I |
| 72 | L224E | S |
| 73 | Y225S | I |
| 74 | Y225S | S |
| 75 | Y122H | S |

Figure 27b – SDS-PAGE gels of 34 single amino acid substitution-containing gAd variants.
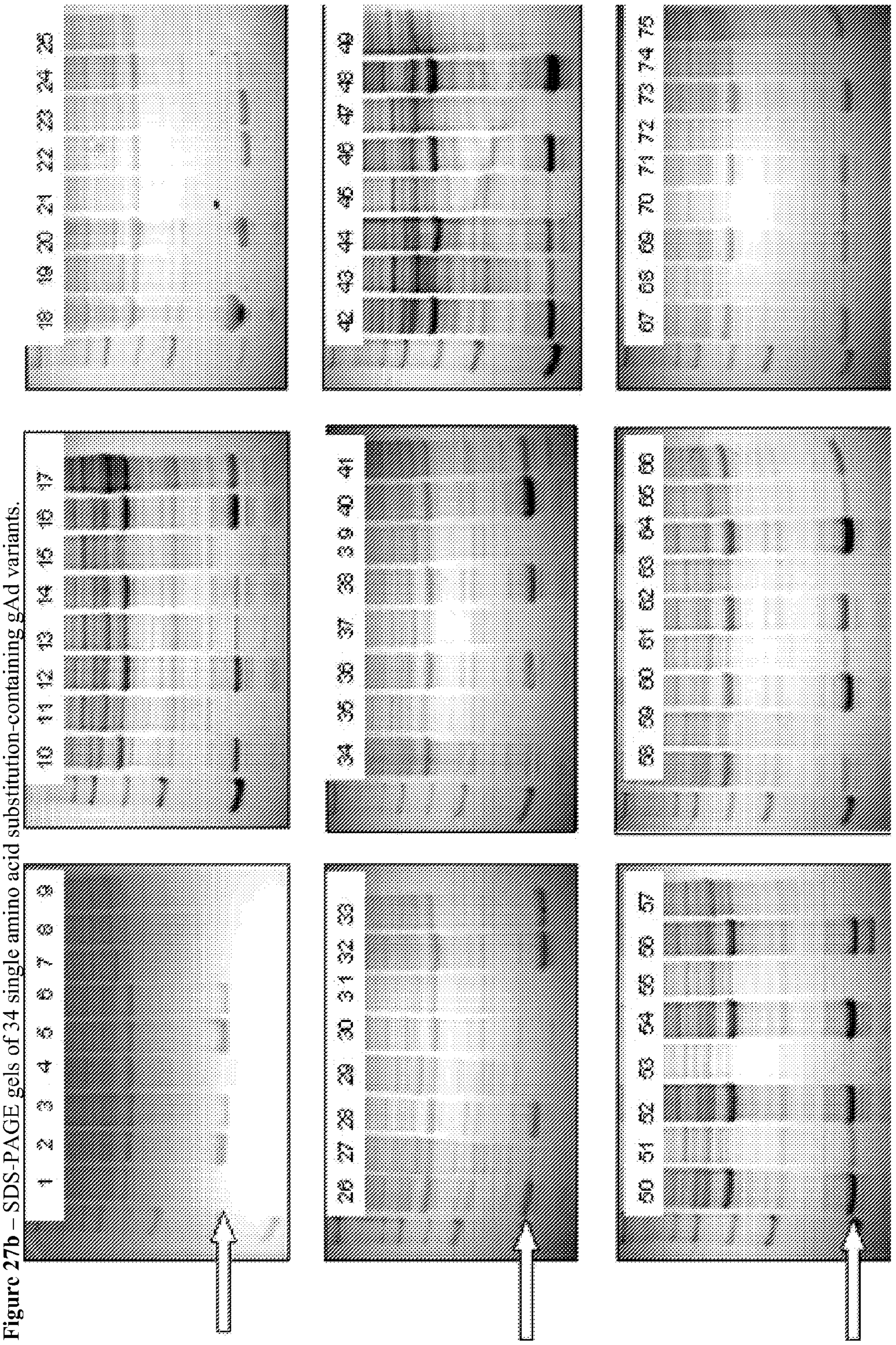

Figure 28a. SDS-PAGE Loading to Screen the Soluble or Insoluble Fractions of Select Variants in the Absence of Detergent

| Lane # | Variant | Fraction: [S]oluble, [I]nsoluble,or [T]otal | Lane # | Variant | Fraction: [S]oluble, [I]nsoluble, or [T]otal |
|---|---|---|---|---|---|
| 76 | NATIVE | T | 92 | Y122S | S |
| 77 | NATIVE | I | 93 | I125H | I |
| 78 | NATIVE | S | 94 | I125H | S |
| 79 | pET-17b | T | 95 | I125T | I |
| 80 | pET-17b | I | 96 | I125T | S |
| 81 | pET-17b | S | 97 | F184H | I |
| 82 | I125E | T | 98 | F184H | S |
| 83 | I125E | I | 99 | NATIVE | I |
| 84 | I125E | S | A | NATIVE | S |
| 85 | NATIVE | I | B | PET-17b | I |
| 86 | NATIVE | S | C | PET-17b | S |
| 87 | pET-17b | I | D | V207E | I |
| 88 | pET-17b | S | E | V207E | S |
| 89 | Y122H | I | F | V207K | I |
| 90 | Y122H | S | G | V207K | S |
| 91 | Y122S | I | | | |

Figure 28b – Solubility Or Soluble Expression Of Selected Single Amino Acid Substitution-Containing gAd Variants
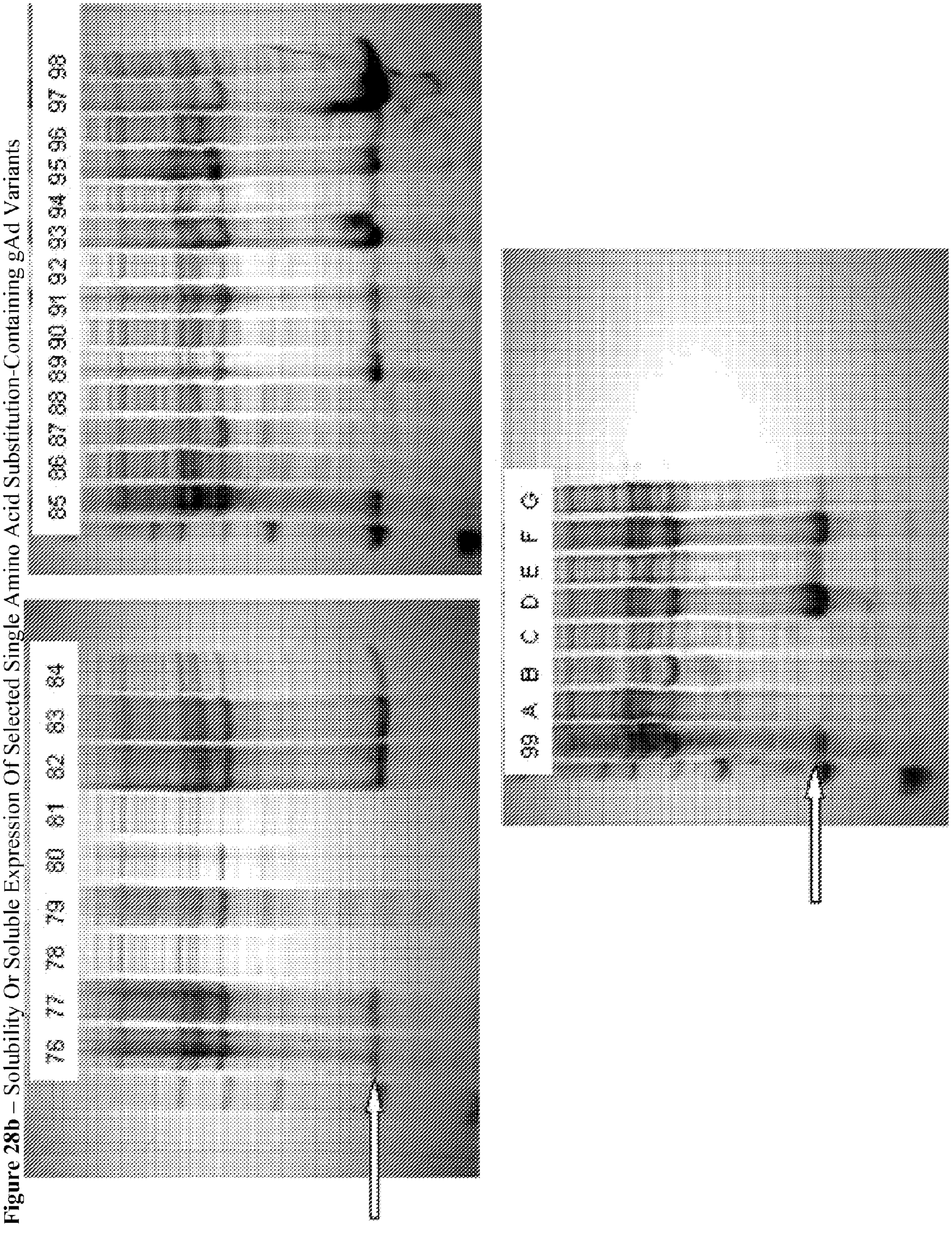

Figure 29a. SDS-PAGE Loading to Screen the Total, Soluble, and Insoluble Fractions of Double Mutant Globular Adiponectin Variants in the Presence of Detergent

Figure 29a

| Lane # | Variant | Fraction: [S]oluble, [I]nsoluble,or [T]otal |
|---|---|---|
| 1 | Y122H | T |
| 2 | Y122H | S |
| 3 | Y122H | I |
| 4 | Y122S | T |
| 5 | Y122S | S |
| 6 | Y122S | I |
| 7 | Marker | |
| 8 | I125E | T |
| 9 | I125E | S |
| 10 | I125E | I |
| 11 | I125H | T |
| 12 | I125H | S |
| 13 | I125H | I |
| 14 | Marker | |
| 15 | I125T | T |
| 16 | I125T | S |
| 17 | I125T | I |
| 18 | F184H | T |
| 19 | F184H | S |
| 20 | F184H | I |
| 21 | V207E | T |
| 22 | V207E | S |
| 23 | V207E | I |
| 24 | V207K | T |
| 25 | V207K | S |
| 26 | V207K | I |
| 27 | Marker | |
| 28 | F184H/Y122H | T |
| 29 | F184H/Y122H | S |
| 30 | F184H/Y122H | I |
| 31 | F184H/Y122S | T |
| 32 | F184H/Y122S | S |
| 33 | F184H/Y122S | I |

Figure 29a (cont.)

| Lane # | Variant | Fraction: [S]oluble, [I]nsoluble,or [T]otal |
|---|---|---|
| 34 | Marker | |
| 35 | F184H/I125E | T |
| 36 | F184H/I125E | S |
| 37 | F184H/I125E | I |
| 38 | F184H/I125H | T |
| 39 | F184H/I125H | S |
| 40 | F184H/I125H | I |
| 41 | F184H/I125T | T |
| 42 | F184H/I125T | S |
| 43 | F184H/I125T | I |
| 44 | F184H/V207E | T |
| 45 | F184H/V207E | S |
| 46 | F184H/V207E | I |
| 47 | Marker | |
| 48 | F184H/V207K | T |
| 49 | F184H/V207K | S |
| 50 | F184H/V207K | I |
| 51 | V207E/Y122H | T |
| 52 | V207E/Y122H | S |
| 53 | V207E/Y122H | I |
| 54 | Marker | |
| 55 | V207E/Y122S | T |
| 56 | V207E/Y122S | S |
| 57 | V207E/Y122S | I |
| 58 | V207E/I125E | T |
| 59 | V207E/I125E | S |
| 60 | V207E/I125E | I |
| 61 | V207E/I125H | T |
| 62 | V207E/I125H | S |
| 63 | V207E/I125H | I |
| 64 | V207E/I125T | T |
| 65 | V207E/I125T | S |
| 66 | V207E/I125T | I |
| 67 | Marker | |

Figure 29a (cont.)

| Lane # | Variant | Fraction: [S]oluble, [I]nsoluble,or [T]otal |
|---|---|---|
| 68 | V207K/Y122H | T |
| 69 | V207K/Y122H | S |
| 70 | V207K/Y122H | I |
| 71 | V207K/Y122S | T |
| 72 | V207K/Y122S | S |
| 73 | V207K/Y122S | I |
| 74 | Marker | |
| 75 | V207K/I125E | T |
| 76 | V207K/I125E | S |
| 77 | V207K/I125E | I |
| 78 | V207K/I125H | T |
| 79 | V207K/I125H | S |
| 80 | V207K/I125H | I |
| 81 | V207K/I125T | T |
| 82 | V207K/I125T | S |
| 83 | V207K/I125T | I |
| 84 | I125E/Y122H | T |
| 85 | I125E/Y122H | S |
| 86 | I125E/Y122H | I |
| 87 | Marker | |
| 88 | I125E/Y122S | T |
| 89 | I125E/Y122S | S |

Figure 29a (cont.)

| Lane # | Variant | Fraction: [S]oluble, [I]nsoluble,or [T]otal |
|---|---|---|
| 90 | I125E/Y122S | I |
| 91 | I125H/Y122H | T |
| 92 | I125H/Y122H | S |
| 93 | I125H/Y122H | I |
| 94 | Marker | |
| 95 | I125H/Y122S | T |
| 96 | I125H/Y122S | S |
| 97 | I125H/Y122S | I |
| 98 | I125T/Y122H | T |
| 99 | I125T/Y122H | S |
| 100 | I125T/Y122H | I |
| 101 | I125T/Y122S | T |
| 102 | I125T/Y122S | S |
| 103 | I125T/Y122S | I |
| 104 | Native | T |
| 105 | Native | S |
| 106 | Native | I |
| 107 | Marker | |
| 108 | pET-17b | T |
| 109 | pET-17b | S |
| 110 | pET-17b | I |

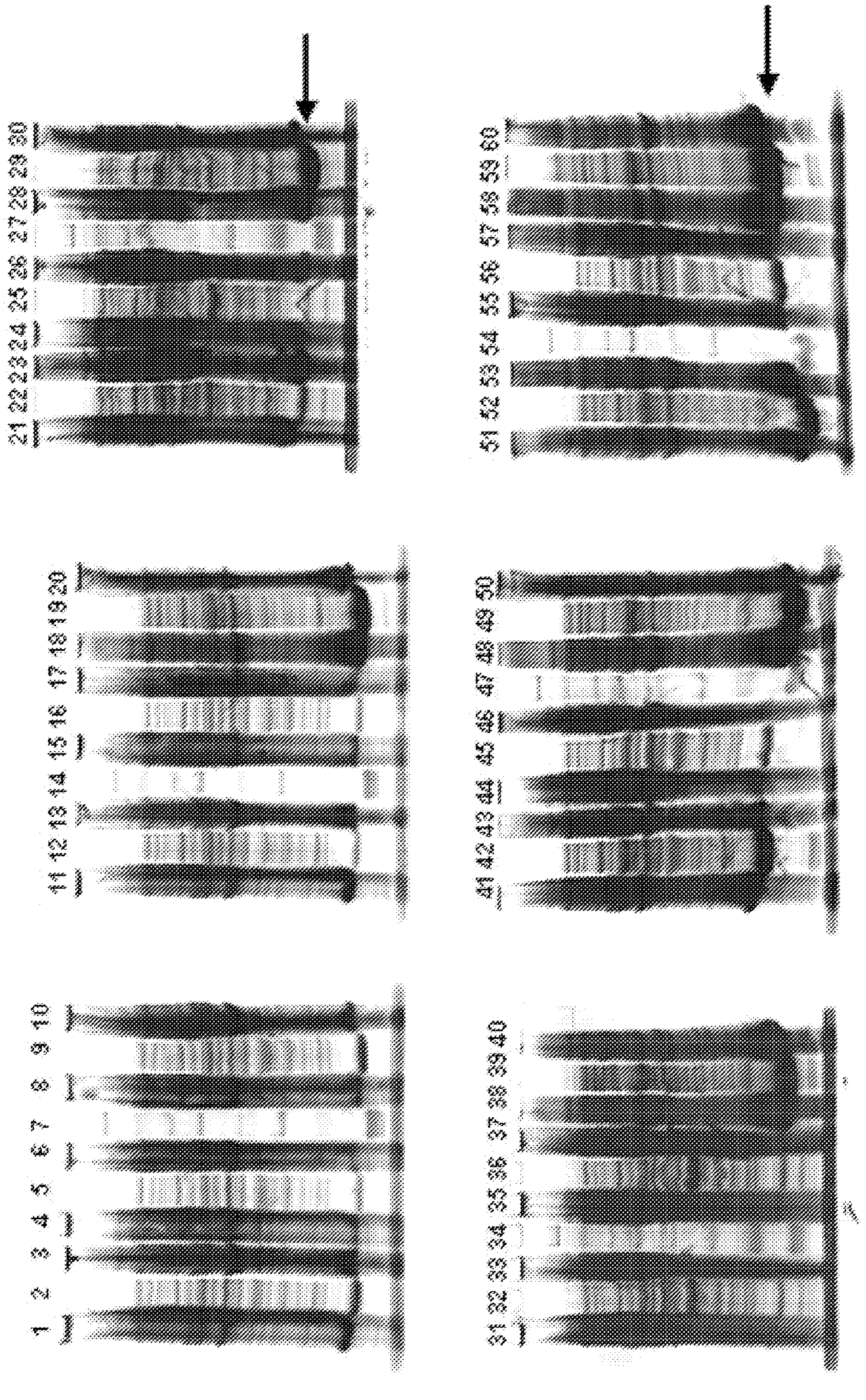
Figure 29b – SDS-PAGE of eight single amino acid and 23 double amino acid substitution-containing gAd variants.

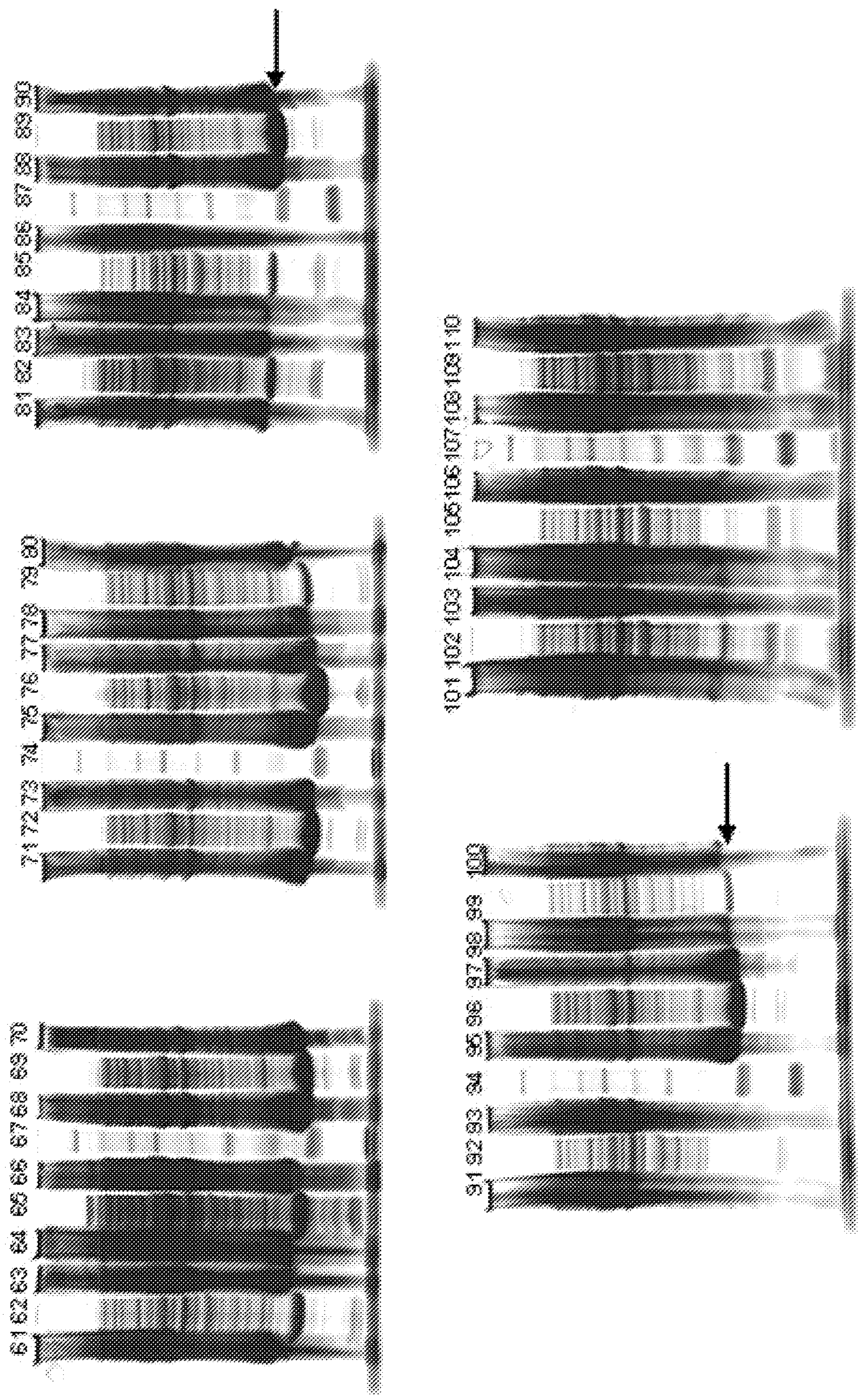
Figure 29b (continued) – SDS-PAGE of eight single amino acid and 23 double amino acid substitution-containing gAd variants.

Figure 30a. SDS-PAGE Loading to Screen the Soluble or Insoluble Fractions of Select Double Variants in the Absence of Detergent

| Lane # | Variant | Fraction: [S]oluble or [I]nsoluble | Lane # | Variant | Fraction: [S]oluble or [I]nsoluble |
|---|---|---|---|---|---|
| 1 | F184H | I | 13 | V207E/I125E | S |
| 2 | F184H | S | 14 | V207K/Y122S | I |
| 3 | F184H/Y122H | I | 15 | V207K/Y122S | S |
| 4 | F184H/Y122H | S | 16 | V207K/I125E | I |
| 5 | F184H/I125H | I | 17 | V207K/I125E | S |
| 6 | F184H/I125H | S | 18 | Marker | |
| 7 | Marker | | 19 | I125E/Y122S | I |
| 8 | F184H/I125T | I | 20 | I125E/Y122S | S |
| 9 | F184H/I125T | S | 21 | Native | I |
| 10 | F184H/V207K | I | 22 | Native | S |
| 11 | F184H/V207K | S | 23 | Native | I |
| 12 | V207E/I125E | I | 24 | Native | S |

Figure 30b – Solubility or Soluble Expression of Selected Single and Double Amino Acid Substitution-containing gAd Variants.
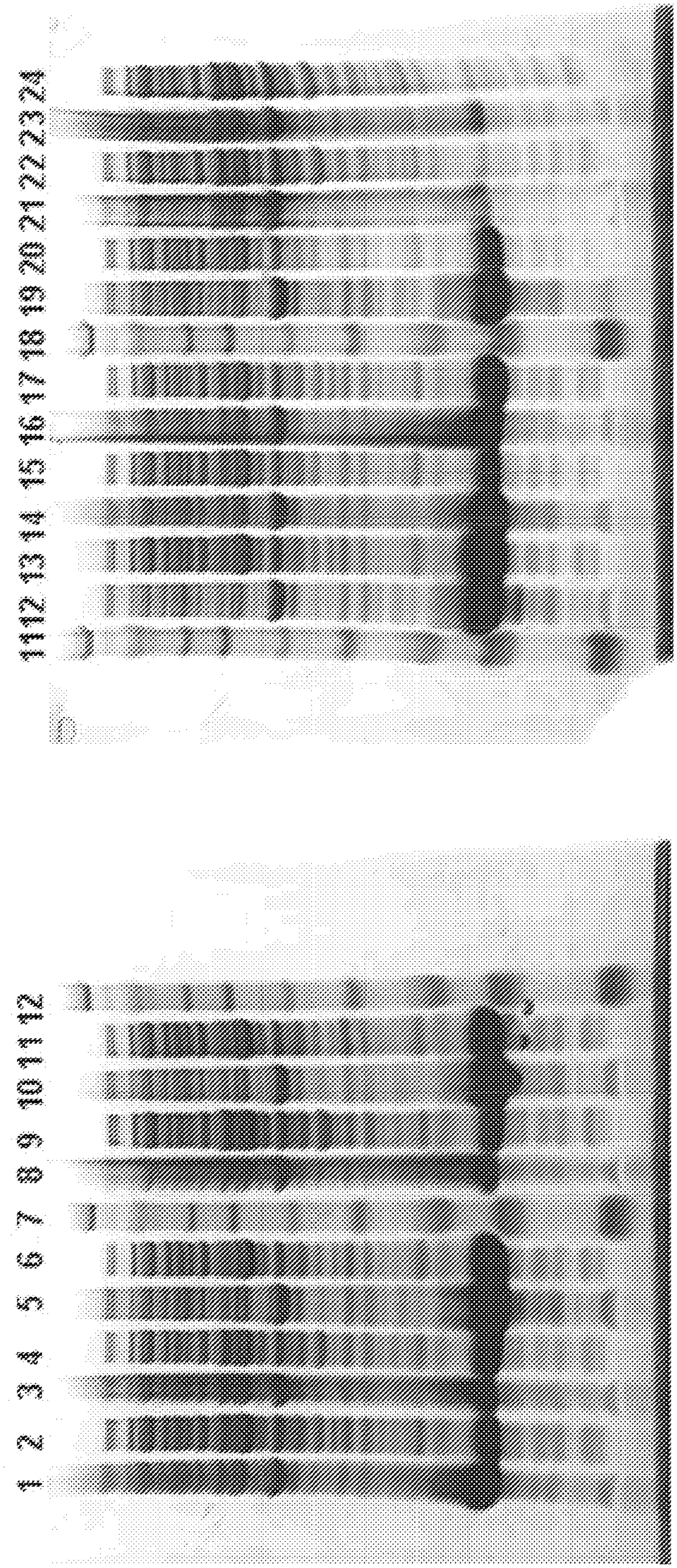

Figure 31a – SDS-Page gel showing purification and yield of selected gAd variants.

1 2 3 4 5 6 7 8 9 10

| Lane | variant | N | Average Purified mg/1L |
|---|---|---|---|
| 1 | F184H | 5 | 100 |
| 2 | Y122H/F184H | 1 | 100 |
| 3 | I125H/F184H | 1 | 100 |
| 4 | I125T/F184H | 5 | 90 |
| 5 | F184H/V207K | 1 | 40 |
| 6 | I125E/V207E | 1 | 60 |
| 7 | I122S/V207K | 1 | 60 |
| 8 | I125E/V207K | 5 | 200 |
| 9 | I122S/I125E | 8 | 250 |
| 10 | Wild-type | | |

Figure 32 – SDS-PAGE of the Detergent-Free Soluble Lysates from Native and I125E/V207E gAd.
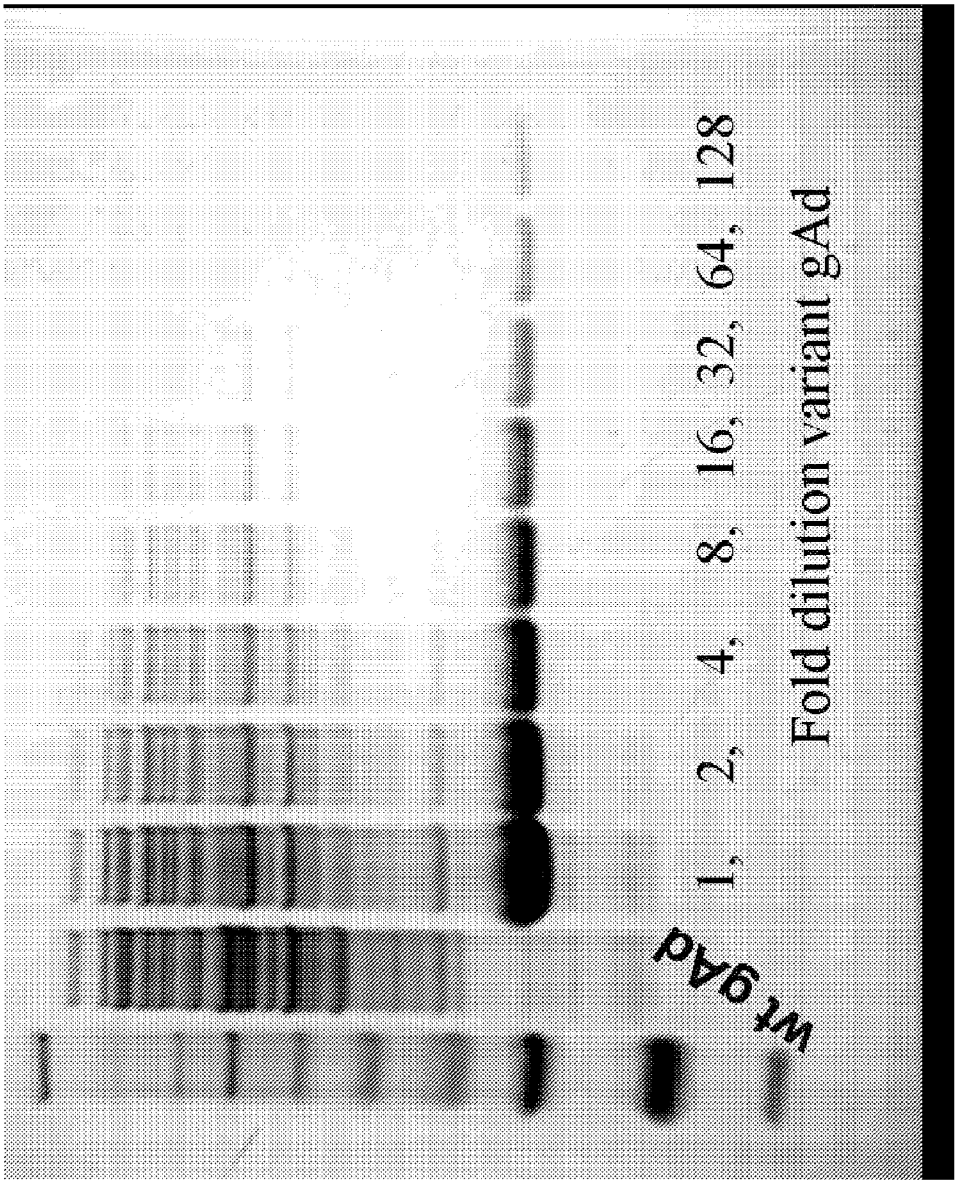

Figure 33 – SDS-PAGE of Total Protein of I125E/V207E/C152x Variants

| Lane | Variant |
|---|---|
| 1 | I125E/V207E/C152V |
| 2 | I125E/V207E/C152L |
| 3 | I125E/V207E/C152F |
| 4 | I125E/V207E/C152T |
| 5 | I125E/V207E/C152A |
| 6 | I125E/V207E/C152S |

Figure 34 – SDS-PAGE of Soluble Protein of I125E/V207E/C152 Variants

| Lane | Variant |
|---|---|
| 1 | I125E/V207E/C152V |
| 2 | I125E/V207E/C152L |
| 3 | I125E/V207E/C152F |
| 4 | I125E/V207E/C152T |
| 5 | I125E/V207E/C152A |
| 6 | I125E/V207E/C152S |

Figure 35 – Phase Contrast Time-Course Images of Mouse C2C12 Myotube Differentiation
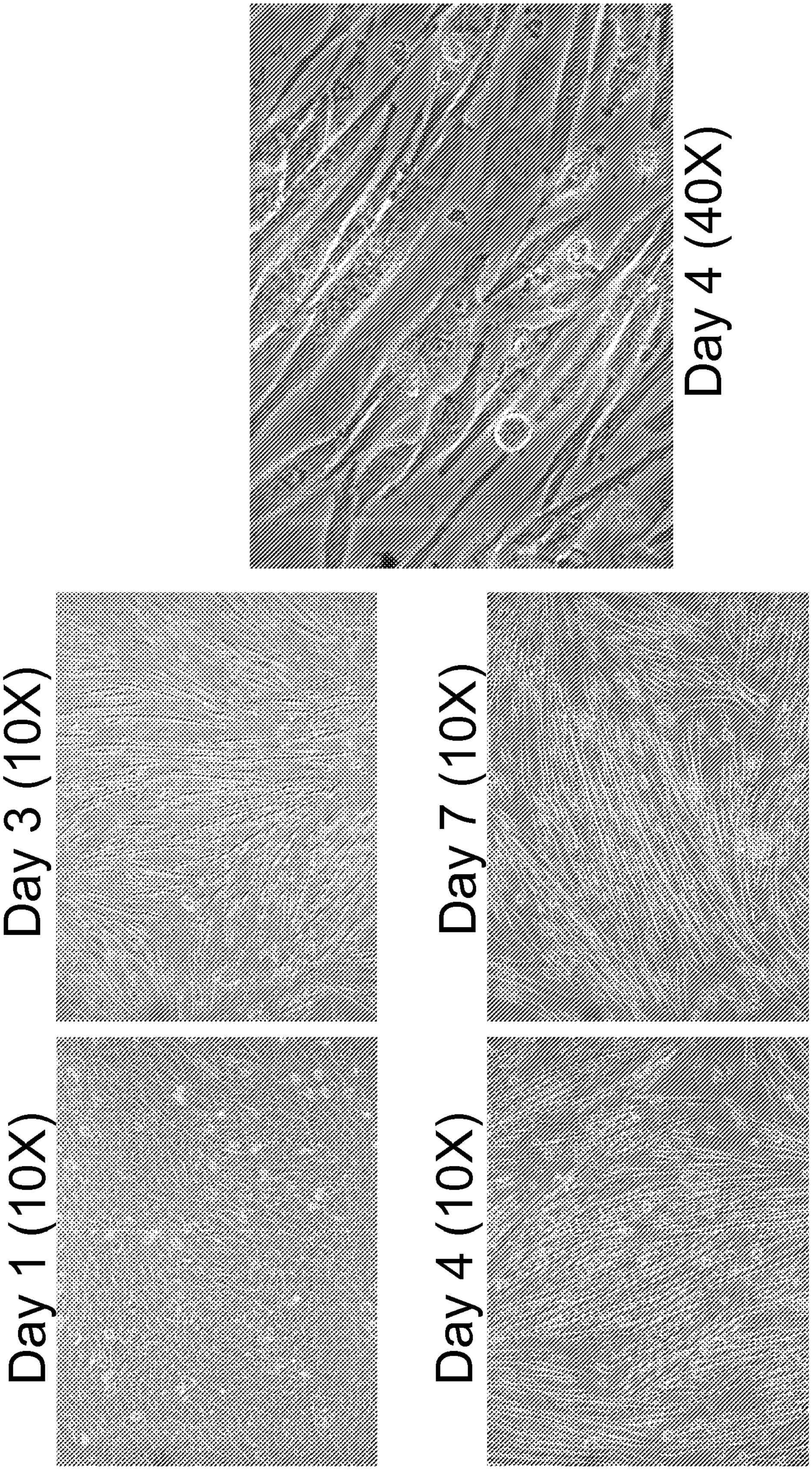

1 - Untreated cells
2 - AICAR
3 - Commercial gAd
4 - V207K/I125E
5 - F184H/Y122H
6 - Vector 1 – Untreated Cells
2 – F184H
3 – F184H/I125H
4 – F184H/I125T
5 – V207K/I125E
6 - Y122S/I125E

Figure 38: Energies of Preferred Substitutions for gAd.

| Figure 38 | | | |
|---|---|---|---|
| pos | wt | mut | E(PDA) |
| 108 | A | D | -1.321 |
| 108 | A | E | -1.406 |
| 108 | A | G | -0.923 |
| 108 | A | H | -0.878 |
| 108 | A | K | -0.853 |
| 108 | A | N | -1.679 |
| 108 | A | P | -0.033 |
| 108 | A | Q | -1.851 |
| 108 | A | R | -1.429 |
| 108 | A | S | -1.188 |
| 108 | A | T | -0.728 |
| 108 | A | V | -0.073 |
| 110 | V | E | -0.166 |
| 110 | V | Q | -0.329 |
| 110 | V | T | -0.083 |
| 111 | Y | F | -0.085 |
| 111 | Y | P | -0.790 |
| 112 | R | K | -0.414 |
| 120 | E | G | -2.401 |
| 120 | E | K | -1.297 |
| 120 | E | N | -0.220 |
| 120 | E | R | -0.775 |
| 121 | T | A | -0.949 |
| 121 | T | G | -8.683 |
| 121 | T | H | -1.364 |
| 121 | T | N | -0.689 |
| 121 | T | R | -0.475 |
| 121 | T | S | -2.328 |
| 122 | Y | D | -0.750 |
| 122 | Y | E | -0.747 |
| 122 | Y | G | -2.757 |
| 122 | Y | H | -0.633 |
| 122 | Y | M | -0.860 |
| 122 | Y | N | -0.750 |
| 122 | Y | Q | -0.638 |
| 122 | Y | S | -1.014 |
| 123 | V | I | -1.918 |
| 124 | T | I | -0.498 |
| 124 | T | R | -1.623 |
| 125 | I | E | -1.056 |
| 125 | I | F | -0.503 |
| 125 | I | L | -0.134 |
| 125 | I | T | -0.438 |
| 125 | I | V | -0.444 |
| 128 | M | A | -0.018 |
| 128 | M | D | -0.410 |
| 128 | M | E | -1.018 |
| 128 | M | F | -0.254 |
| 128 | M | H | -0.887 |

| Figure 38 | | | |
|---|---|---|---|
| pos | wt | mut | E(PDA) |
| 128 | M | I | -1.793 |
| 128 | M | L | -0.789 |
| 128 | M | N | -0.583 |
| 128 | M | Q | -0.726 |
| 128 | M | S | -0.724 |
| 128 | M | T | -1.719 |
| 128 | M | V | -2.072 |
| 128 | M | Y | -0.845 |
| 133 | T | E | -0.217 |
| 133 | T | F | -0.144 |
| 133 | T | H | -0.678 |
| 133 | T | L | -0.093 |
| 133 | T | M | -0.122 |
| 133 | T | N | -0.309 |
| 133 | T | Q | -0.358 |
| 133 | T | R | -0.890 |
| 133 | T | Y | -0.726 |
| 136 | F | Y | -0.385 |
| 139 | Q | E | -0.440 |
| 140 | Q | E | -0.830 |
| 140 | Q | P | -2.287 |
| 142 | H | P | -0.489 |
| 145 | G | A | -1.182 |
| 145 | G | D | -0.666 |
| 145 | G | E | -0.488 |
| 145 | G | H | -0.044 |
| 145 | G | I | -0.671 |
| 145 | G | M | -0.098 |
| 145 | G | N | -0.720 |
| 145 | G | P | -4.268 |
| 145 | G | Q | -0.261 |
| 145 | G | S | -1.846 |
| 145 | G | T | -2.282 |
| 145 | G | V | -1.090 |
| 146 | S | N | -0.034 |
| 146 | S | R | -0.678 |
| 151 | H | V | -0.111 |
| 151 | H | Y | -0.010 |
| 153 | N | D | -0.426 |
| 153 | N | E | -0.277 |
| 153 | N | F | -0.373 |
| 153 | N | H | -1.353 |
| 153 | N | I | -0.474 |
| 153 | N | K | -0.644 |
| 153 | N | M | -0.192 |
| 153 | N | Q | -1.424 |
| 153 | N | S | -0.331 |
| 153 | N | T | -0.906 |
| 153 | N | V | -0.869 |

| Figure 38 | | | |
|---|---|---|---|
| pos | wt | mut | E(PDA) |
| 153 | N | Y | -0.543 |
| 161 | A | S | -2.477 |
| 161 | A | T | -1.326 |
| 165 | T | H | -0.101 |
| 165 | T | V | -0.033 |
| 167 | Y | F | -0.234 |
| 169 | K | H | -0.308 |
| 169 | K | R | -1.101 |
| 172 | K | R | -1.449 |
| 174 | S | A | -0.596 |
| 174 | S | M | -0.806 |
| 178 | K | R | -0.982 |
| 180 | K | H | -0.924 |
| 180 | K | Q | -0.340 |
| 180 | K | R | -0.746 |
| 180 | K | S | -0.134 |
| 180 | K | T | -0.476 |
| 181 | A | D | -0.249 |
| 181 | A | E | -0.028 |
| 181 | A | F | -0.272 |
| 181 | A | K | -0.546 |
| 181 | A | P | -3.202 |
| 181 | A | R | -0.420 |
| 181 | A | S | -0.685 |
| 181 | A | T | -0.392 |
| 181 | A | W | -0.441 |
| 181 | A | Y | -0.603 |
| 182 | M | I | -0.098 |
| 182 | M | T | -0.366 |
| 182 | M | V | -0.994 |
| 184 | F | A | -0.149 |
| 184 | F | D | -0.981 |
| 184 | F | H | -3.242 |
| 184 | F | I | -2.543 |
| 184 | F | K | -2.925 |
| 184 | F | L | -1.592 |
| 184 | F | M | -1.006 |
| 184 | F | N | -2.950 |
| 184 | F | Q | -0.906 |
| 184 | F | R | -2.857 |
| 184 | F | S | -1.537 |
| 184 | F | T | -3.044 |
| 184 | F | V | -3.467 |
| 184 | F | W | -0.591 |
| 185 | T | I | -0.139 |
| 185 | T | K | -2.944 |
| 185 | T | R | -2.587 |

Figure 38 (cont)

| pos | wt | mut | E(PDA) |
|---|---|---|---|
| 186 | Y | F | -0.253 |
| 186 | Y | H | -2.970 |
| 186 | Y | K | -1.907 |
| 186 | Y | R | -2.821 |
| 186 | Y | T | -0.639 |
| 186 | Y | V | -1.258 |
| 187 | D | A | -3.968 |
| 187 | D | E | -0.981 |
| 187 | D | F | -0.374 |
| 187 | D | G | -3.029 |
| 187 | D | H | -6.416 |
| 187 | D | I | -5.092 |
| 187 | D | K | -6.964 |
| 187 | D | L | -3.533 |
| 187 | D | M | -5.248 |
| 187 | D | N | -5.960 |
| 187 | D | P | -8.179 |
| 187 | D | Q | -4.502 |
| 187 | D | R | -5.740 |
| 187 | D | S | -4.830 |
| 187 | D | T | -5.824 |
| 187 | D | V | -5.209 |
| 188 | Q | F | -0.138 |
| 188 | Q | H | -2.631 |
| 188 | Q | I | -0.618 |
| 188 | Q | K | -3.336 |
| 188 | Q | M | -0.711 |
| 188 | Q | P | -0.539 |
| 188 | Q | R | -1.431 |
| 188 | Q | T | -0.530 |
| 188 | Q | V | -0.606 |
| 189 | Y | A | -2.256 |
| 189 | Y | F | -0.154 |
| 189 | Y | G | -2.002 |
| 189 | Y | H | -6.181 |
| 189 | Y | I | -3.671 |
| 189 | Y | K | -8.451 |
| 189 | Y | L | -4.315 |
| 189 | Y | M | -4.121 |
| 189 | Y | N | -3.749 |
| 189 | Y | P | -1.056 |
| 189 | Y | Q | -3.052 |
| 189 | Y | R | -6.554 |
| 189 | Y | S | -3.828 |
| 189 | Y | T | -3.858 |
| 189 | Y | V | -3.440 |
| 191 | E | A | -1.162 |
| 191 | E | D | -0.420 |
| 191 | E | F | -1.217 |
| 191 | E | G | -1.475 |
| 191 | E | H | -3.257 |

Figure 38 (cont)

| pos | wt | mut | E(PDA) |
|---|---|---|---|
| 191 | E | I | -1.353 |
| 191 | E | K | -5.909 |
| 191 | E | L | -1.106 |
| 191 | E | M | -1.741 |
| 191 | E | N | -2.146 |
| 191 | E | Q | -2.117 |
| 191 | E | R | -4.436 |
| 191 | E | S | -2.299 |
| 191 | E | T | -2.287 |
| 191 | E | V | -1.459 |
| 191 | E | W | -2.042 |
| 191 | E | Y | -2.604 |
| 192 | K | G | -0.209 |
| 192 | K | R | -0.052 |
| 193 | N | F | -0.039 |
| 193 | N | G | -0.433 |
| 193 | N | W | -0.196 |
| 193 | N | Y | -0.544 |
| 194 | V | I | -0.010 |
| 194 | V | T | -0.229 |
| 195 | D | A | -4.748 |
| 195 | D | G | -2.648 |
| 195 | D | I | -1.101 |
| 195 | D | K | -6.175 |
| 195 | D | L | -2.161 |
| 195 | D | M | -3.858 |
| 195 | D | N | -4.424 |
| 195 | D | P | -0.338 |
| 195 | D | Q | -4.399 |
| 195 | D | S | -5.049 |
| 195 | D | T | -4.726 |
| 195 | D | V | -3.003 |
| 196 | Q | F | -1.515 |
| 196 | Q | G | -0.249 |
| 196 | Q | H | -4.077 |
| 196 | Q | I | -3.439 |
| 196 | Q | K | -4.441 |
| 196 | Q | L | -0.527 |
| 196 | Q | M | -0.674 |
| 196 | Q | N | -1.988 |
| 196 | Q | P | -1.486 |
| 196 | Q | R | -3.247 |
| 196 | Q | S | -0.413 |
| 196 | Q | T | -1.540 |
| 196 | Q | V | -1.813 |
| 196 | Q | W | -1.259 |
| 196 | Q | Y | -1.252 |
| 197 | A | P | -1.581 |
| 197 | A | S | -1.464 |
| 204 | H | K | -2.381 |
| 204 | H | P | -2.488 |

Figure 38 (cont)

| pos | wt | mut | E(PDA) |
|---|---|---|---|
| 204 | H | Q | -0.003 |
| 204 | H | R | -1.011 |
| 206 | E | A | -0.361 |
| 206 | E | F | -0.017 |
| 206 | E | H | -1.390 |
| 206 | E | I | -0.951 |
| 206 | E | K | -0.232 |
| 206 | E | L | -0.651 |
| 206 | E | N | -0.472 |
| 206 | E | Q | -0.550 |
| 206 | E | R | -0.367 |
| 206 | E | S | -1.457 |
| 206 | E | T | -1.874 |
| 206 | E | V | -2.571 |
| 206 | E | Y | -0.020 |
| 207 | V | P | -1.097 |
| 207 | V | Q | -0.195 |
| 209 | D | S | -0.442 |
| 209 | D | T | -1.425 |
| 210 | Q | E | -0.373 |
| 214 | Q | E | -0.671 |
| 215 | V | P | -0.003 |
| 216 | Y | F | -0.810 |
| 216 | Y | H | -0.655 |
| 219 | G | A | -0.431 |
| 219 | G | F | -1.257 |
| 219 | G | H | -1.851 |
| 219 | G | N | -0.700 |
| 219 | G | P | -3.317 |
| 219 | G | S | -2.278 |
| 219 | G | T | -0.435 |
| 219 | G | W | -0.107 |
| 219 | G | Y | -0.728 |
| 220 | E | D | -0.063 |
| 220 | E | N | -0.592 |
| 220 | E | Q | -0.175 |
| 220 | E | S | -1.560 |
| 220 | E | T | -1.221 |
| 221 | R | H | -0.914 |
| 221 | R | S | -0.002 |
| 222 | N | H | -0.271 |
| 223 | G | P | -0.338 |
| 224 | L | A | -0.361 |
| 224 | L | D | -1.704 |
| 224 | L | E | -1.747 |
| 224 | L | G | -0.520 |
| 224 | L | H | -1.425 |
| 224 | L | I | -0.576 |
| 224 | L | K | -1.451 |
| 224 | L | M | -0.443 |
| 224 | L | N | -2.049 |

| Figure 38 (cont) | | | |
|---|---|---|---|
| pos | wt | mut | E(PDA) |
| 224 | L | P | -0.877 |
| 224 | L | Q | -2.211 |
| 224 | L | R | -2.058 |
| 224 | L | S | -2.000 |
| 224 | L | T | -1.523 |
| 224 | L | V | -0.920 |
| 225 | Y | A | -0.522 |
| 225 | Y | D | -0.937 |
| 225 | Y | E | -0.058 |
| 225 | Y | G | -2.237 |
| 225 | Y | H | -0.543 |
| 225 | Y | K | -0.016 |
| 225 | Y | L | -0.176 |
| 225 | Y | M | -0.448 |
| 225 | Y | N | -1.018 |
| 225 | Y | P | -2.214 |
| 225 | Y | Q | -0.526 |
| 225 | Y | S | -1.871 |
| 225 | Y | T | -1.465 |
| 225 | Y | V | -0.832 |
| 226 | A | F | -0.249 |
| 226 | A | G | -2.330 |
| 226 | A | H | -1.873 |
| 226 | A | K | -1.165 |
| 226 | A | M | -1.032 |
| 226 | A | N | -1.102 |
| 226 | A | Q | -0.063 |
| 226 | A | R | -1.715 |
| 226 | A | S | -1.848 |

| Figure 38 (cont) | | | |
|---|---|---|---|
| pos | wt | mut | E(PDA) |
| 226 | A | T | -0.744 |
| 226 | A | Y | -0.991 |
| 227 | D | A | -0.027 |
| 227 | D | E | -0.313 |
| 227 | D | H | -1.260 |
| 227 | D | K | -1.520 |
| 227 | D | L | -0.307 |
| 227 | D | M | -0.818 |
| 227 | D | N | -0.711 |
| 227 | D | Q | -1.657 |
| 227 | D | R | -2.146 |
| 227 | D | S | -0.595 |
| 227 | D | T | -0.672 |
| 227 | D | V | -0.333 |
| 227 | D | Y | -0.330 |
| 228 | N | A | -0.861 |
| 228 | N | F | -1.297 |
| 228 | N | G | -3.512 |
| 228 | N | H | -1.674 |
| 228 | N | S | -3.419 |
| 228 | N | T | -1.557 |
| 229 | D | F | -0.223 |
| 229 | D | G | -1.919 |
| 229 | D | H | -1.863 |
| 229 | D | K | -2.003 |
| 229 | D | L | -0.192 |
| 229 | D | M | -0.047 |
| 229 | D | N | -1.512 |
| 229 | D | Q | -1.432 |

| Figure 38 (cont) | | | |
|---|---|---|---|
| pos | wt | mut | E(PDA) |
| 229 | D | R | -2.683 |
| 229 | D | S | -1.031 |
| 229 | D | T | -0.920 |
| 229 | D | W | -0.506 |
| 229 | D | Y | -0.401 |
| 230 | N | H | -2.481 |
| 230 | N | I | -0.575 |
| 230 | N | K | -1.568 |
| 230 | N | T | -0.637 |
| 230 | N | V | -0.603 |
| 232 | S | T | -0.645 |
| 232 | S | V | -0.797 |
| 233 | T | V | -0.147 |
| 239 | L | V | -0.763 |
| 241 | H | F | -0.089 |
| 241 | H | P | -1.400 |
| 241 | H | Y | -0.723 |
| 242 | D | K | -0.157 |
| 243 | T | K | -0.556 |
| 243 | T | N | -0.102 |
| 243 | T | Q | -0.232 |
| 243 | T | R | -1.348 |
| 243 | T | S | -0.552 |
| 244 | N | G | -0.756 |
| 244 | N | K | -0.172 |
| 244 | N | Q | -1.193 |
| 244 | N | R | -0.490 |

Figure 39. Hydrophobic Surface Patches in Adiponectin

| **Figure 39a – Y122**<br>Mean RHD for WT patch = 0.380<br>Mean RHD for Y122 patch = 0.359 | | |
|---|---|---|
| Residue # | WT Amino Acid | RHD |
| 120 | GLU | -0.254 |
| 121 | THR | 0.412 |
| 122 | TYR | 1.083 |
| 123 | VAL | 0.789 |
| 124 | THR | 0.897 |
| 125 | ILE | 1.165 |
| 128 | MET | 0.824 |
| 129 | PRO | 0.319 |
| 131 | ARG | 0.099 |
| 133 | THR | 0.482 |
| 134 | LYS | 0.115 |

| **Figure 39a – Y122**<br>Mean RHD for WT patch = 0.380<br>Mean RHD for Y122 patch = 0.359 | | |
|---|---|---|
| Residue # | WT Amino Acid | RHD |
| 144 | ASP | -0.329 |
| 146 | SER | -0.241 |
| 147 | THR | -0.251 |
| 165 | THR | 0.149 |
| 167 | TYR | 0.466 |
| 214 | GLN | 0.448 |
| 225 | TYR | 0.917 |
| 228 | ASN | 0.135 |

Figure 39b – I125
Mean RHD for patch = 0.237
Mean RHD for I125 patch = 0.212

| Residue # | WT Amino Acid | RHD |
|---|---|---|
| 120 | GLU | -0.254 |
| 121 | THR | 0.412 |
| 122 | TYR | 1.083 |
| 123 | VAL | 0.789 |
| 124 | THR | 0.897 |
| 125 | ILE | 1.165 |
| 128 | MET | 0.824 |
| 129 | PRO | 0.319 |
| 131 | ARG | 0.099 |
| 133 | THR | 0.482 |
| 167 | THR | 0.466 |
| 214 | GLN | 0.448 |
| 216 | TYR | 0.276 |
| 217 | GLY | -0.426 |
| 218 | ASP | -1.213 |
| 219 | GLY | -0.584 |
| 220 | GLU | -1.066 |
| 221 | ARG | -1.265 |
| 222 | ASN | -0.328 |
| 223 | GLY | 0.510 |
| 224 | LEU | 1.658 |
| 225 | TYR | 0.917 |

Figure 39c – F184
Mean RHD for WT patch = -0.098
Mean RHD for F184 patch = -0.123

| Residue # | WT Amino Acid | RHD |
|---|---|---|
| 120 | GLU | -0.254 |
| 134 | LYS | 0.115 |
| 136 | PHE | 0.481 |
| 170 | ASP | -0.833 |
| 172 | LYS | -0.374 |
| 174 | SER | 0.426 |
| 176 | PHE | 0.181 |
| 180 | LYS | -0.856 |
| 182 | MET | -0.099 |
| 186 | TYR | -0.421 |
| 214 | GLN | 0.448 |
| 216 | TYR | 0.276 |
| 227 | ASP | -0.347 |
| 229 | ASP | -0.430 |
| 231 | ASP | 0.025 |

Figure 39d - V207
Mean RHD for patch = 0.117
Mean RHD for V207 patch = 0.060

| Residue # | WT Amino Acid | RHD |
|---|---|---|
| 109 | TYR | 1.208 |
| 111 | TYR | 0.964 |
| 142 | HIS | -0.032 |
| 151 | HIS | -0.191 |
| 153 | ASN | 0.103 |
| 154 | ILE | 0.716 |
| 155 | PRO | 0.353 |
| 178 | LYS | -0.997 |
| 204 | HIS | -0.152 |
| 206 | GLU | -0.224 |
| 207 | VAL | 0.505 |
| 208 | GLY | -0.047 |
| 209 | ASP | -0.509 |
| 210 | GLN | -0.350 |
| 241 | HIS | 0.511 |
| 242 | ASP | -0.024 |
| 243 | THR | 0.091 |
| 244 | ASN | 0.152 |

Figure 40. Mean RHD values for identified surface patches containing favorable variants.

| **Patch 1 – TYR 122** | | **Patch 2 – ILE 125** | | **Patch 3 – PHE 184** | | **Patch 4 – VAL 207** | |
|---|---|---|---|---|---|---|---|
| Mutation | Mean RHD | Mutation | Mean RHD | Mutation | Mean RHD | Mutation | Mean RHD |
| T121D | 0.357 | T121R | 0.209 | F136R | -0.135 | Y109D | 0.038 |
| T121K | 0.353 | Y122E | 0.197 | S174R | -0.137 | Y109E | 0.051 |
| T121R | 0.348 | Y122K | 0.190 | F176R | -0.127 | Y109K | 0.042 |
| Y122E | 0.335 | Y122N | 0.203 | M182D | -0.122 | Y109N | 0.049 |
| Y122H | 0.359 | Y122R | 0.184 | M182E | -0.130 | Y109R | 0.032 |
| Y122K | 0.326 | Y122Q | 0.211 | M182K | -0.129 | V207D | 0.056 |
| Y122N | 0.341 | T124D | 0.208 | M182R | -0.133 | V207E* | 0.060 |
| Y122Q | 0.350 | T124K | 0.205 | F184D | -0.137 | V207K | 0.053 |
| Y122R | 0.319 | T124R | 0.207 | F184E | -0.138 | V207R | 0.051 |
| T124D | 0.347 | I125D | 0.194 | F184H | -0.123 | T243K | 0.054 |
| T124E | 0.354 | I125E | 0.188 | F184K | -0.145 | T243R | 0.054 |
| T124K | 0.344 | I125H | 0.209 | F184N | -0.134 | | |
| T124N | 0.355 | I125K | 0.175 | F184Q | -0.131 | | |
| T124R | 0.346 | I125N | 0.197 | F184R | -0.146 | | |
| I125A | 0.354 | I125Q | 0.194 | F184S | -0.127 | | |
| I125D | 0.331 | I125R | 0.175 | Y216D | -0.143 | | |
| I125E | 0.324 | I125S | 0.210 | Y216E | -0.137 | | |
| I125G | 0.350 | I125T | 0.212 | Y216G | -0.123 | | |
| I125H | 0.348 | M128D | 0.209 | Y216K | -0.124 | | |
| I125K | 0.308 | M128E | 0.201 | Y216N | -0.125 | | |
| I125N | 0.335 | M128K | 0.188 | Y216R | -0.138 | | |
| I125Q | 0.331 | M128R | 0.184 | Y216S | -0.123 | | |
| I125R | 0.308 | P129R | 0.209 | | | | |
| I125S | 0.349 | T133D | 0.206 | | | | |
| I125T | 0.352 | T133E | 0.207 | | | | |
| I125Y | 0.355 | T133K | 0.199 | | | | |
| M128D | 0.348 | T133N | 0.212 | | | | |
| M128E | 0.339 | T133R | 0.201 | | | | |
| M128K | 0.324 | Y216R | 0.207 | | | | |
| M128N | 0.342 | G223D | 0.191 | | | | |
| M128Q | 0.345 | G223E | 0.201 | | | | |
| M128R | 0.319 | G223K | 0.188 | | | | |
| P129K | 0.356 | G223N | 0.201 | | | | |
| P129R | 0.348 | G223Q | 0.213 | | | | |
| T133D | 0.345 | G223R | 0.192 | | | | |
| T133E | 0.345 | L224D | 0.126 | | | | |
| T133K | 0.337 | L224E | 0.133 | | | | |
| T133N | 0.352 | L224G | 0.161 | | | | |
| T133R | 0.339 | L224H | 0.169 | | | | |
| S146D | 0.354 | L224K | 0.122 | | | | |
| S146E | 0.356 | L224N | 0.134 | | | | |
| S146K | 0.345 | L224Q | 0.155 | | | | |
| T147K | 0.350 | L224R | 0.121 | | | | |
| T147R | 0.352 | L224S | 0.159 | | | | |
| Y225D | 0.343 | L224T | 0.172 | | | | |
| Y225E | 0.340 | Y225D | 0.205 | | | | |
| Y225K | 0.339 | Y225E | 0.202 | | | | |
| Y225N | 0.350 | Y225K | 0.201 | | | | |
| Y225R | 0.332 | Y225N | 0.210 | | | | |
| | | Y225Q | 0.219 | | | | |
| | | Y225R | 0.195 | | | | |

Figure 41. Energies for identified favorable variants that reduce surface patch hydrophobicity.

| Patch 1 – PHE 122 | | Patch 2 – ILE 125 | | Patch 3 – PHE 184 | | Patch 4 – VAL 207 | |
|---|---|---|---|---|---|---|---|
| Mutation | E | Mutation | E | Mutation | E | Mutation | E |
| T121D | 1.803 | T121R | -0.475 | F136R | 8.051 | Y109D | 1.708 |
| T121K | 0.345 | Y122E | -0.747 | S174R | 0.740 | Y109E | 2.043 |
| T121R | -0.475 | Y122K | 0.362 | F176R | 7.727 | Y109K | 1.812 |
| Y122E | -0.747 | Y122N | -0.750 | M182D | 2.388 | Y109N | 1.657 |
| Y122H* | -0.633 | Y122R | 0.012 | M182E | 0.179 | Y109R | 1.920 |
| Y122K | 0.362 | Y122Q | -0.638 | M182K | 2.731 | V207D | 1.015 |
| Y122N | -0.750 | T124D | 2.315 | M182R | 2.448 | V207E* | 0.179 |
| Y122Q | -0.638 | T124K | 0.273 | F184D | -0.981 | V207K | 0.204 |
| Y122R | 0.012 | T124R | -1.623 | F184E | 0.222 | V207R | 0.303 |
| T124D | 2.315 | I125D | 0.543 | F184H* | -3.242 | T243K | -0.556 |
| T124E | 1.364 | I125E | -1.056 | F184K | -2.925 | T243R | -1.348 |
| T124K | 0.273 | I125H* | 0.251 | F184N | -2.950 | | |
| T124N | 0.618 | I125K | 1.021 | F184Q | -0.906 | | |
| T124R | -1.623 | I125N | 0.230 | F184R | -2.857 | | |
| I125A | 1.160 | I125Q | 0.225 | F184S | -1.537 | | |
| I125D | 0.543 | I125R | 0.570 | Y216D | 3.540 | | |
| I125E | -1.056 | I125S | 0.352 | Y216E | 2.625 | | |
| I125G | 2.003 | I125T | -0.438 | Y216G | 3.713 | | |
| I125H | 0.251 | M128D | -0.410 | Y216K | 2.098 | | |
| I125K | 1.021 | M128E | -1.018 | Y216N | 2.756 | | |
| I125N | 0.230 | M128K | 1.082 | Y216R | 1.958 | | |
| I125Q | 0.225 | M128R | 0.483 | Y216S | 2.770 | | |
| I125R | 0.570 | P129R | 10.919 | | | | |
| I125S | 0.352 | T133D | 0.247 | | | | |
| I125T | -0.438 | T133E | -0.217 | | | | |
| I125Y | 0.462 | T133K | 0.287 | | | | |
| M128D | -0.410 | T133N | -0.309 | | | | |
| M128E | -1.018 | T133R | -0.890 | | | | |
| M128K | 1.082 | Y216R | 1.958 | | | | |
| M128N | -0.583 | G223D | 0.816 | | | | |
| M128Q | -0.726 | G223E | 1.597 | | | | |
| M128R | 0.483 | G223K | 0.990 | | | | |
| P129K | 11.858 | G223N | 0.295 | | | | |
| P129R | 10.919 | G223Q | 0.777 | | | | |
| T133D | 0.247 | G223R | 0.567 | | | | |
| T133E | -0.217 | L224D | -1.704 | | | | |
| T133K | 0.287 | L224E | -1.747 | | | | |
| T133N | -0.309 | L224G | -0.520 | | | | |
| T133R | -0.890 | L224H | -1.425 | | | | |
| S146D | 0.866 | L224K | -1.451 | | | | |
| S146E | 0.573 | L224N | -2.049 | | | | |
| S146K | 1.136 | L224Q | -2.211 | | | | |
| T147K | 2.178 | L224R | -2.058 | | | | |
| T147R | 2.039 | L224S | -2.000 | | | | |
| Y225D | -0.937 | L224T | -1.523 | | | | |
| Y225E | -0.058 | Y225D | -0.937 | | | | |
| Y225K | -0.016 | Y225E | -0.058 | | | | |
| Y225N | -1.018 | Y225K | -0.016 | | | | |
| Y225R | 0.249 | Y225N | -1.018 | | | | |
| | | Y225Q | -0.526 | | | | |
| | | Y225R | 0.249 | | | | |

Figure 42 – Graph showing gAd Variants Inhibit cAMP-induced Lipolysis in Primary Human Adipocytes.
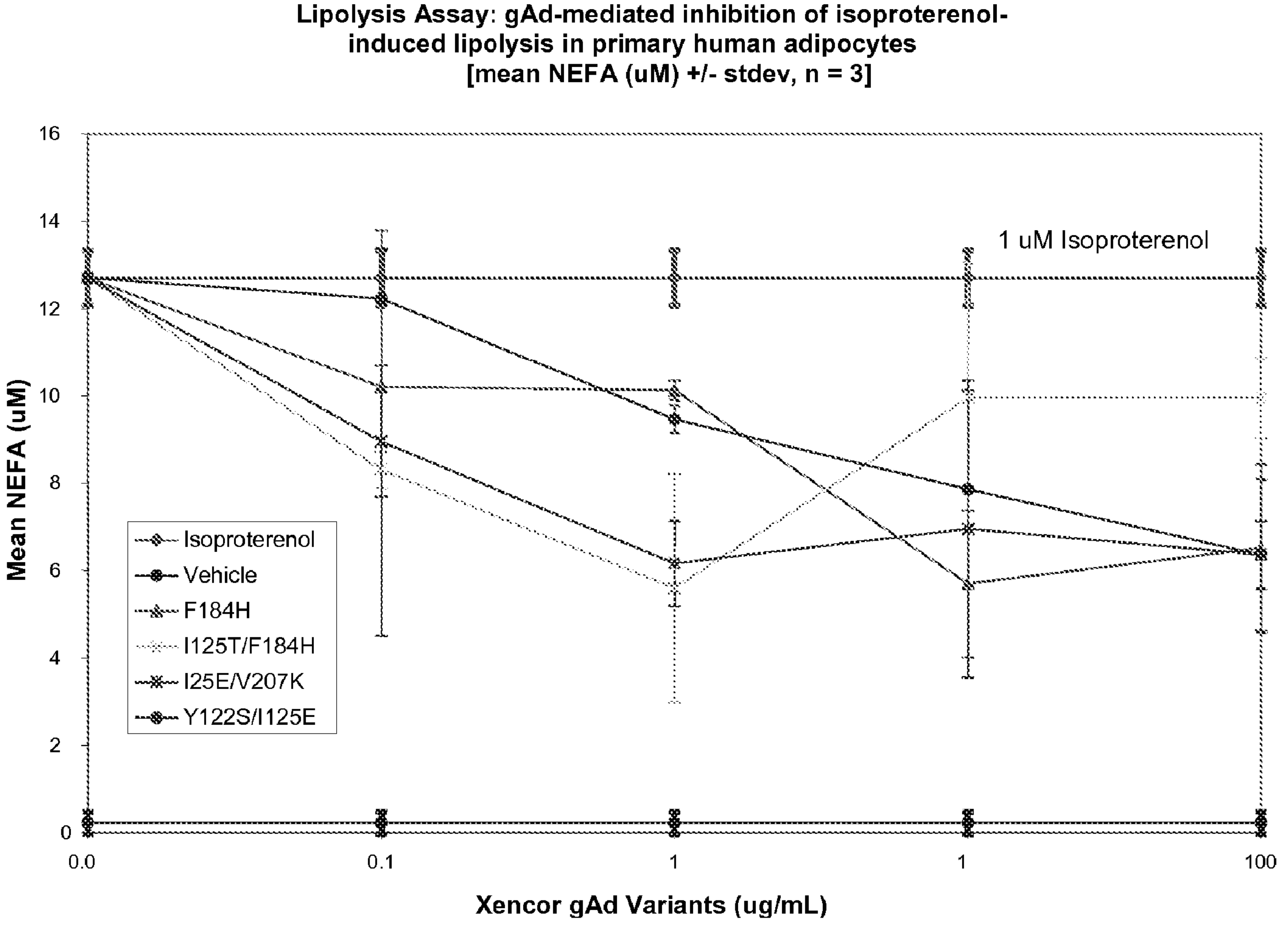

Figure 43 – Graph Showing Glucose Uptake in Primary Human Adipocytes
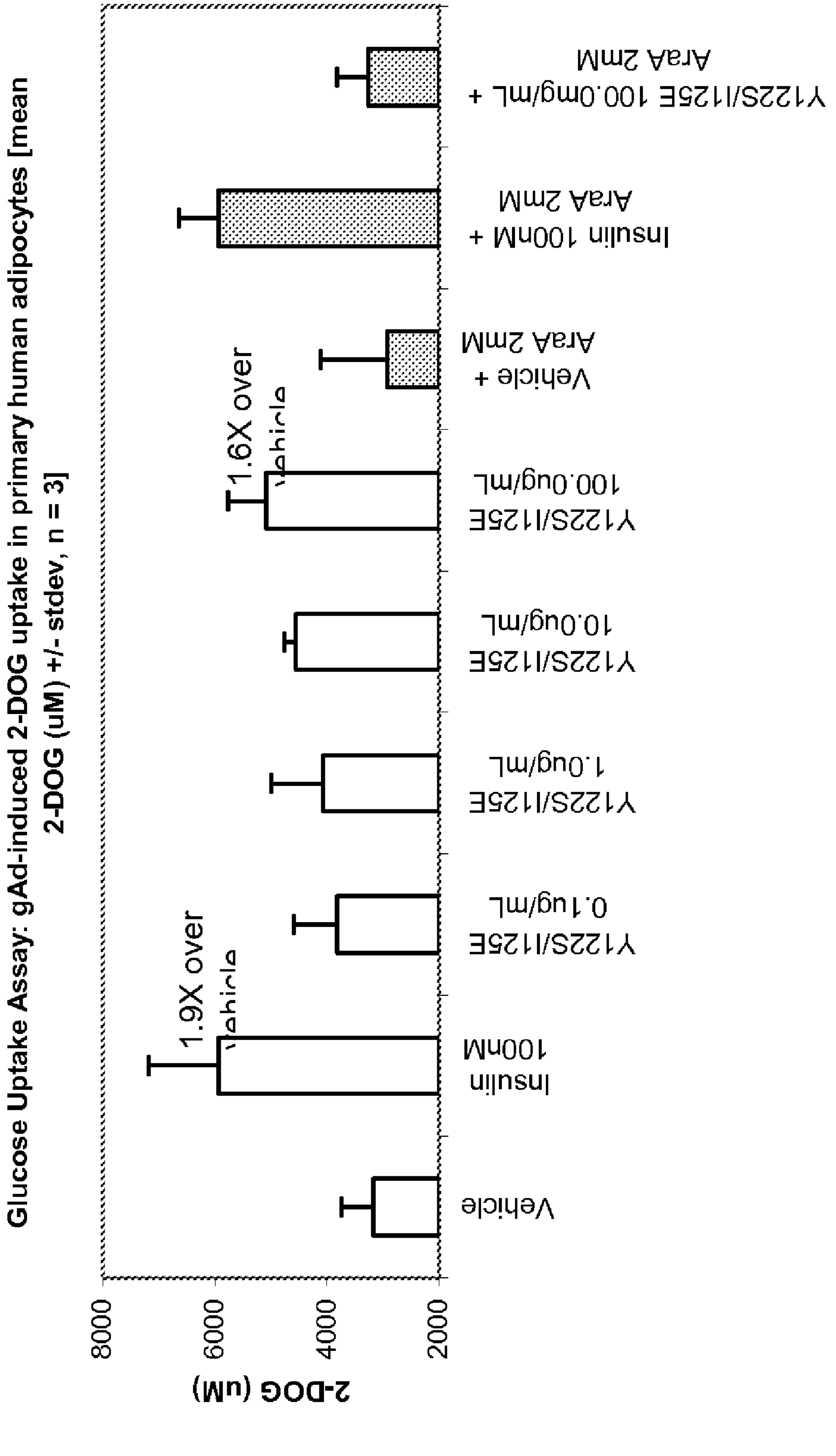

Figure 44 – Time Course of Y122S/I125E-induced AMPK and ACC Phosphorylation
L6 myotubes:
<u>Expt. 1</u>
| Lanes | | |
|---|---|---|
| | 1 | Control |
| | 2-3 | 1 mM AICAR, 30 min |
| | 4-5 | 100 ug/ml #3962, 5 min |
| | 6-7 | 100 ug/ml #3962, 10 min |
| | 8-9 | 100 ug/ml #3962, 15 min |
L6 myotubes day 4
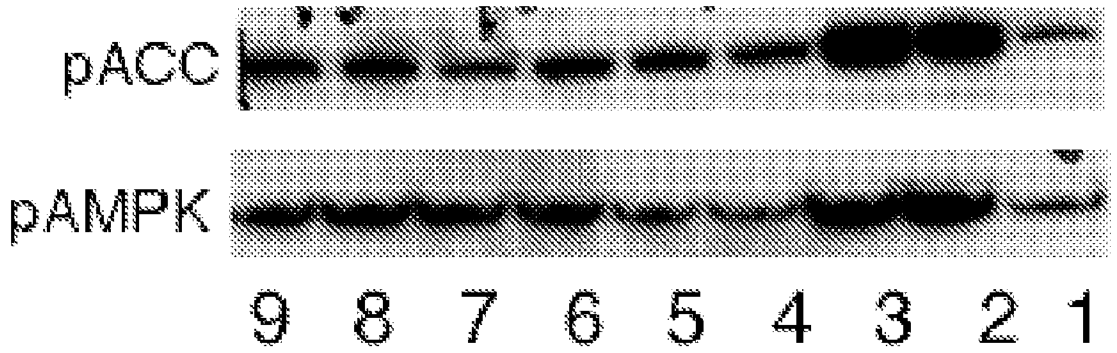

Figure 45 – Dose Response of Y122S/I125E-induced AMPK Phosphorylation in L6 Myotubes
Expt 2.
| Lanes | | |
|---|---|---|
| | 1-2 | Control |
| | 3-4 | 1 mM AICAR, 30 min |
| | 5-6 | 10 ug/ml #3962, 15 min |
| | 7-8 | 50 ug/ml #3962, 15 min |
| | 9-10 | 100 ug/ml #3962, 15 min |
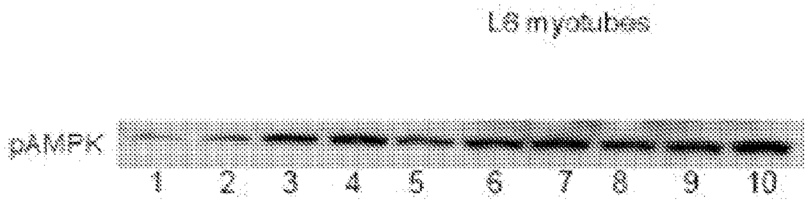
Figure 46 - AMP Kinase Assay using SAMS Peptide Substrate
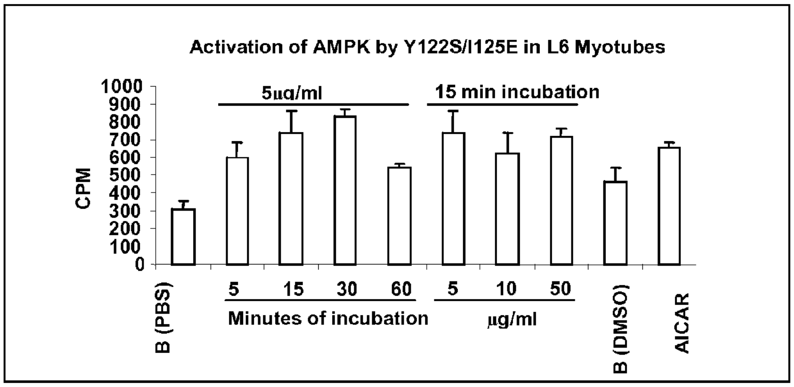
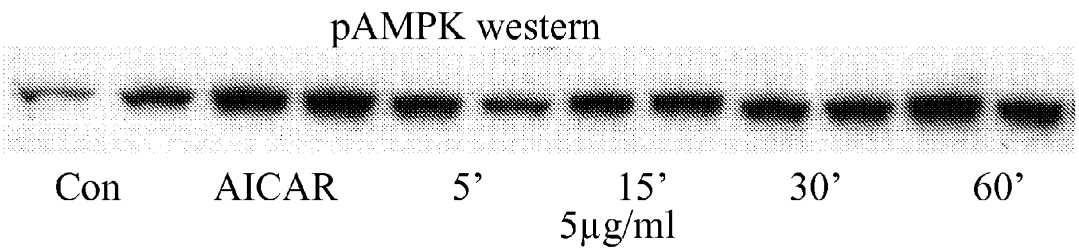

Figure 47 - Effects of Y122S/I125E on Palmitate Oxidation in L6 Myotubes
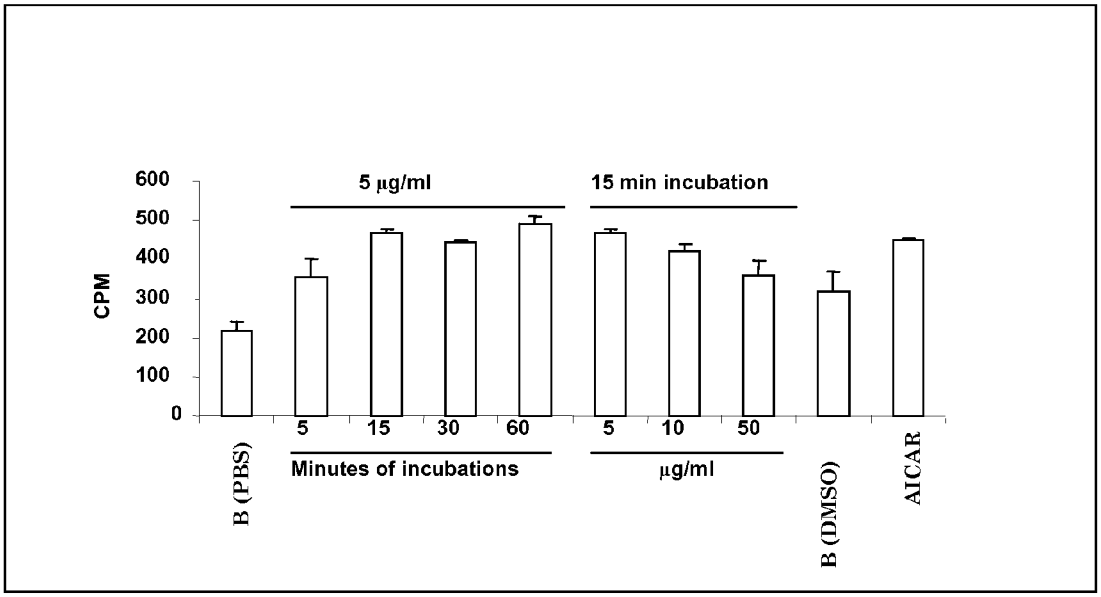
Figure 48 –Y122S/I125E Stimulation of Glucose Uptake in L6 Myotubes
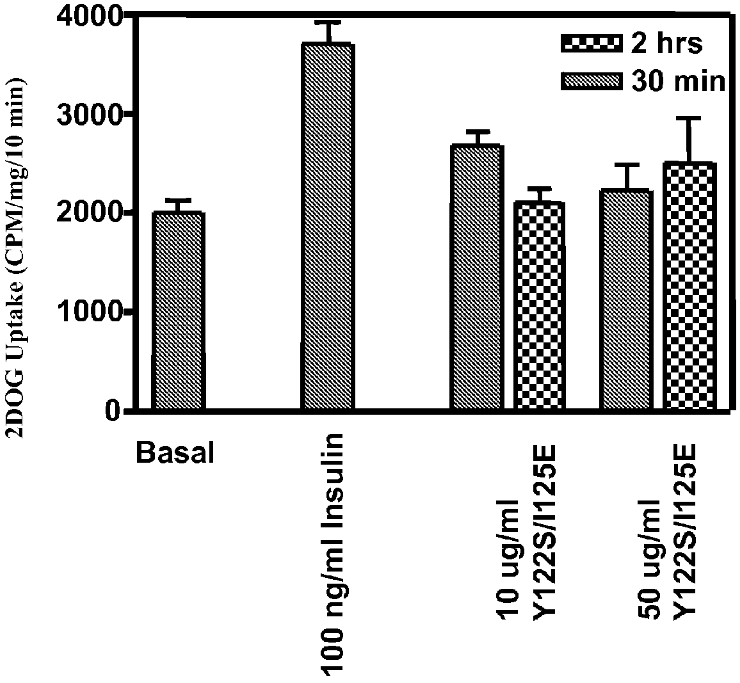

Figure 49 – Y122S/I125E PK after Single Dose IV, IP, and SC at 1mg/kg
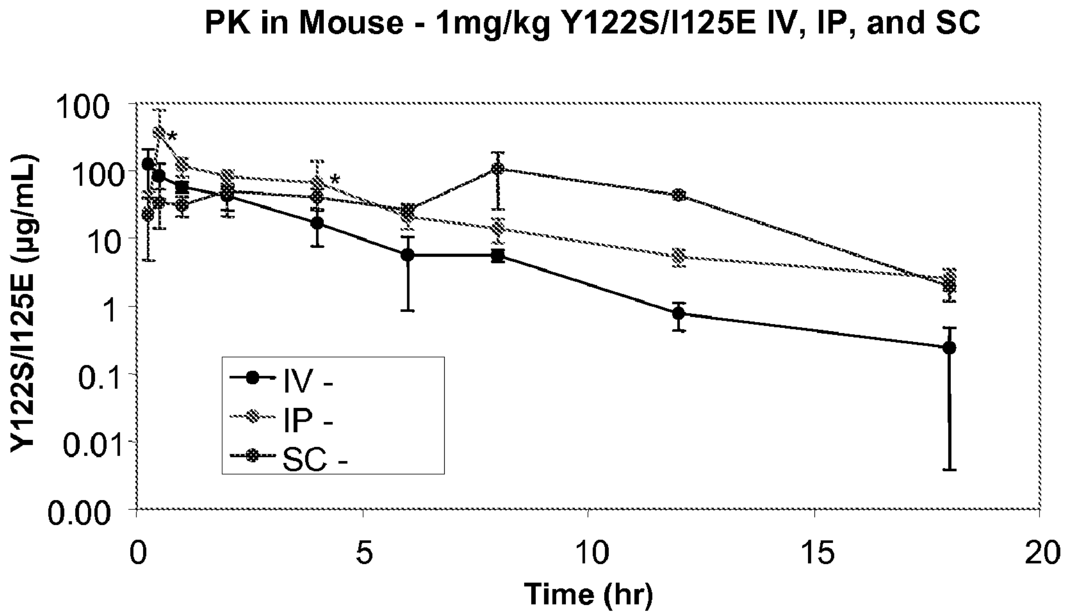
Figure 50 - Y122S/I125E PK after Single Dose IV, IP, and SC at 6mg/kg
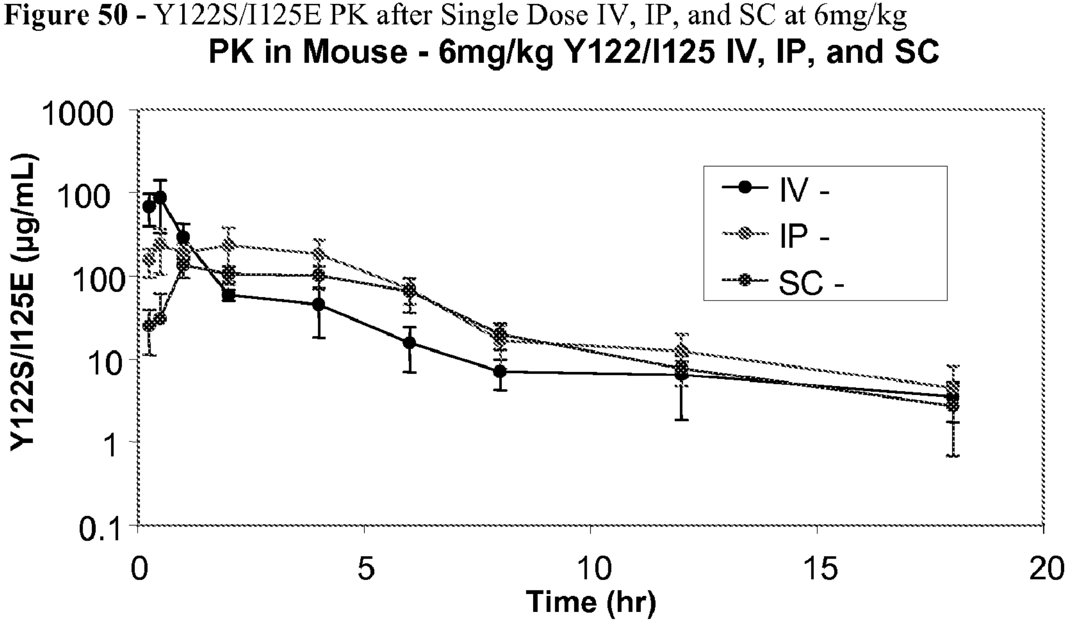

Figure 51 – Table of Noncompartmental Modeling Analysis to Derive Pharmacokinetic Parameters.

| Parameter | Units | 1mg/kg - IV | 6mg/kg - IV | 1mg/kg - IP | 6mg/kg - IP | 1mg/kg - SC | 6mg/kg - SC |
|---|---|---|---|---|---|---|---|
| Terminal half-life | Hr | 2.1 | 3.9 | 3.2 | 2.8 | 3.4 | 2.6 |
| Cmax | μg/mL | 125.2 | 684 | 110 | 238.3 | 107.3 | 134.7 |
| AUC INF | Hr * μg/mL | 261.1 | 1097.1 | 618.4 | 1266.5 | 804.0 | 726.6 |
| Vi | mL/kg | 8 | 8.8 | N/d | N/d | N/d | N/d |
| Clearance | mL/hr/kg | 3.8 | 5.5 | N/d | N/d | N/d | N/d |
| Vss | mL/kg | 8.9 | 11.7 | N/d | N/d | N/d | N/d |
| F | | N/d | N/d | N/d | N/d | **~100%** | **66.2%** |

Figure 52 - Fed State Glucose Measurements (SC, qd, 19 days of treatment; 9 male db/db per group, mean +/- SEM)

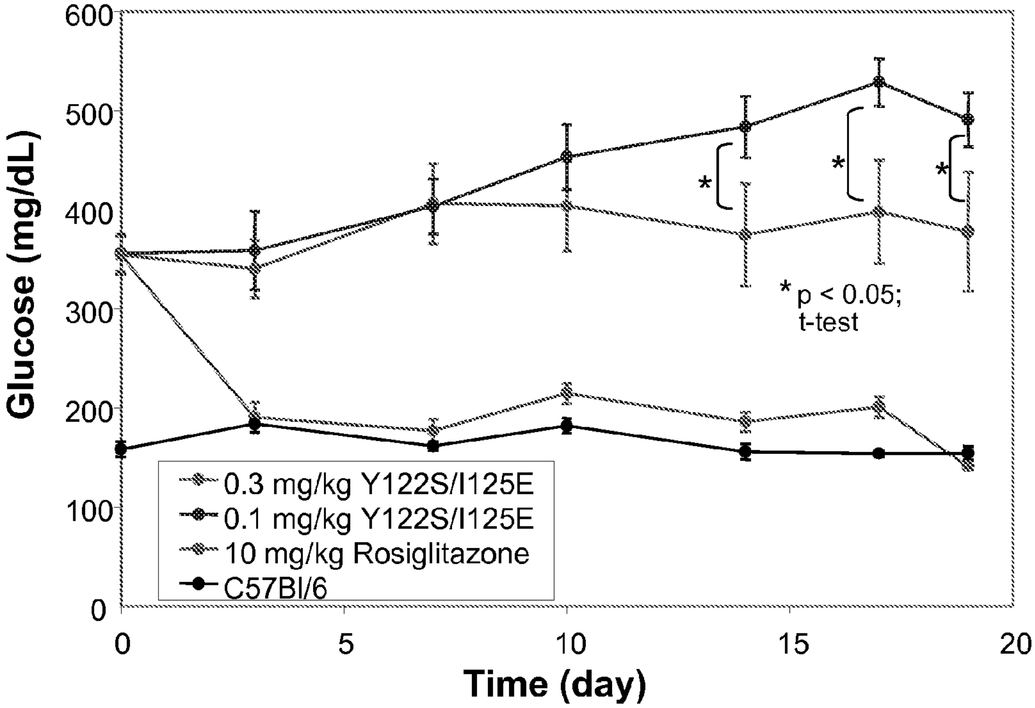

Figure 53 – Weight Measurements (SC, qd, 19 days of treatment; 9 male db/db per group, mean +/- SEM)
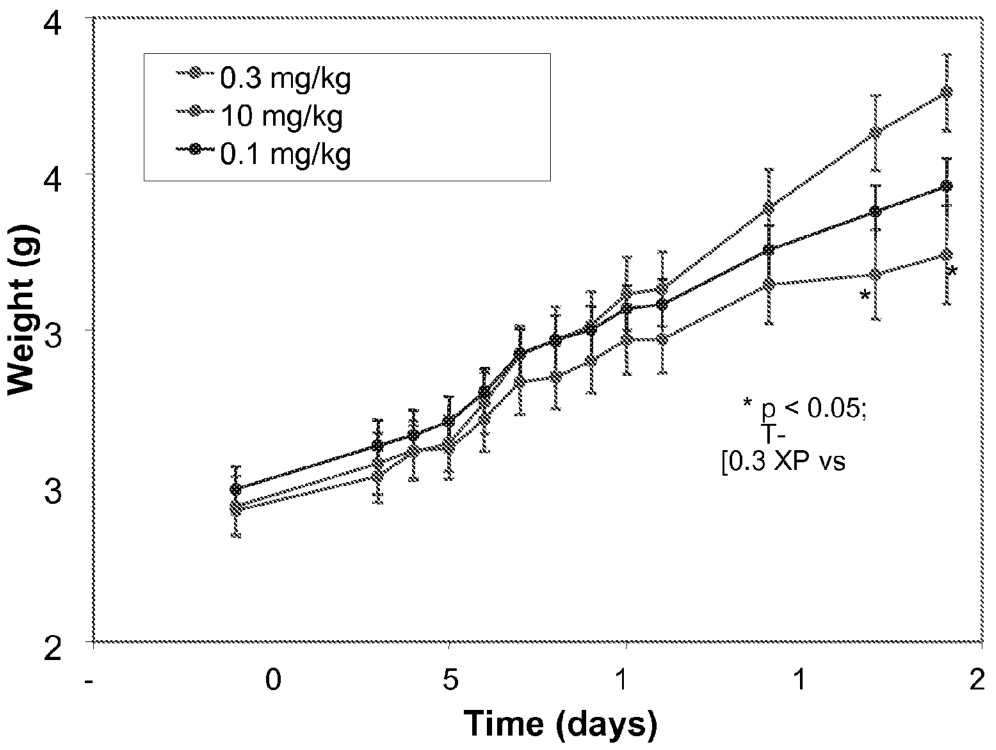

Figure 54 – IP-GTT Before and After Treatment with Y122S/I125E
Figure 54A IP-GTT At Study Initiation (SC, qd, 20 days of treatment; 9 male db/db per group, mean +/- SEM)
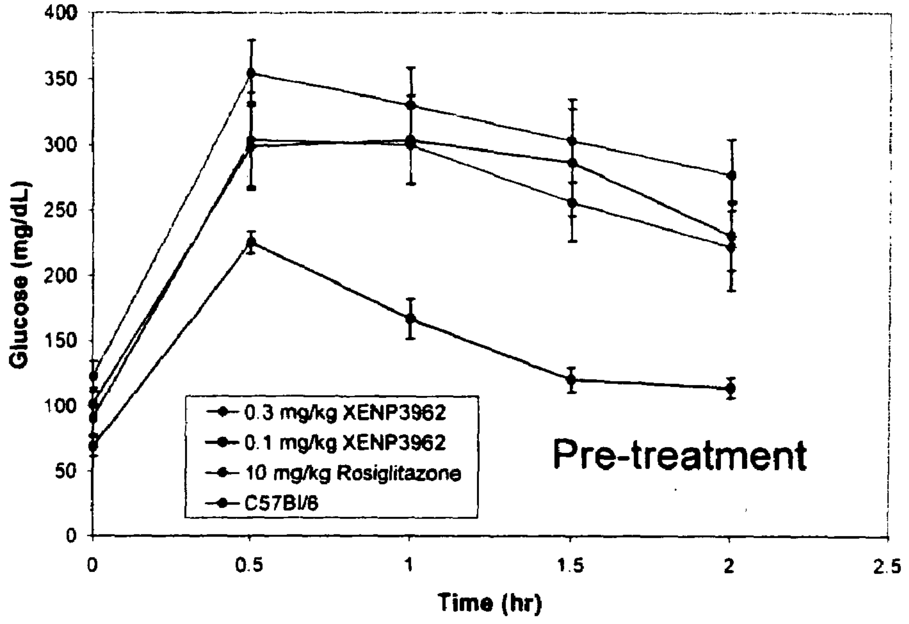
Figure 54B IP-GTT At Study Termination (SC, qd, 20 days of treatment; 9 male db/db per group, mean +/- SEM)
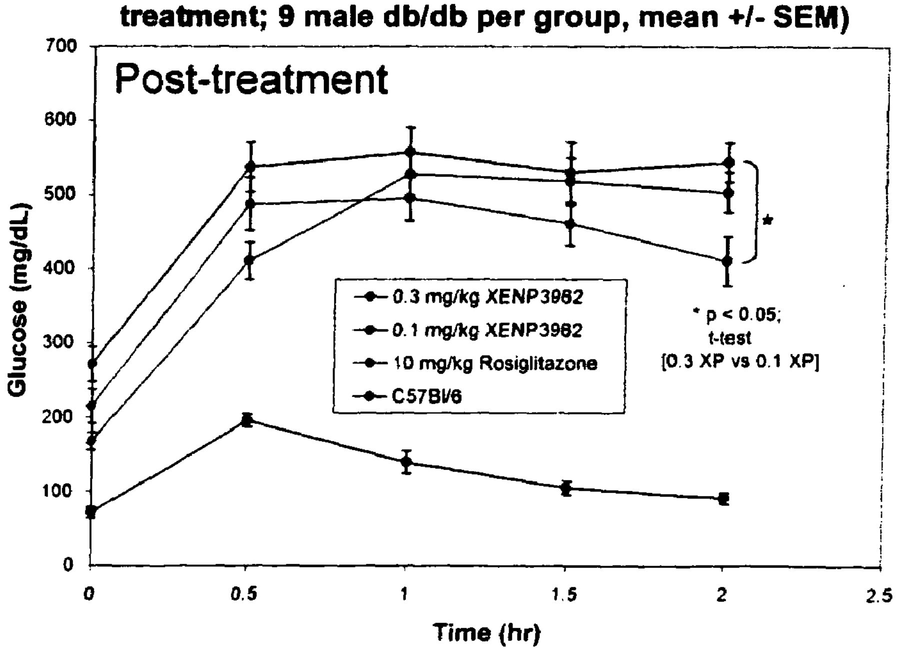

Figure 55 – Effect of gAd Y122S/I125E on Phosphorylation of AMPK, ACC and NOS in Arota and Myocardium Cells
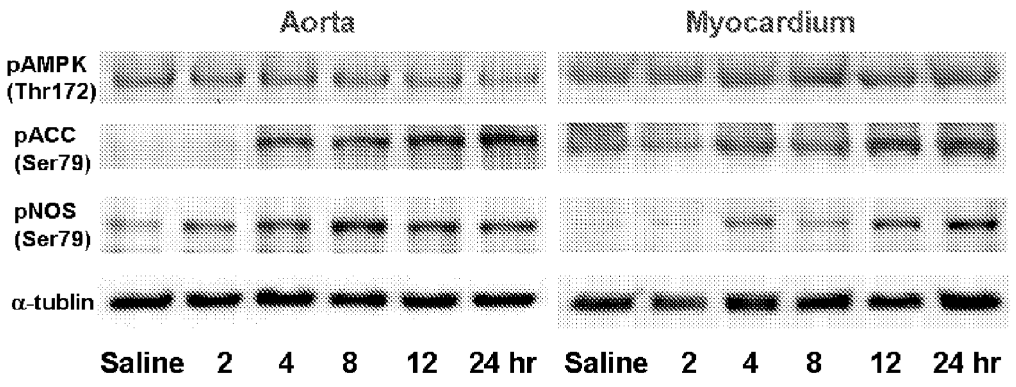

SEQUENCE LISTING

```
<160> NUMBER OF SEQ ID NOS: 8

<210> SEQ ID NO 1
<211> LENGTH: 244
<212> TYPE: PRT
<213> ORGANISM: Artificial Sequence
<220> FEATURE:
<223> OTHER INFORMATION: Variants of human adiponectin
<220> FEATURE:
<221> NAME/KEY: MISC_FEATURE
<222> LOCATION: (109)..(109)
<223> OTHER INFORMATION: X at 109 can be either amino acid D, E, H, K,
      N, Q, R, or Y
<220> FEATURE:
<221> NAME/KEY: MISC_FEATURE
<222> LOCATION: (110)..(110)
<223> OTHER INFORMATION: X at 110 can be either amino acid D, E, H, K,
      N, Q, R, S, or V
<220> FEATURE:
<221> NAME/KEY: MISC_FEATURE
<222> LOCATION: (111)..(111)
<223> OTHER INFORMATION: X at 111 can be either amino acid D, E, K, N,
      Q, R, Y, or H
<220> FEATURE:
<221> NAME/KEY: MISC_FEATURE
<222> LOCATION: (122)..(122)
<223> OTHER INFORMATION: X at 122 can be either amino acid D, E, H, N,
      R, S, or Y
<220> FEATURE:
<221> NAME/KEY: MISC_FEATURE
<222> LOCATION: (125)..(125)
<223> OTHER INFORMATION: X at 125 can be either amino acid D, E, H, K,
      N, Q, R, S, T, or I
<220> FEATURE:
<221> NAME/KEY: MISC_FEATURE
<222> LOCATION: (128)..(128)
<223> OTHER INFORMATION: X at 128 can be either amino acid A, D, E, H,
      K, N, Q, R, S, T,
      or M
<220> FEATURE:
<221> NAME/KEY: MISC_FEATURE
<222> LOCATION: (135)..(135)
<223> OTHER INFORMATION: X at 135 can be either amino acid D, E, H, K,
```

-continued

```
      N, Q, R, or I
<220> FEATURE:
<221> NAME/KEY: MISC_FEATURE
<222> LOCATION: (152)..(152)
<223> OTHER INFORMATION: X at 152 can be either amino acid A, N, S, or C
<220> FEATURE:
<221> NAME/KEY: MISC_FEATURE
<222> LOCATION: (182)..(182)
<223> OTHER INFORMATION: X at 182 can be either amino acid A, D, E, K,
      N, Q, R, S, T, or M
<220> FEATURE:
<221> NAME/KEY: MISC_FEATURE
<222> LOCATION: (184)..(184)
<223> OTHER INFORMATION: X at 184 can be either amino acid D, H, K, N,
      R, or F
<220> FEATURE:
<221> NAME/KEY: MISC_FEATURE
<222> LOCATION: (207)..(207)
<223> OTHER INFORMATION: X at 207 can be either amino acid D, E, H, K,
      N, Q, R, S, or V

<400> SEQUENCE: 1

Met Leu Leu Leu Gly Ala Val Leu Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Xaa Xaa Xaa Arg
            100                 105                 110

Ser Ala Phe Ser Val Gly Leu Glu Thr Xaa Val Thr Xaa Pro Asn Xaa
        115                 120                 125

Pro Ile Arg Phe Thr Lys Xaa Phe Tyr Asn Gln Gln Asn His Tyr Asp
    130                 135                 140

Gly Ser Thr Gly Lys Phe His Xaa Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Xaa Leu Xaa Thr Tyr Asp Gln Tyr Gln Glu Asn
            180                 185                 190

Asn Val Asp Gln Ala Ser Gly Ser Val Leu Leu His Leu Glu Xaa Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn


<210> SEQ ID NO 2
<211> LENGTH: 247
<212> TYPE: PRT
<213> ORGANISM: Mouse

<400> SEQUENCE: 2

Met Leu Leu Leu Gln Ala Leu Leu Phe Leu Leu Ile Leu Pro Ser His
```

-continued

```
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Ser Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
        195                 200                 205

Glu Val Gly Asp Gln Val Trp Leu Gln Val Tyr Gly Asp Gly Asp His
    210                 215                 220

Asn Gly Leu Tyr Ala Asp Asn Val Asn Asp Ser Thr Phe Thr Gly Phe
225                 230                 235                 240

Leu Leu Phe His Asp Thr Asn
                245


<210> SEQ ID NO 3
<211> LENGTH: 244
<212> TYPE: PRT
<213> ORGANISM: Rat

<400> SEQUENCE: 3

Met Leu Leu Leu Gln Ala Leu Leu Phe Leu Leu Ile Leu Pro Ser His
1               5                   10                  15

Glu Gly Ile Thr Ala Thr Glu Gly Pro Gly Ala Leu Val Pro Pro Pro
            20                  25                  30

Lys Glu Thr Cys Ala Gly Trp Met Ala Gly Ile Pro Gly Tyr Pro Gly
        35                  40                  45

His Asn Gly Ile Pro Gly Arg Asp Gly Arg Asp Gly Thr Pro Gly Glu
    50                  55                  60

Lys Gly Glu Lys Gly Asp Ala Gly Val Leu Gly Pro Lys Gly Asp Pro
65                  70                  75                  80

Gly Asp Ala Gly Met Thr Gly Ala Glu Gly Pro Arg Gly Phe Pro Gly
                85                  90                  95

Thr Pro Gly Arg Lys Gly Glu Pro Gly Glu Ala Ala Tyr Met Tyr His
            100                 105                 110

Ser Ala Phe Ser Val Gly Leu Glu Thr Arg Val Thr Val Pro Asn Val
        115                 120                 125
```

-continued

```
Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ser Tyr His Ile Thr Val Tyr Met Lys Asp Val Lys Val Ser Leu Phe
                165                 170                 175

Lys Lys Asp Lys Ala Val Leu Phe Thr Tyr Asp Gln Tyr Gln Glu Lys
            180                 185                 190

Asn Val Asp Gln Ala Ser Gly Ser Met Leu Leu His Leu Glu Val Gly
        195                 200                 205

Asp Gln Val Trp Leu Gln Val Tyr Gly Glu Gly Asp Asn Asn Gly Leu
    210                 215                 220

Tyr Ala Asp Asn Val Asn Asp Ser Thr Phe Thr Gly Phe Leu Leu Tyr
225                 230                 235                 240

His Asp Thr Asn


<210> SEQ ID NO 4
<211> LENGTH: 243
<212> TYPE: PRT
<213> ORGANISM: Macaque

<400> SEQUENCE: 4

Met Leu Leu Gly Ala Val Leu Leu Leu Leu Ala Leu Pro Ser His Gly
1               5                   10                  15

Gln Asp Thr Thr Thr Gln Gly Pro Gly Val Leu Leu Pro Leu Pro Lys
            20                  25                  30

Gly Ala Cys Thr Gly Trp Met Ala Gly Ile Pro Gly His Pro Gly His
        35                  40                  45

Asn Gly Val Pro Gly Arg Asp Gly Arg Asp Gly Thr Pro Gly Glu Lys
    50                  55                  60

Gly Glu Lys Gly Asp Pro Gly Leu Ile Gly Pro Lys Gly Asp Thr Gly
65                  70                  75                  80

Glu Thr Gly Val Thr Gly Ala Glu Gly Pro Arg Gly Phe Pro Gly Ile
                85                  90                  95

Gln Gly Arg Lys Gly Glu Pro Gly Glu Gly Ala Tyr Val Tyr Arg Ser
            100                 105                 110

Ala Phe Ser Val Gly Leu Glu Thr Tyr Val Thr Val Pro Asn Met Pro
        115                 120                 125

Ile Arg Phe Thr Lys Ile Phe Tyr Asn Gln Gln Asn His Tyr Asp Gly
    130                 135                 140

Ser Thr Gly Lys Phe His Cys Asn Ile Pro Gly Leu Tyr Tyr Phe Ala
145                 150                 155                 160

Tyr His Ile Thr Val Tyr Met Lys Asp Val Lys Val Ser Leu Phe Lys
                165                 170                 175

Lys Asp Lys Ala Met Leu Phe Thr Tyr Asp Gln Tyr Gln Glu Asn Asn
            180                 185                 190

Val Asp Gln Ala Ser Gly Ser Val Leu Leu His Leu Glu Val Gly Asp
        195                 200                 205

Gln Val Trp Leu Gln Val Tyr Gly Glu Gly Glu Arg Asn Gly Leu Tyr
    210                 215                 220

Ala Asp Asn Asp Asn Asp Ser Thr Phe Thr Gly Phe Leu Leu Tyr His
225                 230                 235                 240

Asp Thr Asn
```

-continued

<210> SEQ ID NO 5
<211> LENGTH: 244
<212> TYPE: PRT
<213> ORGANISM: Dog

<400> SEQUENCE: 5

```
Met Leu Leu Leu Arg Ala Val Leu Leu Leu Leu Val Leu Pro Ala His
1               5                   10                  15

Gly Gln Asp Ser Val Ala Glu Gly Pro Gly Val Leu Leu Pro Leu Pro
            20                  25                  30

Lys Gly Ala Cys Pro Gly Trp Met Ala Gly Ile Pro Gly His Pro Gly
        35                  40                  45

His Asn Gly Thr Pro Gly Arg Asp Gly Arg Asp Gly Thr Pro Gly Glu
    50                  55                  60

Lys Gly Glu Lys Gly Asp Ala Gly Leu Val Gly Pro Lys Gly Asp Thr
65                  70                  75                  80

Gly Glu Thr Gly Val Thr Gly Val Glu Gly Pro Arg Gly Phe Pro Gly
                85                  90                  95

Thr Pro Cys Arg Lys Gly Glu Pro Gly Glu Ser Ala Tyr Val His Arg
            100                 105                 110

Ser Ala Phe Ser Val Gly Leu Glu Ser Arg Ile Thr Val Pro Asn Val
        115                 120                 125

Pro Ile Arg Phe Thr Lys Ile Phe Tyr Asn Leu Gln Asn His Tyr Asp
    130                 135                 140

Gly Thr Thr Gly Lys Phe His Cys Asn Ile Pro Gly Leu Tyr Tyr Phe
145                 150                 155                 160

Ser Tyr His Ile Thr Val Tyr Leu Lys Asp Val Lys Val Ser Leu Tyr
                165                 170                 175

Lys Lys Asp Lys Ala Met Leu Phe Thr Tyr Asp Gln Tyr Gln Glu Lys
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Asp Gly Asp Ser Tyr Gly Ile
    210                 215                 220

Tyr Ala Asp Asn Val Asn Asp Ser Thr Phe Thr Gly Phe Leu Leu Tyr
225                 230                 235                 240

His Asp Thr Asn
```

<210> SEQ ID NO 6
<211> LENGTH: 243
<212> TYPE: PRT
<213> ORGANISM: Boar

<400> SEQUENCE: 6

```
Met Leu Leu Leu Gly Ala Val Leu Leu Leu Leu Ala Leu Pro Ser Leu
1               5                   10                  15

Gly Gln Glu Thr Thr Glu Lys Pro Gly Ala Leu Leu Pro Met Pro Lys
            20                  25                  30

Gly Ala Cys Ala Gly Trp Met Ala Gly Ile Pro Gly His Pro Gly His
        35                  40                  45

Asn Gly Thr Pro Gly Arg Asp Gly Arg Asp Gly Val Pro Gly Glu Lys
    50                  55                  60

Gly Glu Lys Gly Asp Thr Gly Leu Thr Gly Pro Lys Gly Asp Thr Gly
65                  70                  75                  80

Glu Ser Gly Val Thr Gly Val Glu Gly Pro Arg Gly Phe Pro Gly Ile
                85                  90                  95
```

-continued

```
Pro Gly Arg Lys Gly Glu Pro Gly Glu Ser Ala Tyr Val Tyr Arg Ser
            100                 105                 110

Ala Phe Ser Val Gly Leu Glu Thr Arg Val Thr Val Pro Asn Met Pro
        115                 120                 125

Ile Arg Phe Thr Lys Ile Phe Tyr Asn Gln Gln Asn His Tyr Asp Val
    130                 135                 140

Thr Thr Gly Lys Phe His Cys Asn Ile Pro Gly Leu Tyr Tyr Phe Ser
145                 150                 155                 160

Phe His Ile Thr Val Tyr Leu Lys Asp Val Lys Val Ser Leu Tyr Lys
                165                 170                 175

Lys Asp Lys Ala Val Leu Phe Thr Tyr Asp Gln Tyr Gln Asp Lys Asn
            180                 185                 190

Val Asp Gln Ala Ser Gly Ser Val Leu Leu Tyr Leu Glu Lys Gly Asp
        195                 200                 205

Gln Val Trp Leu Gln Ala Tyr Gly Asp Glu Glu Asn Asn Gly Val Tyr
    210                 215                 220

Ala Asp Asn Val Asn Asp Ser Ile Phe Thr Gly Phe Leu Leu Tyr His
225                 230                 235                 240

Asn Ile Glu


<210> SEQ ID NO 7
<211> LENGTH: 240
<212> TYPE: PRT
<213> ORGANISM: Cow

<400> SEQUENCE: 7

Met Leu Leu Gln Gly Ala Leu Leu Leu Leu Leu Ala Leu Pro Ser His
1               5                   10                  15

Gly Glu Asp Asn Met Glu Asp Pro Pro Leu Pro Lys Gly Ala Cys Ala
            20                  25                  30

Gly Trp Met Ala Gly Ile Pro Gly His Pro Gly His Asn Gly Thr Pro
        35                  40                  45

Gly Arg Asp Gly Arg Asp Gly Thr Pro Gly Glu Lys Gly Glu Lys Gly
    50                  55                  60

Asp Ala Gly Leu Leu Gly Pro Lys Gly Glu Thr Gly Asp Val Gly Met
65                  70                  75                  80

Thr Gly Ala Glu Gly Pro Arg Gly Phe Pro Gly Thr Pro Gly Arg Lys
                85                  90                  95

Gly Glu Pro Gly Glu Ala Ala Tyr Val Tyr Arg Ser Ala Phe Ser Val
            100                 105                 110

Gly Leu Glu Thr Arg Val Thr Val Pro Asn Val Pro Ile Arg Phe Thr
        115                 120                 125

Lys Ile Phe Tyr Asn Gln Gln Asn His Tyr Asp Gly Ser Thr Gly Lys
    130                 135                 140

Phe Tyr Cys Asn Ile Pro Gly Leu Tyr Tyr Phe Ser Tyr His Ile Thr
145                 150                 155                 160

Val Tyr Met Lys Asp Val Lys Val Ser Leu Phe Lys Lys Asp Lys Ala
                165                 170                 175

Val Leu Phe Thr Tyr Asp Gln Tyr Gln Glu Lys Asn Val Asp Gln Ala
            180                 185                 190

Ser Gly Ser Val Leu Leu His Leu Glu Val Gly Asp Gln Val Trp Leu
        195                 200                 205

Gln Val Tyr Glu Gly Glu Asn His Asn Gly Val Tyr Ala Asp Asn Val
    210                 215                 220
```

-continued

```
Asn Asp Ser Thr Phe Thr Gly Phe Leu Leu Tyr His Asn Ile Val Glu
225                 230                 235                 240


<210> SEQ ID NO 8
<211> LENGTH: 244
<212> TYPE: PRT
<213> ORGANISM: Chicken

<400> SEQUENCE: 8

Met Arg Gly Ser Val Gly Phe Leu Leu Cys Ser Leu Leu Leu Ala Leu
1               5                   10                  15

Ser Gly Thr Glu Met Ala Asp Gln Ala Asp Gln Ser Asp Pro Lys Met
            20                  25                  30

Ser Cys Ala Asn Trp Met Gly Gly Ala Pro Gly His Pro Gly His Asn
        35                  40                  45

Gly Leu Pro Gly Arg Asp Gly Lys Asp Gly Lys Asp Gly Gln Lys Gly
    50                  55                  60

Asp Lys Gly Glu Pro Gly Leu Gln Gly Val Lys Gly Asp Thr Gly Glu
65                  70                  75                  80

Lys Gly Ala Thr Gly Ala Glu Gly Pro Arg Gly Phe Pro Gly His Met
                85                  90                  95

Gly Met Lys Gly Gln Lys Gly Glu Ser Ser Tyr Val Tyr Arg Ser Ala
            100                 105                 110

Phe Ser Val Gly Leu Thr Glu Arg Ala Pro His Pro Asn Val Pro Ile
        115                 120                 125

Arg Phe Thr Lys Ile Phe Tyr Asn Glu Gln Asn His Tyr Asp Ser Ser
    130                 135                 140

Thr Gly Lys Phe Leu Cys Ser Ile Pro Gly Thr Tyr Phe Phe Ala Tyr
145                 150                 155                 160

His Leu Thr Val Tyr Met Thr Asp Val Lys Val Ser Leu Tyr Lys Lys
                165                 170                 175

Asp Lys Ala Val Ile Phe Thr Tyr Asp Gln Phe Gln Glu Asn Asn Val
            180                 185                 190

Asp Gln Ala Ser Gly Ser Val Leu Leu His Leu Ser Leu Gly Asp Glu
        195                 200                 205

Val Trp Leu Gln Val Tyr Gly Glu Gly Asn Asn Asn Gly Val Tyr Ala
    210                 215                 220

Asp Asn Ile Asn Asp Ser Thr Phe Met Gly Phe Leu Leu Tyr Pro Asp
225                 230                 235                 240

Thr Asp Asp Arg
```

PHARMACEUTICAL COMPOSITIONS OF ADIPONECTIN VARIANTS AND METHODS OF STORAGE

CROSS-REFERENCE TO PRIOR APPLICATIONS

This application claims the benefit of prior U.S. application Ser. No. 11/328,901, filed Jan. 9, 2006; and prior U.S. Provisional Application Nos. 60/642,476, filed Jan. 7, 2005; 60/650,411, filed Feb. 3, 2005; 60/698,358, filed Jul. 11, 2005; 60/720,768, filed Sep. 26, 2005; and, 60/733,137, filed Nov. 2, 2005, 60/790,220, filed Apr. 7, 2006; 60/781,509, filed Mar. 9, 2006; 60/777,825, filed Mar. 1, 2006; all entirely incorporated by reference.

FIELD OF THE INVENTION

The present invention relates in general to adiponectin. More specifically, the invention relates to variants of human adiponectin with improved properties, including increased recombinant protein expression levels, increased solubility, increased soluble expression and stability, lower immunogenicity, and improved pharmacokinetics and/or pharmacodynamics, as well as methods of making such variants and using them to treat diseases.

BACKGROUND OF THE INVENTION

In addition to storing fat deposits, adipocytes secrete several cytokines important in regulating lipid and glucose metabolism in mammals. These so called "adipokines" include adiponectin, adipsin, leptin, and vaspin. In the literature, adiponectin has also been called GBP28, ApM1, ACRP30, AdipoQ, and OBG3. Unlike other adipokines, however, adiponectin serum levels are inversely correlated with obesity, insulin resistance and ischemic heart disease (Goldstein and Scalia (2004) *The Journal of Clinical Endocrinology and Metabolism* 89:2563-8, entirely incorporated by reference). While serum levels of adiponectin in normal humans typically range from 2 to 10 μg/mL, levels of circulating adiponectin are dramatically reduced in obese or diabetic individuals. Accordingly, adiponectin replacement therapy has been suggested as a possible treatment to reverse insulin resistance in type II diabetics and to ameliorate vascular atherosclerosis in at-risk cardiac patients, and decrease TNFα levels.

Adiponectin treatment has been shown to mobilize glucose uptake, increase fatty acid clearance from the circulation, and induce insulin sensitivity in both normal and insulin resistant tissues (Wu et al. (2003) *Diabetes* 52:1355-63; Fruebis et al. (2001) *PNAS* 98:2005-10; Berg et al. (2002) *TRENDS in Endocrinology and Metabolism* 13:84-9; all entirely incorporated by reference). Additional studies have shown that adiponectin has both cardioprotective and anti-inflammatory properties (Shimada et al (2004) *Clinica. Chemica. Acta.* 344:1-12; Hug and Lodish (2005) *Current Opinion in Pharmacology* 5:129-34, all entirely incorporated by reference). Adiponectin activity is mediated at least in part by it's stimulatory effects on the phosphorylation and subsequent activation of 5'-AMP-activated protein kinase (AMPK), the AMPK downstream substrate acetyl coenzyme A carboxylase (ACC) (Yamauchi et al. (2002) *Nature Medicine* 8:1288-95, entirely incorporated by reference), and also the pPAR family of steroid hormone receptors (Yamauchi et al. (200) *Journal of Biological Chemistry* 278:2461-8, entirely incorporated by reference). Recent studies show that adiponectin can interact with and alter the activity of several growth factors including platelet derived growth factor BB (PDGF-BB), heparin-binding epidermal growth factor-like growth factor (HB-EGF), and basic fibroblast growth factor (basic FGF) (Wang et al. (2005) *Journal of Biological Chemistry* 280:18341-7, entirely incorporated by reference).

Adiponectin is a 30 kD glycoprotein consisting of an N-terminal collagen-like domain, approximately residues 1-100, containing multiple G-X-X-G repeats and a C-terminal domain, approximately residues 108-244, structurally resembling the globular portions of the ClQ and TNF superfamily members. At least two proteolytic cleavage sites are located between the collagen and ClQ-like domains. Both full length and proteolytically cleaved forms are found in human serum. Globular head domain cleavage fragments of adiponectin ("globular" adiponectin or gAd) form trimeric structures, while full length adiponectin is capable of forming trimers, hexamers, and additional higher order oligomers. Mutation of the cysteine residue located in the collagen domain (conserved in all known mammalian adiponectin) abolishes hexamer and high-order oligomer formation.

Homologous proteins to adiponectin include, but are not limited to, mouse Clq/TNF-α Related Proteins 1 (CTRP1), CTRP2, CTRP3, CTRP4, CTRP5, CTRP6 and CTRP7. At least one of these proteins (CTRP2) is able to stimulate fatty acid oxidation in skeletal muscle, thus resembling the functional properties of adiponectin (Wong et al. (2004) *Proc. Natl. Acad. Sci.* 101:10302-7, entirely incorporated by reference).

Several adiponectin polymorphisms have been discovered within particular human populations. The severity of the phenotype depends on the position of the mutation. For example, the G84R, G90S, Y111H, and I164T mutations cause diabetes and hypoadiponectinemia as a result of a failure to form higher order oligomers that are likely important in regulating insulin sensitivity by the liver (Waki et al. (2003) *J. Biol. Chem.* 278:40352-63, entirely incorporated by reference). Functionally benign polymorphisms include R221S and H241P.

Based on their amino acid sequences, both known adiponectin receptors (AdipoR1 and AdipoR2) are predicted to contain seven transmembrane alpha helices but are not related to G-coupled protein receptors (Yamauchi et al. (2003) *Nature* 423:762-9, entirely incorporated by reference). Although AdipoR1 and AdipoR2 are homologous (>67% identity), their relative affinities to adiponectin and gAd differ. AdipoR1, expressed predominantly in skeletal muscle, binds to gAd with higher affinity than adiponectin, while AdipoR2, expressed predominantly in liver, binds preferentially to adiponectin. In vivo results in mice suggest that trimeric gAd may be more effective at reducing weight and improving insulin sensitivity than hexameric and higher order oligomeric forms of adiponectin (Yamauchi et al. (2001) *Nature Medicine* 7:941-6, entirely incorporated by reference).

While full-length adiponectin and gAd are very interesting pharmaceutical candidates, both full-length adiponectin and adiponectin fragments of naturally occurring adiponectin, in all known species, are very insoluble. In order to study the effects of adiponectin on any species larger than a mouse, variants of adiponectin with increased solubility are needed. Additionally, in order to produce pharmaceutically relevant quantities of full-length adiponectin or gAd, variants of adiponectin with very improved solubility are needed.

SUMMARY OF THE INVENTION

The present invention provides novel adiponectin variants that are optimized for increased levels of recombinant protein expression, improved solubility, improved soluble expression, improved stability, lower immunogenicity, and improved pharmacokinetics and/or pharmacodynamics.

Accordingly, some embodiments of the invention features an adiponectin variant comprising one or more amino acid modifications relative to a corresponding parent adiponectin, wherein the adiponectin variant is not glycosylated, wherein the adiponectin variant does not comprise residues 1-100 relative to human adiponectin (SEQ ID NO:1), and wherein the solubility of the variant is improved by at least 3-fold relative to residues 110-244 of SEQ ID NO:1.

In other embodiments, the invention feature a composition comprising a variant adiponectin peptide with the formula: V(109)-V(110)-V(111)-F(112)-F(113-121)-V(122)-F(123)-V(124)- V(125)-F(126-127)-V(128)-F(129-134)-V(135)-F(136-151)-V(152)-F(153-163)-F(164)-F(165-181)-V(182)-F(183)-V(184)-F(185-206)-V(207)-F(208-220)-F(221)-F(222-223)-V(224)-V(225)-F(226)-V(227)-F(228)-V(229), wherein V(109) is selected from the group consisting of: the wild-type amino acid V; any of variant amino acids D, E, H, K, N, Q, and R; and, a deletion of V109; V(110) is selected from the group consisting of: the wild-type amino acid V; any of variant amino acids D, E, H, K, N, Q, R, and S; and, a deletion of V110; V(111) is selected from the group consisting of: the wild-type amino acids Y and H; any of variant amino acids D, E, N, R, and S; and, a deletion of 111; F(112) is selected from the group consisting of the wild-type amino acids R and C, and, a deletion of 112; F(113-121) is selected from the group consisting of: the wild-type amino acid sequence SAFSVGLET; and, a deletion of any of S113, A114, F115, S116, V117, G118, L119, E120, and T121; V(122) is selected from the group consisting of: the wild-type amino acid Y; any of variant amino acids D, E, H, N, R, and S; and, a deletion of Y122; F(123) is selected from the group consisting of: the wild-type amino acid sequence V and a deletion of V123; V(124) is selected from the group consisting of: the wild-type amino acid T; any of variant amino acids D, E, K, N, and R; and, a deletion of T124; V(125) is selected from the group consisting of: the wild-type amino acid I; any of variant amino acids D, E, H, K N, Q, R, S, and T; and, a deletion of I125; F(126-127) comprises the wild-type amino acid sequence PN; V(128) is selected from the group consisting of: the wild-type amino acid M; and any of variant amino acids A, D, E, H, K, N, Q, R, S, and T; F(129-134) comprises the wild-type amino acid sequence PIRFTK; V(135) is selected from the group consisting of: the wild-type amino acid I; and, any of variant amino acids D, E, H, K, N, Q and R; F(136-151) comprises the wild-type amino acid sequence FYNQQNHYDGSTGKFH; V(152) is selected from the group consisting of: the wild-type amino acid C; and, any of variant amino acids A, F, L, N, S, T and V; F(153-163) comprises the wild-type amino acid sequence NIPGLYYFAYH; F(164) is selected from the group consisting of the wild-type amino acid I and T; F(165-181) comprises the wild-type amino acid sequence TVYMKDVKVSLFKKDKA; V(182) is selected from the group consisting of: the wild-type amino acid M; and, any of variant amino acids A, D, E, K, N, Q, R, S, and T; F(183) comprises the wild-type amino acid L; V(184) is selected from the group consisting of: the wild-type amino acid F; and, any of variant amino acids D, H, K, N and R; F(185-206) comprises the wild-type amino acid sequence TYDQYQENNVDQASGSVLLHLE; V(207) is selected from the group consisting of: the wild-type amino acid V; and, any of variant amino acids D, E, H, K, N, Q, R, and S; F(208-220) comprises the wild-type amino acid sequence GDQVWLQVYGEGE; F(221) is selected from the group consisting of the wild-type amino acids R and S; F(222-223) comprises the wild-type amino acid sequence NG; V(224) is selected from the group consisting of: the wild-type amino acid L; and, any of variant amino acids D, E, H, K, N, Q, R and S; V(225) is selected from the group consisting of: the wild-type amino acid Y; and, any of variant amino acids D, E, H, K, N, Q, R and S; F(226) comprises the wild-type amino acid A; V(227) is selected from the group consisting of: the wild-type amino acid D; and, any of variant amino acids H, K and R; F(228) comprises the wild-type amino acid N; or V(229) is selected from the group consisting of: the wild-type amino acid D; and, any of variant amino acids H, K and R; and wherein the variant adiponectin has at least a 3-fold improved solubility relative to residues 110-244 of SEQ ID NO:1 and the variant adiponectin peptide is not glycosylated.

In some embodiments, a variant adiponectin with at least a 3-fold improved solubility relative to residues 110-244 of human adiponectin (SEQ ID NO:1) contains a substitution selected from the group consisting of 122H; 122S; 125E; 125H; 125T; 184H; 207E; and 207K.

In other embodiments, a variant adiponectin with improved solubility relative to residues 110-244 of human adiponectin comprises at least two modifications such as substitutions.

In other embodiments, the solubility or soluble expression of a variant adiponectin is improved by at least n-fold relative to residues 110-244 of human adiponectin, where n is any number between 2 and 3000. For example, the solubility or soluble expression of the variant may be improved by at least 30-, 100-, 300, 1000-fold, 2000-fold and 3000-fold.

In some embodiments, the expression yield of a variant adiponectin is improved by at least n-fold relative to residues 110-244 of human adiponectin, where n is any number between 2 and 10000. For example, the expression yield of the variant may be improved by at least 2-, 5-, 10-, 50-, 100-, 300-, 500-, 1000-, 3000-, and 10000-fold.

In some embodiments, the ability of the variant to induce phosphorylation of AMPK in muscle cells is improved by at least 30% or 100% relative to residues 110-244 of human adiponectin. For example, phosphorylation of AMPK may be improved by at least 30%, 40%, 50%, 60%, 70%, 80%, 90% and 100%.

The corresponding wild-type adiponectin may be a human adiponectin (SEQ ID NO:1) or non-human, and the variant may include one or more amino acid modifications at position 109, 110, 115, 122, 123, 125, 128, 130, 132, 135, 150, 152, 160, 164, 166, 171, 173, 175, 182, 184, 205, 207, 211, 213, 215, 224, 225, 227, 229, or 234 relative to SEQ ID NO:1.

Especially preferred modifications to adiponectin include, but are not limited to, the following substitutions: Y109D, Y109E, Y109H, Y109K, Y109N, Y109Q, Y109R, V110D, V110E, V110H, V110K, V110N, V110Q, V110R, V110S, Y111D, Y111E, Y111K, Y111N, Y111Q, Y111R, Y122D, Y122E, Y122H, Y122N, Y122R, Y122S, I125D, I125E, I125H, I125K, I125N, I125Q, I125R, I125S, M128A, M128D, M128E, M128H, M128K, M128N, M128Q, M128R, M128S, M128T, I135D, I135E, I135H, I135K, I135N, I135Q, I135R, C152A, C152N, C152S, M182A, M182D, M182E, M182K, M182N, M182Q, M182R, M182S, M182T, F184D, F184H, F184K, F184N, F184R, V207D, V207E, V207H, V207K, V207N, V207Q, V207R, V207S, L224D, L224E, L224H, L224K, L224N, L224Q, L224R, L224S, Y225D, Y225E, Y225H, Y225K, Y225N, Y225Q, Y225R, Y225S, D227H, D227K, D227R, D229H, D229K, D229R, or a combination thereof.

In some preferred embodiments, an adiponectin variant of the present invention is PEGylated. In a more preferred embodiment, a PEG moiety is attached to an amino acid modification selected from the group of A108C, Y109C, S146C, D179C, E220C, R221C, and L224C, relative to human adiponectin (SEQ ID NO:1).

In other preferred embodiments, an adiponectin variant of the present invention has improved storage characteristics. For example, adiponectin variants of the present invention can be stored at 4° C. in a pharmaceutically acceptable carrier for at least one week at least at 2 mg/mL; 4 mg/mL, 5 mg/mL, 7 mg/mL and 10 mg/mL, without losing more than 20%, 10%, 5%, 4%, 3%, 2% or 1% total concentration. In especially preferred embodiments, the storage concentration in a pharmaceutically acceptable carrier may be 15 mg/mL, 20 mg/mL, 30 mg/mL, 40 mg/mL, 50 mg/mL, 60 mg/mL, 75 mg/mL, 100 mg/mL, 150 mg/mL, and 200 mg/mL, without losing more than 20%, 10%, 5%, 4%, 3%, 2% or 1% total concentration.

In another preferred embodiment, an adiponectin variant of the present invention can be stored in frozen form for at least one week at 10 mg/mL, 15 mg/mL, 20 mg/mL, 30 mg/mL, 40 mg/mL, 50 mg/mL, 75 mg/mL, 100 mg/mL, 150 mg/mL, and 200 mg/mL. In an alternate embodiment, an adiponectin variant of the present invention may be stored in lyophilized form.

Also within the invention is a pharmaceutical composition comprising a variant adiponectin peptide, where the solubility or soluble expression of the variant adiponectin is improved by at least n-fold relative to residues 110-244 of human adiponectin, where n is at least any number between 2 and 3000. For example, the solubility or soluble expression of the variant may be improved by at least 5-, 10-, 15-, 20-, 30-, 50-, 100-, 300-, 1000-, 2000-, and 3000-fold.

Also within the invention is a method of treating a mammal with an adiponectin mediated disorder comprising administering a therapeutically effective amount of an adiponectin variant described herein.

In another aspect, the invention features a composition comprising a polynucleotide encoding an adiponectin variant described herein.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

BRIEF DESCRIPTION OF THE FIGURES

FIG. 1 shows the full-length human adiponectin amino acid sequence (Genbank accession No. Q15848, residues 1-244), designated SEQ ID NO:1.

FIG. 2 shows ClustalW alignment of full-length human SEQ ID NO:1, rhesus macaque SEQ ID NO:4, boar SEQ ID NO:6, dog SEQ ID NO:5, cow SEQ ID NO:7, rat SEQ ID NO:3, mouse SEQ ID NO:2, and chicken SEQ ID NO:8 adiponectin.

FIG. 3 is a table of exposed hydrophobic residues in the adiponectin collagen region and alternative polar residues. SEQ ID NO:1

FIG. 4 is a table of alternative polar residues from ortholog alignment in the adiponectin collagen region. SEQ ID NO:1

FIG. 5 is a table of regions of high electrostatic potential in the adiponectin collagen region and compensating substitutions. SEQ ID NO:1

FIG. 6 is a table of hydroxyprolines in the adiponectin collagen region and appropriate substitutions. SEQ ID NO:1

FIG. 7 is a table of aromatic amino acids in the adiponectin collagen region and appropriate substitutions. SEQ ID NO:1

FIG. 8 is a table of especially preferred substitutions in the adiponectin collagen region. SEQ ID NO:1

FIG. 9 is a table of exposed hydrophobic residues in the adiponectin globular region. SEQ ID NO:1

FIG. 11 is a table of exposed hydrophobic residues in the adiponectin globular region and alternative polar residues. SEQ ID NO:1

FIG. 12 is a table of alternative polar residues from ortholog alignment. SEQ ID NO:1

FIG. 13 is a table of energies of most favorable polar substitutions for gAd solvent-exposed hydrophobic positions. SEQ ID NO:1

FIG. 14 is a table of alternate polar residues in gAd. SEQ ID NO:1

FIG. 15 is a table of regions of high electrostatic potential in gAd. SEQ ID NO:1

FIG. 16 is a table of energies of most favorable positively charged residues to replace aspartate 227 and 229 in gAd. SEQ ID NO:1

FIG. 17 is a table of energies of most favorable non-glycine residues to replace cysteine 152 in gAd. SEQ ID NO:1

FIG. 18 is a table of energies of most favorable non-glycine, polar residues to replace methionine 128 and 182 in gAd. SEQ ID NO:1

FIG. 19 is a table of energies of favored coupled substitutions at positions 109, 110 and 111. SEQ ID NO:1

FIG. 20 is a table of energies of favored coupled substitutions at positions 122 and 125. SEQ ID NO:1

FIG. 21 is a table of energies of favored coupled substitutions at positions 224 and 225. SEQ ID NO:1

FIG. 22 is a table of energies of favored substitutions at core positions within gAd. SEQ ID NO:1

FIG. 25 is a schematic of the bacterial expression vector pET-17b for expressing gAd.

FIG. 26 is a table listing gAd Library #1, single variants. SEQ ID NO:1

FIG. 27*a* is a table of SDS-PAGE loading to screen the soluble or insoluble fractions of Library #1 variants. FIG. 27*b* shows SDS-PAGE gels of 34 single amino acid substitution-containing gAd variants. Proteins were expressed in *E. Coli* and lysates were prepared in the presence of detergent. SEQ ID NO:1

FIG. 28*a* SDS-PAGE loading to screen the soluble or insoluble fractions of select single variants in the absence of detergent. FIG. 28*b* shows solubility or soluble expression of selected single amino acid substitution-containing gAd variants. Proteins were expressed in *E. Coli* and lysates were prepared under detergent-free conditions. SEQ ID NO:1

FIG. 29*a* is a table of SDS-PAGE loading to screen the total, soluble, and insoluble fractions of double mutant globular adiponectin variants in the presence of detergent. FIG. 29*b* shows SDS-PAGE analysis of eight single amino acid and 23 double amino acid substitution -containing gAd variants. Proteins were expressed in *E. coli* and lysates were prepared in the presence of detergent. SEQ ID NO:1

FIG. 30*a* is a table of SDS-PAGE loading to screen the soluble or insoluble fractions of select double variants in the absence of detergent. FIG. 30*b* shows solubility or soluble expression analyses of selected single and double amino acid substitution-containing gAd variants listed in FIG. 30*a*. Proteins were expressed in *E. Coli* and lysates were prepared under detergent-free conditions. SEQ ID NO:1

FIG. 31A shows SDS-PAGE gel of showing purification and average yield of selected gAd variants.

FIG. 32 is a SDS-PAGE gel that contains a serial dilution of variant I125E/V207E relative to wild-type. Proteins were expressed in *E. Coli* and lysates were prepared under detergent -free conditions. SEQ ID NO:1

FIG. 35 shows phase contrast time-course images of mouse C2C12 myotube differentiation.

FIG. 38 is a table of energies of preferred substitutions for gAd as determined with PDA.RTM. technology. SEQ ID NO:1

FIG. 39 is a table of energies of hydrophobic surface patches in adiponectin. FIG. 39A is a patch for Y122. FIG. 39B is a patch for I125. FIG. 39C is a patch for F184. FIG. 39D is a patch for V207. SEQ ID NO:1

FIG. 40 is a table of mean RHD values for identified surface patches containing favorable variants. SEQ ID NO:1

FIG. 41 is a table of energies for identified favorable variants that reduce surface patch hydrophobicity. SEQ ID NO:1

FIG. 42 is a graph showing select gAd variants inhibit cAMP-induced lipolysis in primary human adipocytes. SEQ ID NO:1

FIG. 43 is a graph showing a dose response of gAd Y122S/I125E-induced glucose uptake in primary human adipocytes. SEQ ID NO:1

FIG. 44 are Western blots showing a time course of gAd Y122S/I125E-induced AMPK and ACC phosphorylation. SEQ ID NO:1

FIG. 45 is a Western blot showing a dose response of gAd Y122S/I125E-induced AMPK phosphorylation. SEQ ID NO:1

FIG. 46 a graph and Western blot showing a dose response of gAd Y122S/I1125E-induced AMP Kinase activity assays done using radioactive phosphate incorporation into the SAMS peptide substrate. SEQ ID NO:1

FIG. 47 is a graph of the effect of gAd Y122S/I125E on palmitate oxidation in L6 myotubes. SEQ ID NO:1

FIG. 48 is a graph showing gAd Y122S/I125E stimulation of glucose uptake in L6 myotubes. SEQ ID NO:1

FIG. 49 is a graph of PK in female mice, 1 mg/kg gAd Y122S/I125E was administered IV, IP, and SC. SEQ ID NO:1

FIG. 50 is a graph of PK in female mice, 6 mg/kg gAd Y122S/I125E was administered IV, IP, and SC. SEQ ID NO:1

FIG. 51 is a table of PK parameters obtained from non-compartmental analysis of the serum gAd levels.

FIG. 52 is a graph showing fed glucose levels during treatment of diabetic mice with gAd Y122S/I125E. SEQ ID NO:1

FIG. 53 is a graph showing weight gain of mice during treatment of diabetic mice with gAd Y122S/I125E.

FIGS. 54A and 54B are graphs showing IP-GTT in diabetic mice before and after treatment a 19 day treatment with gAd Y122S/I125E, respectively. SEQ ID NO:1

FIG. 55 shows SDS PAGE gels of gAd Y122S/I125E effects on phosphorylation of AMPK, ACO, and NOS in aorta and myocardium cells. SEQ ID NO:1

DETAILED DESCRIPTION OF THE INVENTION

Figure 10:
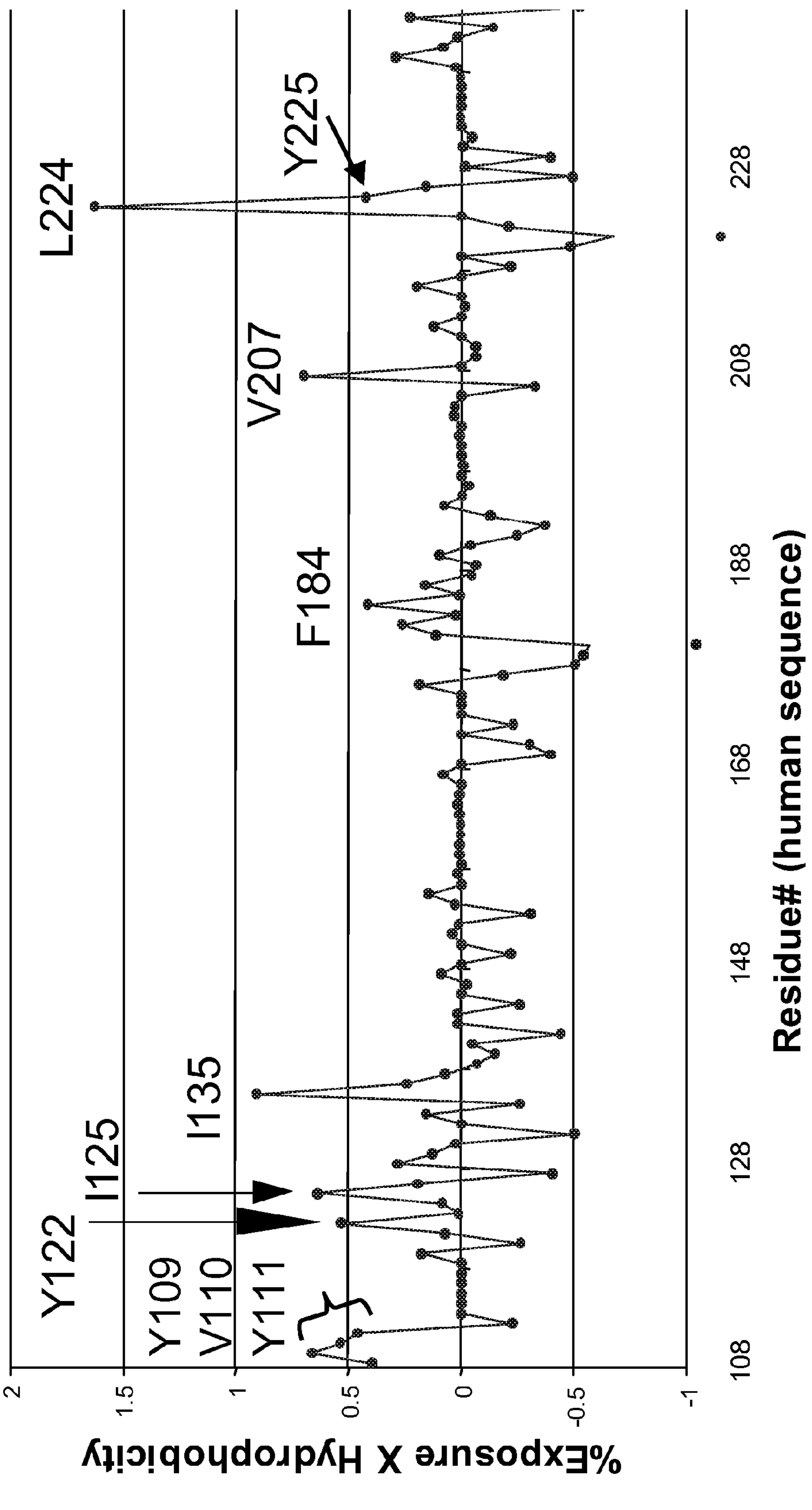
FIG. 10 is a graph that demonstrates the relationship between amino acid surface exposure and the relative hydrophobicity of that amino acid. SEQ ID NO:1

In order that the invention may be more completely understood, several definitions are set forth below. Such definitions are meant to encompass grammatical equivalents.

By "adiponectin" herein is meant a polypeptide that is primarily derived in adipocytes and is an ortholog of any sequence shown in FIG. 2, including fragments of naturally-occurring adiponectin, especially fragments containing the globular domain of adiponectin.

By "adiponectin variant" herein is meant a polypeptide that is functionally similar to adiponectin but contains modifications relative to a naturally-occurring adiponectin sequence.

By "globular domain" herein is meant, in the context of adiponectin, the Clq/TNF-α-like domain and not including the collagen domain. This region can include but is not limited to residues 108-244 relative to human adiponectin (SEQ ID NO:1).

By "hydrophobic residues" and grammatical equivalents are meant valine, isoleucine, leucine, methionine, phenylalanine, tyrosine, tryptophan, and functional equivalents thereof.

By "polar residues" and grammatical equivalents herein are meant aspartic acid, asparagine, glutamic acid, glutamine, lysine, arginine, histidine, serine, and functional equivalents thereof.

By "protein properties" herein are meant physical, chemical, and biological properties including but not limited to physical properties (including molecular weight, hydrodynamic properties such as radius of gyration, net charge, isoelectric point, and spectral properties such as extinction coefficient), structural properties (including secondary, tertiary, and quaternary structural elements), stability (including thermal stability, stability as a function of pH or solution conditions, storage stability, and resistance or susceptibility to ubiquitination, proteolytic degradation, or chemical modifications such as methionine oxidation, asparagine and glutamine deamidation, sidechain racemerization or epimerization, and hydrolysis of peptide bonds), solubility (including susceptibility to aggregation under various conditions, oligomerization state, and crystallizability), kinetic and dynamic properties (including flexibility, rigidity, folding rate, folding mechanism, allostery, and the ability to undergo conformational changes and correlated motions), binding affinity and specificity (to one or more molecules including proteins, nucleic acids, polysaccharides, lipids, and small molecules, and including affinities and association and dissociation rates), enzymatic activity (including substrate specificity; association, reaction, and dissociation rates; reaction mechanism; and pH profile), ammenability to synthetic modification (including PEGylation and attachment to other molecules or surfaces), expression properties (such as yield in one or more expression hosts, soluble versus inclusion body expression, subcellular localization, ability to be secreted, and ability to be displayed on the surface of a cell), processing and posttranslational modifications (including proteolytic processing, N- or C-linked glycosylation, lipidation, sulfation, and phosphorylation), pharmacokinetic and pharmacodynamic properties (including bioavailability following subcutaneous, intramuscular, oral, or pulmonary delivery; serum half-life, distribution, and mechanism and rate of elimination), and ability to induce altered phenotype or changed physiology (including immunogenicity, toxicity, ability to signal or inhibit signaling, ability to stimulate or inhibit cell proliferation, differentiation, or migration, ability to induce apoptosis, and ability to treat disease).

By "solubility" and grammatical equivalents herein is meant the maximum possible concentration of protein, in the desired or physiologically appropriate oligomerization state, in a solution of specified condition (i.e., pH, temperature, concentration of any buffer components, salts, detergents, osmolytes, etc.). The level of solubility can be determined by measuring, with standard methods, the quantity of a variant adiponectin in a solution. For the purposes of this invention, solubility should be assessed under solution conditions that are pharmaceutically acceptable. Specifically, a preferred pH range is between 6.0 and 8.0, salt concentration should be between 50 and 250 mM. Additional buffer components such as excipients may also be included; although it is preferred that albumin is not required. In one embodiment, a variant adiponectin can be stored at 4° C. for one week in a pharmaceutically acceptable carrier and not lose more than 50%, 40%, 30%, 20%, 10%, 5%, 4%, 3%, 2%, and 1% in the amount of soluble protein. Ideally, a variant adiponectin can be stored at 4° C. for one week in a pharmaceutically acceptable carrier at a concentration of 2 mg/mL, 3 mg/mL, 4 mg/mL, 5 mg/mL, 6 mg/mL, 7 mg/mL, 8 mg/mL, 10 mg/mL, 15 mg/mL, 20 mg/mL, 25 mg/mL, 30 mg/mL, 40 mg/mL, 50 mg/mL, 60 mg/mL, 75 mg/mL, 100 mg/mL, 150 mg/mL, and 200 mg/mL, and not lose more than 5%, 4%, 3%, 2%, and 1% in the amount of soluble protein.

By "improved solubility" and grammatical equivalents herein is meant an increase in the maximum possible concentration of protein, in the desired or physiologically appropriate oligomerization state, in solution. For example, if a wild-type adiponectin can be concentrated to 0.3 mg/mL in solution and the variant can be concentrated to 3 mg/mL under the same solution conditions, the variant can be said to have improved solubility of 10-fold. In a preferred embodiment, solubility is increased by at least a factor of 2, with increases of at least 3-, 4-, 5-, 6-, 8-, 10-, 20-, 30-, 40, 50-, and 60-fold being more preferred, and increases of at least 75-, 100-, 200-, 300-, 400-, 500-, 750-, 1000- and 2000-fold being especially preferred. As will be appreciated by those skilled in the art, solubility is a function of solution conditions.

By "soluble expression" and grammatical equivalents herein is meant the amount of target protein in a crude supernatant prepared in the absence of detergent. For example, a target protein is expressed in an appropriate expression system, cells harvested and lysed in the absence of detergent, and a crude supernatant is prepared by standard methods. The amount of a variant adiponectin in the crude supernatant is the soluble expressed protein. The level of soluble expression can be determined by measuring with standard methods the quantity of a variant adiponectin in the supernatant.

By "improved soluble expression" and grammatical equivalents herein is meant an increase in the quantity of variant protein in a crude supernatant prepared in the absence of detergent relative to a parent protein. For example, if a wild-type adiponectin has a soluble expression of to 0.3 mg/L and a variant has a soluble expression of 600 mg/L under the same solution conditions, the variant can be said to have improved solubility of 2000-fold. In a preferred embodiment, soluble expression is increased by at least a factor of 2, with increases of at least 3-, 4-, 5-, 6-, 8-, 10-, 20-, 30-, 40, 50-, and 60-fold being more preferred, and increases of at least 75-, 100-, 200-, 300-, 400-, 500-, 750-, 1000- and 2000-fold being especially preferred.

By "modification" and grammatical equivalents is meant one or more insertions or substitutions to a protein or nucleic acid sequence. The insertions and substitutions include naturally- and non-naturally-occurring amino acids and nucleotides, as well as their functional equivalents.

By "naturally occurring" or "wild type" or "wt" or "native" and grammatical equivalents thereof herein is meant an amino acid sequence or a nucleotide sequence that is found in nature, including allelic variations. In a preferred embodiment, the wild type sequence is the most prevalent human sequence. However, the wild type adiponectin nucleic acids and proteins may be a less prevalent human allele or adiponectin nucleic acids and proteins from any number of organisms, including but not limited to rodents (rats, mice, hamsters, guinea pigs, etc.), primates, and farm animals (including sheep, goats, pigs, cows, horses, etc).

By "expression yield" and grammatical equivalents herein is meant the amount of protein, preferably in mg/L or PCD (picograms per cell per day) that is produced or secreted under a given expression protocol (that is, a specific expression host, transfection method, media, time, etc.).

By "improved expression yield" and grammatical equivalents herein is meant an increase in expression yield, relative to a wild type or parent protein, under a given set of expression conditions. In a preferred embodiment, at least a 50% improvement is achieved, with improvements of with increases of at least 2-, 3-, 4-, 5-, 6-, 8-, 10-, 20-, 30-, 40, 50-, and 60-fold being more preferred, and increases of at least 70-, 80-, 90-, 100-, and 150-fold being especially preferred.

The terms "treat, treating, or treatment" is defined as administration of a substance to a subject with the purpose to cure, alleviate, relieve, remedy, prevent, or ameliorate a disorder, symptoms of the disorder, a disease state secondary to the disorder, or predisposition toward the disorder. A "subject," as used herein, refers to human and non-human animals, including all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model. Identification of a candidate subject can be in the judgment of the subject or a health care professional, and can be subjective (e.g., opinion) or objective (e.g., measurable by a test or diagnostic method). The term "effective amount" is an amount of the composition that is capable of producing a medically desirable result in a treated subject. The medically desirable result may be objective (i.e., measurable by some test or marker, e.g., healing of acute conditions associated with type-2 diabetes, weight loss for obesity, etc.) or subjective (i.e., subject gives an indication of or feels an effect).

As used herein, "pharmaceutically acceptable carrier" is intended to include any and all solvents, dispersion media, coatings, antibacterial and antifungal agents, isotonic and absorption delaying agents, and the like, compatible with pharmaceutical administration. "Dosage unit form," as used herein, refers to physically discrete units suited as unitary dosages for the subject to be treated, each unit containing a predetermined quantity of active compound calculated to produce the desired therapeutic effect in association with the required pharmaceutical carrier.

Adiponectin Variants with Increased Solublity

As mentioned previously, serum levels of endogenous adiponectin in healthy individuals typically lies between 2 to 10 μg/mL, a rather large amount relative to other serum proteins. If these amounts are required for efficacious replacement therapy to treat, for example, obesity or diabetes, large quantities of highly soluble, non-aggregation-prone protein may be required. Highly soluble adiponectin variants will allow administration to patients and will likely lead to efficient product manufacturing.

The invention is based, at least in part, upon the unexpected discovery that adiponectin can be modified such that the physical properties and/or biological activities of the polypeptide are improved. Accordingly, the invention provides an adiponectin variant with improved physical properties (e.g., stability, solubility or soluble expression, and expression yield) and/or biological activities (e.g., the ability to induce phosphorylation of AMPK), as compared to the corresponding wild-type adiponectin. The variant comprises one or more amino acid modifications to the corresponding wild-type adiponectin. The modifications can be made at the following positions:

(1) Positions that have predetermined hydrophobicity and percent exposure. Hydrophobicity and percent exposure of an amino acid can be determined as described below or by any method known in the art. In preferred embodiments, the top 10% of exposed hydrophobic amino acids are selected for modification.

(2) Positions that have predetermined polarity. Examples of polar residues include aspartic acid, asparagine, glutamic acid, glutamine, lysine, arginine, histidine, and serine. In some embodiments, charged polar residues are substituted for neutral polar residues occurring naturally in adiponectin.

(3) Positions that have predetermined electrostatic potential. Electrostatic potential of an amino acid can be determined as described below or by any method known in the art. In preferred embodiments, amino acids with electrostatic potentials greater than 0.5 kcal/mol or less than −0.5 kcal/mol are selected for modification.

(4) Positions that have Met, e.g., positions 40, 128, 168, and 182 of SEQ ID NO:1.

(5) Positions that have hydroxyPro, e.g., positions 44, 47, 53, 62, 71, 86, 95, and 104 of SEQ ID NO:1.

(6) Positions that have an aromatic amino acid, e.g., positions 46, 49, and 94 of SEQ ID NO:1.

(7) Cys corresponding to position 152 of SEQ ID NO:1.

(8) Positions that have potential PEGylation site, e.g., positions 108, 109, 110, 120, 127, 133, 136, 137, 139, 141, 146, 170, 179, 180, 184, 186, 188, 189, 191, 192, 196, 202, 204, 206, 207, 208, 218, 220, 221, 223, 224, 225, 226, 227, 229, 240, 243, and 244 of SEQ ID NO:1.

(9) Positions that have amino acids affecting isoelectric point of the wild-type or variant adiponectin. Such amino acids can be determined by any method known in the art. Examples of such amino acids include aspartic acid, glutamic acid, histidine, lysine, arginine, tyrosine, and cysteine.

(10) Positions that have amino acids affecting beta sheet formation, helix capping, or dipole interactions. Such amino acids can be determined by any method known in the art.

Strategies for Improving Solubility or Soluble Expression

A variety of strategies may be utilized to design adiponectin variants with improved solubility or soluble expression and expression yield. In a preferred embodiment, one or more of the following strategies are used: 1) reduce hydrophobicity by substituting one or more solvent-exposed hydrophobic residues with suitable polar residues; 2) increase polar character by substituting one or more neutral polar residues with charged polar residues; 3) increase protein stability, for example by one or more modifications that improve packing in the hydrophobic core, increase beta sheet forming propensity, improve helix capping and dipole interactions, or remove unfavorable electrostatic interactions (increasing the stability of a protein may improve solubility or soluble expression by decreasing the population of partially folded or misfolded states that are prone to aggregation); 4) modify one or more residues that can affect the isoelectric point of the protein (that is, aspartic acid, glutamic acid, histidine, lysine, arginine, tyrosine, and cysteine residues.) (Protein solubility or soluble expression is typically at a minimum when the isoelectric point of the protein is equal to the pH of the surrounding solution. Modifications that perturb the isoelectric point of the protein away from the pH of a relevant environment, such as serum, may therefore serve to improve solubility or soluble expression. Furthermore, modifications that decrease the isoelectric point of a protein may improve injection site absorption (Holash et. al. (2002) *Proc. Nat. Acad. Sci. USA* 99:11393-8, entirely incorporated by reference)); 5) truncation of N- or C-terminal residues; 6) addition or chemical attachment of solubility or soluble expression tags (e.g., peptide or chemical moieties that have high solubility or soluble expression); and 7) PEGylation. Additional strategies may involve the use of directed evolution methods to discover variants that improve solubility or soluble expression (see, for example, Waldo (2002) *Curr Opin Chem Biol.* 7(1):33-8, entirely incorporated by reference).

Strategies for Improving Expression Yield

A number of nucleic acid properties and protein properties may influence expression yields; furthermore, the expression host and expression protocol contribute to yields. Any of these parameters may be optimized to improve expression yields. Also, expression yield may be improved by the incorporation of one or more mutations that confer improved stability and/or solubility or soluble expression, as discussed further herein.

In an alternate embodiment, if expression is in a eukaryotic system, nucleic acid properties are optimized to improve expression yields using one or more of the following strategies: 1) replace imperfect Kozak sequence; 2) reduce 5' GC content and secondary structure of the RNA; 3) optimize codon usage; 4) use an alternate leader sequence; 5) include a chimeric intron; or 6) add an optimized poly-A tail to the C-terminus of the message. In another preferred embodiment, protein properties are optimized to improve expression yields using one or more of the following strategies: 1) optimize the signal sequence; 2) optimize the proteolytic processing site; 3) replace one or more cysteine residues in order to minimize formation of improper disulfide bonds; 4) improve the rate or efficiency of protein folding; or 5) increase protein stability, especially proteolytic stability.

Methods of Making Adiponectin Variants

The invention provides polynucleotides (DNA or RNA) comprising sequences encoding the adiponectin variants described herein. The adiponectin variants and polynucleotides of the invention can be made as described herein or by any chemical synthesis or genetic engineering method known in the art. The polynucleotides of the invention can be used to produce the adiponectin variants of the invention.

Adiponectin is typically expressed in mammalian cells. In order to enable the use of alternate expression systems, including but not limited to yeast expression systems, it would be desirable to 1) eliminate potential N-linked glycosylation sites, and, 2) eliminate potential O-linked glycosylation sites. In a preferred embodiment, one or more N- or O-linked glycosylation sites are removed. Removal of glycosylation sites from variant adiponectin polypeptides may be accomplished, for example, by the elimination of one or more glutamic acid, aspartic acid, serine or threonine residues to the native sequence or variant adiponectin polypeptide (for O-linked glycosylation sites) or by the modification of a canonical N-linked glycosylation site, N-X-Y-X, where X is any amino acid except for proline and Y is threonine, serine or cysteine. In another preferred embodiment, the modification in the variant adiponectin does not create an N- or O-linked glycosylation site.

In a preferred embodiment, nucleic acids encoding adiponectin variants are prepared by total gene synthesis, or by site-directed mutagenesis of a nucleic acid encoding wild type or variant adiponectin. Methods including template-directed ligation, recursive PCR, cassette mutagenesis, site-directed mutagenesis or other techniques that are known in the art may be utilized (see for example Strizhov et. al., PNAS 93:15012-15017 (1996), Prodromou and Perl, Prot. Eng. 5: 827-829 (1992), Jayaraman and Puccini, Biotechniques 12: 392-398 (1992), and Chalmers et al., Biotechniques 30: 249-252 (2001), all entirely incorporated by reference).

As will be appreciated by those in the art, the type of cells used in the present invention can vary widely. Appropriate host cells for the expression of adiponectin variants include yeast, bacteria, archaebacteria, fungi, and insect and animal cells, including mammalian cells. Some embodiments may use fungi such as *Saccharomyces cerevisiae* and *Pichia pastoris*, insect such as *Drosophila melanogaster* cells, yeast cells, *E. coli, Bacillus subtilis, Streptococcus cremoris, Streptococcus lividans*, pED (commercially available from Novagen), pBAD and pCNDA (commercially available from Invitrogen), pEGEX (commercially available from Amersham Biosciences), pQE (commercially available from Qiagen), SF9 cells, C129 cells, and mammalian cell lines including 293 (e.g., 293-T and 293-EBNA), BRK, CHO (e.g., CHOK1 and DG44), NIH3T3, *Neurospora*, COS, HeLa cells, fibroblasts, Schwanoma cell lines, immortalized mammalian myeloid, lymphoid cell lines, Jurkat cells, mast cells and other endocrine and exocrine cells, and neuronal cells, etc. (see the ATCC cell line catalog, entirely incorporated by reference). Adiponectin variants can also be produced in more complex organisms, including but not limited to plants (such as corn, tobacco, and algae) and animals (such as chickens, goats, cows); see for example Dove, Nature Biotechnol. 20: 777-779 (2002), entirely incorporated by reference. In one embodiment, the cells may be additionally genetically engineered, that is, contain exogenous nucleic acid other than the expression vector comprising the variant adiponectin nucleic acid.

In a preferred embodiment, variant adiponectin is expressed in bacterial systems, including bacteria in which the expression constructs are introduced into the bacteria using phage or other appropriate methods. Bacterial expression systems are well known in the art, and include *Bacillus subtilis, Escherichia coli, Streptococcus cremoris, Streptococcus lividans*, and *Salmonella typhimurium.*

In an alternate embodiment, the variant adiponectin is expressed in mammalian expression systems, including systems in which the expression constructs are introduced into the mammalian cells using virus such as retrovirus or adenovirus. Any mammalian cells may be used, with mouse, rat, primate and human cells being particularly preferred, although as will be appreciated by those in the art, modifications of the system by pseudotyping allows all eukaryotic cells to be used, preferably higher eukaryotes. Accordingly, suitable mammalian cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cells and B cells), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc.

In an alternate embodiment, variant adiponectin is produced in insect cells, including but not limited to *Drosophila melanogaster* S2 cells, as well as cells derived from members of the order Lepidoptera which includes all butterflies and moths, such as the silkmoth *Bombyx mori* and the alphalpha looper *Autographa californica*. Lepidopteran insects are host organisms for some members of a family of virus, known as baculoviruses (more than 400 known species), that infect a variety of arthropods. (see U.S. Pat. No. 6,090,584, entirely incorporated by reference). The variant adiponectin can be transfected into SF9 *Spodoptera frugiperda* insect cells to generate baculovirus which are used to infect SF21 or High Five commercially available from Invitrogen, insect cells for high level protein production.

In one embodiment, variant adiponectin is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica.*

In one embodiment variant adiponectin are expressed in vitro using cell free translation systems. Several commercial sources are available for this including but not limited to Roche Rapid Translation System, Promega TnT system, Novagen's EcoPro system, Ambion's ProteinScipt-Pro system. In vitro translation systems derived from both prokaryotic (e.g., *E. coli*) and eukaryotic (e.g., Wheat germ, Rabbit reticulocytes) cells are available. Both linear (as derived from a PCR amplification) and circular (as in plasmid) DNA molecules are suitable for such expression as long as they contain the gene encoding the variant adiponectin operably linked to an appropriate promoter. Other features of the molecule that are important for optimal expression in either the bacterial or eukaryotic cells (including the ribosome binding site, etc.) are also included in these constructs.

The methods of introducing exogenous nucleic acid into host cells is well known in the art, and will vary with the host cell used. Techniques include dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

A variety of expression vectors may be utilized to express the variant adiponectin. The expression vectors are constructed to be compatible with the host cell type. Expression vectors may comprise self-replicating extrachromosomal vectors or vectors which integrate into a host genome. Expression vectors typically comprise a variant adiponectin, any fusion constructs, control or regulatory sequences, selectable markers, and/or additional elements. Preferred bacterial expression vectors include but are not limited to pET, pBAD, bluescript, pUC, pQE, pGEX, pMAL, and the like. Preferred yeast expression vectors include pPICZ, pPIC3.5K, and pHIL-SI commercially available from Invitrogen. Expression vectors for the transformation of insect cells, and in particular, baculovirus-based expression vectors, are well known in the art and are described, e.g., in O'Reilly et al., *Baculovirus Expression Vectors: A Laboratory Manual* (New York: Oxford University Press, 1994), entirely incorporated by reference. A preferred mammalian expression vector system is a retroviral vector system such as is generally described in Mann et al., Cell, 33:153-9 (1993); Pear et al., Proc. Natl. Acad. Sci. U.S.A., 90(18):8392-6 (1993); Kitamura et al., Proc. Natl. Acad. Sci. U.S.A., 92:9146-50 (1995); Kinsella et al., Human Gene Therapy, 7:1405-13; Hofmann et al., Proc. Natl. Acad. Sci. U.S.A., 93:5185-90; Choate et al., Human Gene Therapy, 7:2247 (1996); PCT/US97/01019 and PCT/US97/01048, and references cited therein, all entirely incorporated by reference.

Expression Vectors

Generally, expression vectors include transcriptional and translational regulatory nucleic acid sequences which are operably linked to the nucleic acid sequence encoding the variant adiponectin. The transcriptional and translational regulatory nucleic acid sequences will generally be appropriate to the host cell used to express the variant adiponectin, as will be appreciated by those in the art. For example, transcriptional and translational regulatory sequences from *E. coli* are preferably used to express variant adiponectin in *E. coli.*

Promoter Sequences

Transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences comprise a promoter and transcriptional and translational start and stop sequences.

A suitable promoter is any nucleic acid sequence capable of binding RNA polymerase and initiating the downstream (3') transcription of the coding sequence of variant adiponectin into mRNA. Promoter sequences may be constitutive or inducible. The promoters may be naturally occurring promoters, hybrid or synthetic promoters.

A suitable bacterial promoter has a transcription initiation region which is usually placed proximal to the 5' end of the coding sequence. The transcription initiation region typically includes an RNA polymerase binding site and a transcription initiation site. In *E. coli*, the ribosome-binding site is called the Shine-Dalgarno (SD) sequence and includes an initiation codon and a sequence 3-9 nucleotides in length located 3-11 nucleotides upstream of the initiation codon. Promoter sequences for metabolic pathway enzymes are commonly utilized. Examples include promoter sequences derived from sugar metabolizing enzymes, such as galactose, lactose and maltose, and sequences derived from biosynthetic enzymes such as tryptophan. Promoters from bacteriophage, such as the T7 promoter, may also be used. In addition, synthetic promoters and hybrid promoters are also useful; for example, the tac promoter is a hybrid of the trp and lac promoter sequences.

Preferred yeast promoter sequences include the inducible GAL1,10 promoter, the promoters from alcohol dehydrogenase, enolase, glucokinase, glucose-6-phosphate isomerase, glyceraldehyde -3-phosphate-dehydrogenase, hexokinase, phosphofructokinase, 3-phosphoglycerate mutase, pyruvate kinase, and the acid phosphatase gene.

A suitable mammalian promoter will have a transcription initiating region, which is usually placed proximal to the 5' end of the coding sequence, and a TATA box, usually located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site -specific post-translational cleavage and polyadenylation. Examples of transcription terminator and polyadenylation signals include those derived from SV40. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Selection Gene or Marker

In addition, in a preferred embodiment, the expression vector contains a selection gene or marker to allow the selection of transformed host cells containing the expression vector. Selection genes are well known in the art and will vary with the host cell used.

For example, a bacterial expression vector may include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline.

Yeast selectable markers include the biosynthetic genes ADE2, HIS4, LEU2, and TRP1 when used in the context of auxotrophe strains; ALG7, which confers resistance to tunicamycin; the neomycin phosphotransferase gene, which confers resistance to G418; and the CUP1 gene, which allows yeast to grow in the presence of copper ions.

Suitable mammalian selection markers include, but are not limited to, those that confer resistance to neomycin (or its analog G418), blasticidin S, histinidol D, bleomycin, puromycin, hygromycin B, and other drugs. Selectable markers conferring survivability in a specific media include, but are not limited to Blasticidin S Deaminase, Neomycin phophotranserase II, Hygromycin B phosphotranserase, Puromycin N-acetyl transferase, Bleomycin resistance protein (or Zeocin resistance protein, Phleomycin resistance protein, or phleomycin/zeocin binding protein), hypoxanthine guanosine phosphoribosyl transferase (HPRT), Thymidylate synthase, xanthine-guanine phosphoridosyl transferase, and the like.

In one embodiment, the variant adiponectin comprises a purification tag operably linked to the rest of the variant adiponectin. A purification tag is a sequence which may be used to purify or isolate the candidate agent, for detection, for immunoprecipitation, for FACS (fluorescence-activated cell sorting), or for other reasons. Thus, for example, purification tags include purification sequences such as polyhistidine, including but not limited to $His_6$, or other tag for use with Immobilized Metal Affinity Chromatography (IMAC) systems (e.g. $Ni^{+2}$ affinity columns), GST fusions, MBP fusions, Strep-tag, the BSP biotinylation target sequence of the bacterial enzyme BirA, and epitope tags which are targeted by antibodies. Suitable epitope tags include but are not limited to c-myc (for use with the commercially available 9E10 antibody), flag tag, and the like.

Strategies for Reducing Immunogenicity

Several methods have been developed to modulate the immunogenicity of proteins. In some cases, PEGylation has been observed to reduce the fraction of patients who raise neutralizing antibodies by sterically blocking access to antibody agretopes (see for example, Hershfield et al. (1991) *PNAS* 88:7185-9; Bailon et al. (2001) *Bioconjug. Chem.* 12:195-202; He et al. (1999) Life Sci. 65:355-68, all entirely incorporated by reference). Methods that improve the solution properties of a protein therapeutic may also reduce immunogenicity, as aggregates have been observed to be more immunogenic than soluble proteins. Additional methods for reducing immunogenicity include removal of potential MHC agretopes and/or T-cell epitopes, and modifications to decrease antigenicity. (See U.S. patent application Ser. No. 11/132,162, entirely incorporated by reference.)

Rational PEGylation

In another preferred embodiment, one or more cysteine, lysine, histidine, or other reactive amino acids are designed into variant adiponectin or gAd proteins in order to incorporate PEGylation sites. It is also possible to remove one or more cysteine, lysine, histidine, or other reactive amino acids in order to prevent the incorporation of PEGylation sites at specific locations. For example, in a preferred embodiment, non-labile PEGylation sites are selected to be well removed from the adiponectin trimerization interface and any required receptor binding sites in order to minimize loss of activity.

Protein Design and Engineering Methods

A number of methods can be used to identify modifications that will yield adiponectin variants with improved solubility, improved soluble expression, and/or retained or improved adiponectin activity. These methods include, but are not limited to, sequence profiling (Bowie and Eisenberg (1991) *Science* 253:164-70), rotamer library selections (Dahiyat and Mayo (1996) *Protein Sci* 5:895-903; Dahiyat and Mayo (1997) *Science* 278:82-7; Desjarlais and Handel (1995) *Prot. Sci.* 4:2006-18; Harbury et al. (1995) *Proc. Nat. Acad. Sci. USA* 92:8408-12; Kono et al. (1994) *Proteins* 19:244-55; Hellinga and Richards (1994) *Proc. Nat. Acad. Sci. USA* 91:5803-7); and residue pair potentials (Jones (1994) Prot. Sci. 3:567-74), all entirely incorporated by reference.

In a preferred embodiment, one or more sequence alignments of adiponectins and related proteins is analyzed to identify residues that are likely to be compatible with each position. In a preferred embodiment, the PFAM, BLAST, or ClustalW alignment algorithms are used to generate alignments of the multi-species adiponectin orthologs, the Clq/TNF-α superfamily, or additional CTRP family members, homologs, orthologs or paralogs. For each variable position, suitable substitutions may be defined as those residues that are observed at the same position in homologous sequences. Especially preferred substitutions are those substitutions that are frequently observed in homologous sequences.

In an especially preferred embodiment, rational design of improved adiponectin variants is achieved by using Protein Design Automation® (PDA®) technology; see U.S. Pat. Nos. 6,188,965; 6,269,312; 6,403,312; 6,708,120; WO98/47089; U.S. Ser. Nos. 09/058,459; 09/127,926; 60/104,612; 60/158,700; 09/419,351; 60/181,630; 60/186,904; 09/782,004; 09/927,790; 60/347,772; 10/218,102; 60/345,805; 60/373,453; 60/374,035; and PCT/US01/218,102, all entirely incorporated by reference.

PDA® technology couples computational design algorithms that generate quality sequence diversity with experimental high-throughput screening to discover proteins with improved properties. The computational component uses atomic level scoring functions, side chain rotamer sampling, and advanced optimization methods to accurately capture the relationships between protein sequence, structure, and function. Calculations begin with the three-dimensional structure of the protein and a strategy to optimize one or more properties of the protein. PDA® technology then explores the sequence space comprising all pertinent amino acids (including unnatural amino acids, if desired) at the positions targeted for design. This is accomplished by sampling conformational states of allowed amino acids and scoring them using a parameterized and experimentally validated function that describes the physical and chemical forces governing protein structure. Powerful combinatorial search algorithms are then used to search through the initial sequence space, which may constitute $10^{50}$ sequences or more, and quickly return a tractable number of sequences that are predicted to satisfy the design criteria. Useful modes of the technology span from combinatorial sequence design to prioritized selection of optimal single site substitutions.

In a preferred embodiment, each polar residue is represented using a set of discrete low-energy side-chain conformations (see, for example, Dunbrack (2002) *Curr. Opin. Struct. Biol* 12:431-40, entirely incorporated by reference). A preferred force field may include terms describing van der Waals interactions, hydrogen bonds, electrostatic interactions, and solvation, among others.

In a preferred embodiment, Dead-End Elimination (DEE) is used to identify the rotamer for each polar residue that has the most favorable energy (see Gordon et al. (2003) *J. Comput Chem.* 24:232-43, Goldstein (1994) *Biophys. J.* 66:1335-40, and Lasters and Desmet (1993) *Prot. Eng.* 6:717-22, all entirely incorporated by reference). In an alternate embodiment, Monte Carlo can be used in conjunction with DEE to identify groups of polar residues that have favorable energies.

In a preferred embodiment, after performing one or more PDA® technology calculations, a library of variant proteins is designed, experimentally constructed, and screened for desired properties. In an alternate preferred embodiment, a sequence prediction algorithm (SPA) is used to design proteins that are compatible with a known protein backbone structure (Raha et al. (2000) *Protein Sci.* 9:1106-19 and U.S. Ser. Nos. 09/877,695 and 10/071,859, all entirely incorporated by reference).

Library Selection

After performing one or more of the above-described calculations, a library comprising one or more preferred modifications may be proposed. The resulting library may be experimentally made and screened to confirm that one or more variants possess desired properties. In a preferred embodiment, the library comprises preferred point mutations identified using at least one of the above-described calculations.

In an alternate embodiment, the library is a combinatorial library, meaning that the library comprises all possible combinations of preferred residues at each of the variable positions. For example, if positions 3 and 9 are allowed to vary, preferred choices at position 3 are A, V, and I, and preferred choices at position 9 are E and Q, the library includes the following six variant sequences: 3A/9E, 3A/9Q, 3V/9E, 3V/9Q, 3I/9E, and 3I/9Q.

In an alternate embodiment, library construction is conducted in a master gAd sequence. The N-terminal truncation point may be at positions including but not limited to 100, 101, 102, 103, 104, 105, 106, 107, 108, 109, 110, 111, 112, 113, 114, 115, 116, 117, 118, 119, 120, 121, 122, 123, 124, 125 and 126. In a more preferred embodiment, the N-terminal truncation point is 108, 109, 110, 111, or 112.

Identifying Suitable Polar Residues for Each Exposed Hydrophobic Position

In a preferred embodiment, solvent exposed hydrophobic residues are replaced with structurally and functionally compatible polar residues. Alanine and glycine may also serve as suitable replacements, constituting a reduction in hydrophobicity. Furthermore, mutations that increase polar character, such as Phe to Tyr, and mutations that reduce hydrophobicity, such as Ile to Val, may be appropriate.

In a preferred embodiment, solvent exposed hydrophobic residues in adiponectin are identified by analysis of a three-dimensional structure or model of adiponectin. In a preferred embodiment, solvent-accessible surface area is calculated using any of a variety of methods known in the art. In a preferred embodiment, solvent accessible surface area is combined with a hydrophobicity index. In a preferred embodiment, a hydrophobicity exposure index (HEI) for each residue is calculated by multiplying the residue's fractional solvent-exposure by the Fauchere and Pliska hydrophobicity index for that amino acid residue type (Fauchere and Pliska (1983) *Eur. J. Med. Chem.* 18:369-75, entirely incorporated by reference). In a preferred embodiment, residues with a positive HEI are selected for modification.

In a preferred embodiment, positions and variants for modification are selected according to the above criteria, and preferred variants produced experimentally then selected empirically, according to improved expression levels.

In another embodiment, preferred suitable polar residues are defined as those polar residues: 1) whose energy in the optimal rotameric configuration, as determined using PDA® technology, is more favorable than the energy of the exposed hydrophobic residue at that position and 2) whose energy in the optimal rotameric configuration is among the most favorable of the set of energies of all polar residues at that position. In one preferred embodiment, the polar residues that are included in the library at each variable position are deemed suitable by both PDA® technology calculations and by sequence alignment data. Alternatively, one or more of the polar residues that are included in the library are deemed suitable by either PDA® technology calculations or sequence alignment data.

Especially preferred modifications to adiponectin include, but are not limited to, the following substitutions: A108D, A108E, A108G, A108H, A108K, A108N, A108Q, A108R, A108S, A108T, Y109D, Y109E, Y109H, Y109K, Y109N, Y109Q, Y109R, V110D, V110E, V110H, V110K, V110N, V110Q, V110R, V110S, Y111D, Y111E, Y111K, Y111N, Y111Q, Y111R, Y122D, Y122E, Y122H, Y122N, Y122R, Y122S, T124I, T124R, I125D, I125E, I125H, I125K, I125N, I125Q, I125R, I125S, M128A, M128D, M128E, M128H, M128K, M128N, M128Q, M128R, M128S, M128T, I135D, I135E, I135H, I135K, I135N, I135Q, I135R, C152A, C152N, C152S, M182A, M182D, M182E, M182K, M182N, M182Q, M182R, M182S, M182T, F184D, F184H, F184K, F184N, F184R, V207D, V207E, V207H, V207K, V207N, V207Q, V207R, V207S, L224D, L224E, L224H, L224K, L224N, L224Q, L224R, L224S, Y225D, Y225E, Y225H, Y225K, Y225N, Y225Q, Y225R, Y225S, D227H, D227K, D227R, D229H, D229K, D229R, and any combination of the above are also a preferred.

One skilled in the art will recognize that the above substitutions can be applied to optimize both full length and fragments of adiponectin as well as used to modify non-human adiponectin orthologs.

Methods of Treatment

Adiponectin may be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York, and U.S. Pat. No. 6,756,196, all entirely incorporated by reference. Examples of routes of administration include parenteral, e.g., intravenous, intradermal, by intravenous (i.v.) infusion, or injected or implanted subcutaneously, intramuscularly, intrathecally, intraperitoneally, intrarectally, intravaginally, intranasally, intragastrically, intratracheally, or intrapulmonarily, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents, antibacterial agents such as benzyl alcohol or methyl parabens, antioxidants such as ascorbic acid or sodium bisulfite, chelating agents such as ethylenediaminetetraacetic acid, buffers such as acetates, citrates, or phosphates, and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the adiponectin variants and polynucleotides of the invention are prepared with carriers that will protect the adiponectin variants and polynucleotides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Examples of sustained-release matrices include polyesters, hydrogels (for example, poly(2-hydroxyethyl-methacrylate), or poly(vinylalcohol)), polylactides (U.S. Pat. No. 3,773,919, entirely incorporated by reference), copolymers of L-glutamic acid and γ-ethyl-L-glutamate, non-degradable ethylene-vinyl acetate, degradable lactic acid-glycolic acid copolymers such as the Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, entirely incorporated by reference.

Suitable carriers are described in the most recent edition of Remington's Pharmaceutical Sciences, entirely incorporated by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions. It is advantageous to formulate oral or parenteral compositions in dosage unit form for ease of administration and uniformity of dosage.

Pharmaceutical compositions can be included in a container, pack, or dispenser together with instructions for administration to form packaged products. For example, a packaged product may comprise a container, an effective amount of an adiponectin variant or polynucleotide of the invention, and an insert associated with the container, indicating administering the compound for treating adiponectin-associated conditions. The pharmaceutical composition may be presented in unit-dose or multi-dose containers, for example sealed ampules, vials or syringes, and may be stored in a freeze-dried (lyophilized) condition requiring only the addition of the sterile liquid carrier, for example water for injections, immediately prior to use. In a preferred embodiment, the pharmaceutical composition is stored in the form of lyophilized formulations or aqueous solutions The invention additionally provides methods for treating adiponectin-associated conditions by administering to a subject in need thereof an effective amount of a composition described above. The treatment methods can be performed alone or in conjunction with other drugs and/or therapies.

In one in vivo approach, a composition containing an adiponectin variant of the invention is administered to a subject. The dosage required depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the different efficiencies of various routes of administration. For example, inhalation administration would be expected to require higher dosages than administration by i.v. injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery.

In some embodiments, polynucleotides such as DNA and RNA are administered to a subject. Polynucleotides can be delivered to target cells by, for example, the use of polymeric, biodegradable microparticle or microcapsule devices known in the art. Another way to achieve uptake of the nucleic acid is using liposomes, prepared by standard methods. The polynucleotides can be incorporated alone into these delivery vehicles or co-incorporated with tissue-specific or tumor-specific antibodies. Alternatively, one can prepare a molecular conjugate composed of a polynucleotide attached to poly-L-lysine by electrostatic or covalent forces. Poly-L-lysine binds to a ligand that can bind to a receptor on target cells. "Naked DNA" (i.e., without a delivery vehicle) can also be delivered to an intramuscular, intradermal, or subcutaneous site. A preferred dosage for administration of a polynucleotide is from approximately $10^6$ to $10^{12}$ copies of the polynucleotide molecule.

In the relevant polynucleotides (e.g., expression vectors), the nucleic acid sequence encoding a sense or an antisense RNA is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses, among others.

In a preferred embodiment, variant adiponectin would be used either alone or in combination therapy for the treatment of adiponectin mediated disorders, e.g., metabolic diseases including but not limited to obesity and the metabolic syndrome (Moller and Kaufman (2005) *Ann. Rev. Med.* 56:45-62, entirely incorporated by reference). Accordingly, the adiponectin variants of the present invention can be used to treat obesity, insulin resistance, glucose intolerance, hypertension, dyslipidemia (hypertriglyceridemia, and low HDL cholesterol levels), coronary heart diseases, and diabetes. Additionally, in this therapeutic mode, variant adiponectin could be used in combination with the following substances: insulin or insulin analogues, PPAR-agonists including but not limited to the TZD or fibrate classes of drugs, any member of the sulfonylurea class of drugs, the insulin-sensitizer metformin, GLP-1 antagonist drugs, HMG-CoA reductase inhibitors, or appetite suppressive agents such as orlistat, rimonobant, or other satiety inducing substances. The combination of adiponectin and any of these additional substances may improve the therapeutic effect of both drugs, especially the combination therapy with insulin.

The following examples are intended to illustrate, but not to limit, the scope of the invention. These examples are not meant to constrain the present invention to any particular application or theory of operation. While such examples are typical of those that might be used, other procedures known to those skilled in the art may alternatively be utilized. Indeed, those of ordinary skill in the art can readily envision and produce further embodiments, based on the teachings herein, without undue experimentation. For all positions discussed in the present invention, numbering is according to full length human adiponectin (SEQ ID NO:1).

EXAMPLE 1

Homology Modeling of Adiponectin Collagen Region

The crystal structure of collagen (Protein Data Bank entry 1K6F) was used as a template to create the model of the trimeric human adiponectin collagen region required for subsequent calculations. Methods well known in the art were used to generate the human homology model.

EXAMPLE 2

Identification of Exposed Hydrophobic Residues in Adiponectin Collagen Region The adiponectin collagen region structure was analyzed to identify solvent-exposed hydrophobic residues. The absolute and fractional solvent-exposed hydrophobic surface area of each residue of each chain was calculated using the method of Lee and Richards ((1971) *J. Mol. Biol.* 55:379-400, entirely incorporated by reference) using an add-on radius of 1.4 Å (Angstroms). The values averaged over all three chains are listed in FIG. 3.

A hydrophobicity exposure index (HEI) for each residue was calculated by multiplying the residue's fractional solvent-exposure by the Fauchere and Pliska hydrophobicity index for that amino acid residue type (Fauchere and Pliska (1983) *Eur. J. Med. Chem.* 18:369-75, entirely incorporated by reference) and listed in FIG. 3.

Solvent exposed hydrophobic residues in the adiponectin collagen region were defined to be hydrophobic residues with at least 50 $Å^2$ (square Angstroms) exposed hydrophobic surface area and HEI values greater than 0.4.

EXAMPLE 3

Identification of Alternative Polar Residues Based on Adiponectin Ortholog Alignment Orthologous adiponectin sequences from mouse (Genbank accession No. Q60994), rat (Genbank accession No. NP653345), rhesus maqaque (Genbank accession No. AAK92202), dog (Genbank accession No. NP001006645), boar (Genbank accession No. NP999535), cow (Genbank accession No. NP777167), and chicken (Genbank accession No. AAV48534) were obtained from NCBI, aligned to the human sequence (Genbank accession No. Q15848, SEQ ID NO:1) using the ClustalW algorithm (Higgins et al. (1994) *Nucleic Acids Res.* 22:4673-80, entirely incorporated by reference) and illustrated in FIG. 2. All alternative amino acid types present among these species at residue numbers 43-97 of FIG. 1 are listed in FIG. 4. From these, possible polar residues were identified.

EXAMPLE 4

Identification of Regions of High Electrostatic Potential in Adiponectin Collagen Region The local electrostatic environment around each amino acid can contribute to the overall stability of the protein. Ideally, stability is conferred, for example, if negatively charged amino acids (e.g., aspartate at neutral pH) lie in areas of positive electrostatic potential and visa versa. Should, for example, an aspartate residue lie in a local environment of negative potential, substituting it with either a positively charged residue or a neutral polar residue may favorably stabilize the protein. This substitution, of course, depends on many structural factors for which the PDA® technology can account. Examining areas of high electrostatic potential may point to regions of the protein requiring optimal residue substitutions to improve overall protein stability.

The electrostatic potential at each position in the adiponectin collagen region was determined using the Debye-Huckel equation in the context of the adiponectin collagen region trimer. Positions in any of the three chains with electrostatic potential greater than 0.5 or less than −0.5 are listed in FIG. 5; modifications at these positions may confer increased stability or receptor binding specificity. Compensating mutations are unnecessary at positions for which the electrostatic potential and the charge of the wild-type amino acid are in agreement; this information is recorded in FIG. 5.

EXAMPLE 5

Replacement of Methionines in Adiponectin to Improve Stability

While oxidation of manufactured protein therapeutics can be dependent on formulation and storage conditions (e.g., temperature and pH), the heterogeneity caused by oxidation can negatively impact clinical efficacy and safety. Adiponectin contains methionine residues at positions 40, 128, 168, and 182. Removal may decrease formulation-dependent heterogeneity and improve storage stability. In a preferred embodiment, adiponectin MET residues are replaced by a group comprising of, but not limited to, ALA, ARG, ASN, ASP, GLN, GLU, HIS, ILE, LEU, LYS, SER, THR, or VAL.

EXAMPLE 6

Replacement of Hydroxyproline in Adiponectin Collagen Region

Collagen-related structural motifs have as their basis the amino acid sequence pattern of . . . [GXY][GXY][GXY] . . . , where X and Y may be an amino or imino acid. Human collagens have a distinct preference for PRO at position Y. Typically a PRO at position Y is post-translationally modified through hydroxylation to hydroxyproline. In contrast, in bacterial collagens, the Y position is preferentially occupied by THR or GLN (Rasmussen et al. (2003) *J. Biol. Chem.* 278(34):32313-6, entirely incorporated by reference) instead of PRO, compensating for the lack of the hydroxylation reaction in bacteria. In FIG. 6, the hydroxyprolines in the adiponectin collagen region are listed, along with appropriate substitutions to improve bacterial expression, stability, and solubility.

EXAMPLE 7

Replacement of [GXY] or [GXYGX'Y'] Repeat Units in Adiponectin Collagen Region Host-guest experiments have found the following sequence motifs to be especially stabilizing in collagen: [GPR], [GER], [GPA], [GDR], [GKD], [GEK], [G_KGD_], [G_KGE_], [GE_G_K], [G_KG_E], [G_LGL_], [GL_GL_] (Persikov et al. (2005) *J. Biol. Chem.* 280(19):19343-9, incorporated entirely by reference), where the "_" character represents a placeholder for any amino or imino acid. In a preferred embodiment, one or more amino acid replacements are made in the adiponectin collagen region to generate one or more of the stabilizing motifs listed.

EXAMPLE 8

Replacement of Aromatic Amino Acids in Non-globular Adiponectin to Improve Stability It has been found that aromatic amino acids (F, H, W, Y) destabilize the collagen triple helix (Persikov et al. (2005) *J. Biol. Chem.* 280(19):19343-9, entirely incorporated by reference). In FIG. 7, the aromatic amino acids in the adiponectin collagen region are listed, along with appropriate substitutions to improve stability.

EXAMPLE 9

Especially Preferred Substitutions

In an especially preferred embodiment, based upon the examples and teachings herein, amino acid substitutions are made from FIG. 8.

EXAMPLE 10

Homology Modeling of Adiponectin Globular Region

The crystal structure of murine gAd (Protein Data Bank entry 1C3H, residues 111-247) was used as a template to create the human model required for subsequent PDA® library calculations as described above. FIG. 2 shows the sequence alignment between murine and human adiponectin sequences. No loop reconstruction was necessary since the alignment shows that no insertions or deletions exist between the globular domains of the two species. The PDA® algorithm was used to generate the human homology model.

EXAMPLE 11

Identification of Exposed Hydrophobic Residues in Adiponectin Globular Region

The gAd structure was analyzed to identify solvent-exposed hydrophobic residues. The absolute and fractional solvent-exposed hydrophobic surface area of each residue of each chain was calculated using the method of Lee and Richards ((1971) *J. Mol. Biol.* 55:379-400, entirely incorporated by reference) using an add-on radius of 1.4 Å (Angstroms). The values averaged over all three chains are listed in FIG. 9. FIG. 10 summarizes the HEI for each position in the gAd structure. FIG. 11 lists a subset of surface exposed hydrophobic amino acids having the highest HEI values and suggested alternative polar residues for each.

A hydrophobicity exposure index (HEI) for each residue was calculated as described in Example 2 and are also listed in FIG. 9. In order to identify positions most likely to impact solubility or soluble expression, solvent exposed hydrophobic residues in human gAd were defined to be hydrophobic residues with at least 50 $Å^2$ (square Angstroms) exposed hydrophobic surface area and HEI values greater than 0.4.

EXAMPLE 12

Identification of Alternative Polar Residues Based on Adiponectin Ortholog Alignment Orthologous adiponectin sequences were aligned to the human sequence (Genbank accession No. Q15848, SEQ ID NO:1) as described in Example 3. All alternative amino acid types present among these species at residue numbers 109-225 of SEQ ID NO:1 are listed in FIG. 12. From these, possible polar residues were identified.

EXAMPLE 13

Identification of Preferred Substitutions to gAd

PDA® technology calculations were performed to identify alternate residues that are compatible with the structure of human adiponectin. At each variable position, energies were calculated for the wild type residue and alternate residues with decreased hydrophobic or increased polar character. Calculations were run using the homology-derived human gAd trimer created in Example 10.

First, point mutation calculations were run for the model along each monomer chain independently; no trimer symmetry was imposed to constrain identical rank orders of amino acids. The energy of each alternate amino acid in its most favorable rotameric conformation was compared to the energy of the wild type residue in the crystallographically observed rotameric conformation; all reported energies in FIG. 13 below are [E(lowest energy variant)−E(subsequent variant)]. In some cases, the wild type residue does not display the lowest energy. Since wt residues at these positions are surface-exposed hydrophobic amino acids and are presumably energetically destabilizing, this result is not surprising. Only polar amino acids exhibiting energies within 2.0 kcal/mol of the lowest energy amino acid are listed in FIG. 13. Results from all three trimer chains are listed and combined into a preferred list of alternative polar residues in FIG. 14. In a preferred embodiment, these substitutions are applied at single positions. In a more preferred embodiment, substitutions are simultaneously made at multiple positions. Coupling of energies for substitutions made at positions close together in three-dimensional space, however, could restrict some combinations of simultaneous substitutions.

EXAMPLE 14

Identification of Regions of High Electrostatic Potential in gAd

The electrostatic potential at each position in gAd was determined using the Debye-Huckel equation in the context of the gAd trimer. Positions in any of the three chains with electrostatic potential greater than 0.5 or less than −0.5 are listed in FIG. 15; modifications at these positions may confer increased stability or receptor binding specificity. In a preferred embodiment, D227 and D229 (average potentials of −0.5 and −0.6, respectively) are replaced with more preferred, positively charged amino acids. The PDA® technology was used to rank substituting D227 and D229 with either ARG, HIS (positively charged assuming formulation is below histidine's pKa of approximately 6.0) or LYS. The energy of each alternate positively charged amino acid in its most favorable rotameric conformation was compared to the energy of the most energetically favored residue; all reported energies in FIG. 16 are [E(lowest energy variant)−E(subsequent variant)]. All reported energies are within 1.5 kcal/mol of the lowest energy amino acid. In a preferred embodiment, D227 and/or D229 are substituted by a group comprising of, but not limited to, ARG, HIS and LYS.

EXAMPLE 15

Replacement of the Free Cysteine in gAd

The globular portion of adiponectin contains a single free cysteine at position 152. While C152 is not exposed to solvent in the crystal structure (the solvent accessible surface area averaged over all three chains is 1.1 $Å^2$), the residue is located in an exterior loop and may be subject to local flexibility. In a preferred embodiment, removal of this cysteine may decrease non-specific disulfide formation and aggregation, and improve overall protein storage stability.

The energy of each alternate amino acid in its most favorable rotameric conformation was compared to the energy of the wild type cysteine residue; all reported energies in FIG. 17 are [E(CYS)−E(subsequent variant)]. In this case, the wild type residue does display the lowest energy. Only amino acids exhibiting energies within 5.0 kcal/mol of the lowest energy amino acid are listed. In a preferred embodiment, C152 is replaced by a group comprising of, but not limited to, ALA, ASN, SER, THR, and VAL.

EXAMPLE 16

Replacement of Methionines in gAd to Improve Stability

The globular portion of adiponectin contains three methionine residues (128, 168 and 182), two of which are exposed to solvent (128 and 182 with solvent accessible surface areas averaged over all three chains of 46.5 $Å^2$ and 43.7 $Å^2$, respectively) and may be prone to oxidation. Therefore, removal of these may decrease formulation-dependent heterogeneity and improve storage stability.

The energy of each alternate amino acid in its most favorable rotameric conformation was compared to the energy of the most energetically favored residue; all reported energies in FIG. 18 are [E(lowest energy variant)−E(subsequent variant)]. Only amino acids exhibiting energies within 4.0 kcal/mol of the lowest energy amino acid substitution are listed. In a preferred embodiment, MET 128 and 182 are replaced by a group comprising of, but not limited to, ALA, ARG, ASN, ASP, GLN, GLU, HIS, LYS, SER or THR.

EXAMPLE 17

Identification of Preferred Coupled Substitutions to Adiponectin

As discussed above, interaction energies for substitutions made at positions close together in three-dimensional space may restrict the identities of favorable amino acid combinations. In a preferred embodiment, positions comprising of the group of surface-exposed hydrophobic residues described in Example 11 and located within a sphere of 6 Å are identified and subjected to simultaneous design and optimization using the PDA® technology. Of positions 109, 110, 111, 122, 125, 135, 184, 207, 224, 225 described above, the following three groups are clusters of residues located within a 6 Å sphere of one another: 1) Y109, V110, and Y111, 2) Y122 and I125, and 3) L224 and Y225. The remaining positions (135, 184 and 207) are not located within 6 Å of any other surface-exposed hydrophobic residues identified in Example 11.

The energy of each alternate amino acid in its most favorable rotameric conformation was compared to the energy of the most energetically favored residue; all reported energies in FIG. 19, FIG. 20 and FIG. 21 are [E(lowest energy variant combination)−E(subsequent variant combination)]. Only polar amino acids were considered during the calculations and only amino acid combinations exhibiting energies within 2.0 kcal/mol of the lowest energy amino acid substitutions are listed. As in other examples, difference energies are listed for chains A, B and C. The residue combinations are sorted by the number of chains in which the listed substitution is energetically favored. In a preferred embodiment, substitution combinations are chosen that are energetically favorable in at least one of three chains. In a more preferred embodiment, substitutions are chosen that are favored in two of three chains. In a further preferred embodiment, substitutions are chosen that are favored in all three chains.

EXAMPLE 18

Core Design of gAd

Figure 23:
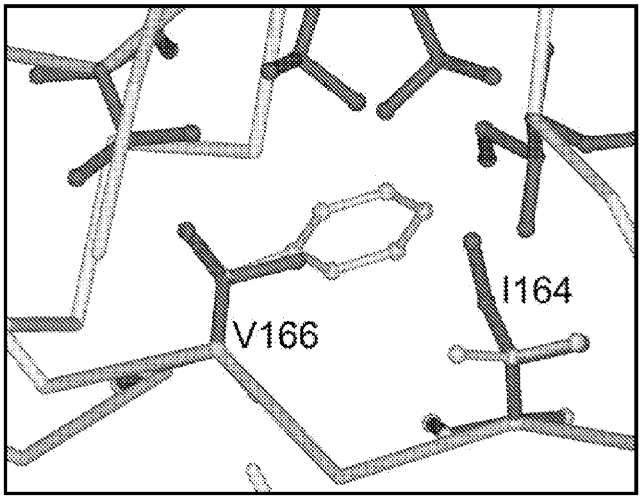
FIG. 23 shows three-dimensional structure of low energy core design of globular adiponectin domain (2nd lowest energy sequence solution in FIG. 22. Dark grey balls-and-sticks depict wild type side-chains (I164 and V166) in their native conformations while light grey atoms depict low-energy amino acid substitutions I164V and V166F. SEQ ID NO:1

Optimization of packing interactions within the core of protein therapeutics has the potential to increase thermal stability, decrease aggregation, increase storage shelf-life and improve pharmacokinetics (Luo et al. (2002) *Proteins* 11: 1218-26, entirely incorporated by reference). Buried hydrophobic residues (<5 $Å^2$ solvent accessible surface area averaged over all three chains) were identified as potential core residues. Hydrophobic residues located at the trimer interface were excluded from consideration. The first shell of buried core residues were defined as, but not limited to, F115, V123, I130, F132, F150, F160, I164, V166, V171, V173, L175, L205, V211, L213, V215 and F234. These 16 residues were simultaneously subjected to optimization using the PDA® technology. Only substitutions with the following hydrophobic residues were considered: F, I, L, V and W. In a preferred embodiment, all non-polar amino acids are considered as energetically suitable substitutions. The top 100 sequence solutions are listed in FIG. 22 and are ranked by their energies relative the lowest energy sequence variant (E(lowest energy variant combination)−E(subsequent variant combination)). Solution #2 (I164V/V166F) is ~2.5 kcal/mol lower in energy than the native sequence and is depicted in FIG. 23; substitution of V166 with PHE required losing a methyl group from position 164. In another preferred embodiment, additional buried residues could be included in the calculation such as residues V117, L119, I154 and L238. In another preferred embodiment, optimization can occur at single core positions or in combinations.

EXAMPLE 19

Rational PEGylation of gAd

Figure 24:
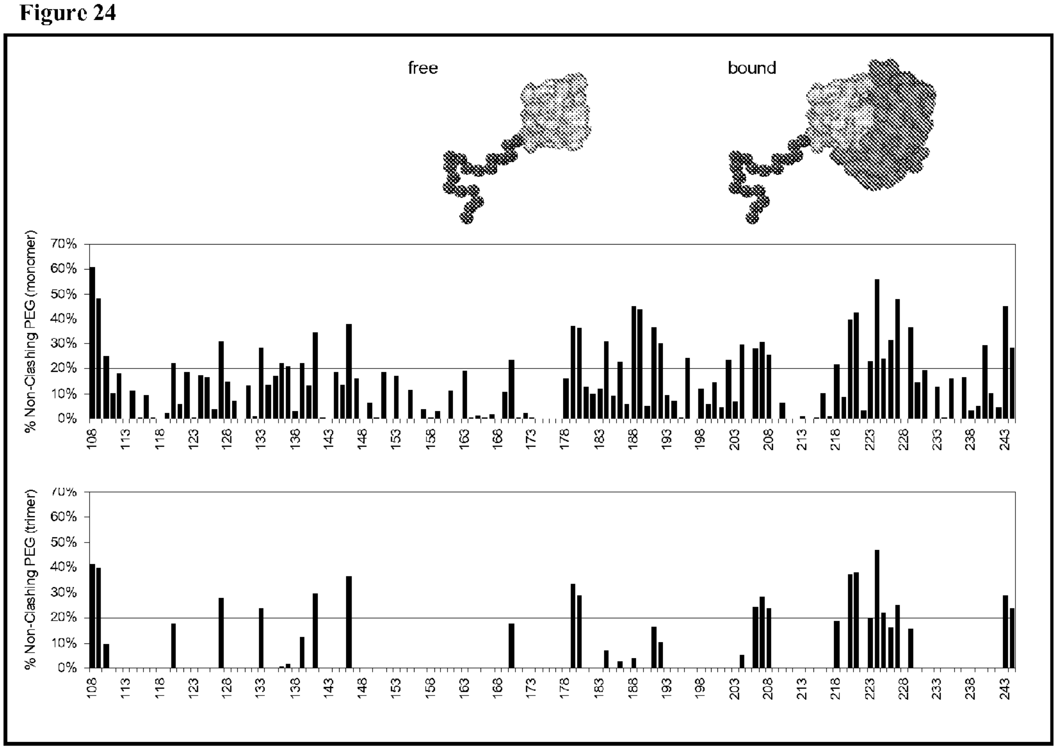
FIG. 24 shows optimization of PolyEthylene Glycol (PEG) sites for adiponectin using a PEG of molecular weight of 2000 and using a cysteine-maleimide attachment moiety. SEQ ID NO:1

The methods of the present invention have been used to select optimal PEGylation sites in gAd based on the atomic coordinates generated in Example 10. The simulation data was first analyzed to identify sites with high coupling efficiency. For PEG2000, sites for which greater than 20% of the simulated PEG chains are non-clashing in the free state are considered optimal sites for attachment (see FIG. 24, top chart). These sites include A108, Y109, V110, E120, N127, T133, F136, Y137, Q139, N141, S146, D170, D179, K180, F184, Y186, Q188, Y189, E191, K192, Q196, L202, H204, E206, V207, G208, D218, E220, R221, G223, L224, Y225, A226, D227, D229, Y240, T243, and N244.

The predicted high coupling efficiency sites were further screened to identify which of these sites retain PEG range of motion upon receptor binding. For PEG2000, sites for which greater than 20% of the simulated PEG chains are non-clashing in the bound state are preferred (see FIG. 24). These sites include A108, Y109, N127, T133, N141, S146, D179, K180, E206, V207, G208, E220, R221, G223, L224, Y225, D227, T243, and N244. For PEG2000, sites for which greater than 30% of the simulated PEG are not clashing in the bound state are especially preferred. These sites include A108, Y109, S146, D1179, E220, R221, and L224.

In a preferred embodiment, site specific PEGylation at any of these or other positions would either require replacement of the native amino acid with a suitable amino acid such as cysteine or the introduction of an unnatural amino acid such as p-acetyl-L-phenylalanine.

In another preferred embodiment, a bivalent PEG could be used to form a link between two gAd molecules. This may replace the collagen-like domain and form a hexameric gAd unit of two trimeric gAd units.

EXAMPLE 20

Construction and Expression of Variant gAd with Improved Solubility

Standard molecular biology methods were employed to construct an expression library of globular adiponectin variants. Briefly, gAd cDNA (encoding amino acids 110-244) was subcloned into the bacterial expression vector pET-17b (FIG. 25). Site directed mutagenesis was performed using standard methods to generate the 34 single amino acid substitution variants listed in FIG. 26.

We used standard protein expression and analysis methods to express the single amino acid gAd variants listed in FIG. 26. Briefly, we generated a fresh lawn of colonies of gAd variants in BL21 Star (DE3) cells and the entire lawn was harvested and used to inoculate a 50 mL starter culture for each clone. Cultures were grown at 37° C. until they reached an optical density ($OD_{600}$) of 0.6 in approximately 1.5 hours. The cultures were cooled to room temperature, induced with 0.5 mM IPTG, and grown for approximately 16 additional hours in a shaker set to room temperature. The cultures were harvested, $OD_{600}$ was measured, and bacterial pellets were prepared by centrifugation at 6000 rpm for 15 minutes. The supernatant was discarded and the pellet was solubilized using BugBuster HT (a proprietary detergent-containing bacterial lysis reagent). Soluble and insoluble lysate fractions were fractionated using high speed centrifugation and analyzed by SDS-PAGE using standard electrophoresis methods.

SDS-PAGE loading is as shown in FIG. 27*a*. FIG. 27*b* features nine SDS-PAGE gels that were loaded with equal amounts of the soluble and insoluble fractions of the 34 single amino acid substitution variants. Globular adiponectin is a 134 amino acid polypeptide with a molecular mass of ~15 kD. In FIG. 27*b*, gAd is highlighted by an arrow on the left hand margin.

When gAd-expressing cells are lysed under these detergent-containing conditions (i.e,. BugBuster), the native gAd is found to be only <10% soluble (FIG. 27*b*, lanes 12-13 and 40-41). We identified several variants that had improved protein solubility or soluble expression under these expression and lysis conditions. Variants Y122H (FIG. 27*b*, lanes 66 and 75), Y122S (FIG. 27*b*, lanes 22-23), I125E (FIG. 27*b*, lanes 32-33), I125H (FIG. 27*b*, lanes 42-43), I125T (FIG. 27*b*, lanes 50-51), F184H (FIG. 27*b*, lanes 69-70), V207E (FIG. 27*b*, lanes 16-17), and V207K (FIG. 27*b*, lanes 26-27) all had solubility or soluble expression equal to or in many cases far greater than native gAd.

EXAMPLE 21

Solubility or Soluble Expression Analysis of Select Globular Adiponectin Single Amino Acid Substitution Variants in the Absence of Detergent Variants Y122H, Y122S, I125E, I125H, I125T, F184H, V207E, and V207K were selected based on their improved solubility properties as judged from the pilot expression studies described above. In order to demonstrate that these variants have truly improved solubility, it was necessary to measure the amount of soluble protein generated when bacteria expressing these protein are lysed in the absence of detergent. Solubility in the absence of detergent is recognized a more rigorous measure of soluble protein and it enables future downstream process modifications and may lead to a streamlined manufacturing process.

The variants were expressed as described above except that the vessel volume was scaled up ten-fold (500 mL in a 2000 mL flask). After overnight induction at 4° C., the cells were harvested by centrifugation and the pellets were stored at −80° C. The cell pellets were mixed with detergent-free lysis buffer (20 mM BisTris pH 6.0, 1 mM EDTA, 0.5 mM DTT) and lysed by sonic disruption. The resulting material was cleared by high-speed centrifugation, and the resulting cleared soluble and insoluble fractions were volume normalized and analyzed using SDS-PAGE. This approach allows the determination of the improvement of overall protein expression/yield as well as solubility. The gels were loaded as described in FIG. 28*a*, FIG. 28*b* shows three SDS-PAGE gels that contained the soluble and insoluble fractions of native gAd, empty vector (pET-17b), or the selected variants. An arrow on the left hand margin of the figure points to the gAd controls.

When the gAd-expressing cells were lysed with detergent-free conditions, the native gAd was found to be virtually insoluble (FIG. 28*b*, lanes 76-78, 85-86, and 99-A). All the variants tested had dramatically improved solubility in the absence of detergent. Especially favorable in this regard were the substitutions I125E, I125T, and Y122H. Furthermore, since these samples were volume normalized, we identified numerous variants with significantly improved protein expression yields. Variants F184H, I125H, and V207E had the greatest effect on increasing gAd protein yields.

EXAMPLE 22

Construction and Expression Analysis of Double Variant Globular Adiponectin Proteins The eight globular adiponectin amino acid substitutions that gave increased solubility and expression yields were combined in pair wise combination to generate a library of adiponectin double variants. The same molecular biology techniques and codons as described above were used to generate the following double mutant globular adiponectin variants; Y122H/I125E, Y122H/I125H, Y122H/I125T, Y122H/F184H, Y122H/V207E, Y122H/V207K, Y122S/I125E, Y122S/I125H, Y122S/I125T, Y122S/F184H, Y122S/V207E, Y122S/V207K, I125E/F184H, I125E/V207E, I125E/V207K, I125H/F184H, I125H/V207E, I125H/V207K, I125T/F184H, I125T/V207E, I125T/V207K, F184H/V207E, F184H/V207K. These proteins were expressed and processed as described above in Example 20. After detergent-induced lysis, we compared the relative amount of soluble protein with the total and insoluble fractions. The gels were loaded as described in FIG. 29*a*, FIG. 29*b* shows 11 SDS-PAGE gels that contained the expression and solubility information for the double mutant globular adiponectin variants. As an experimental control, single mutants and native globular adiponectin were included, as well as an empty vector control. On the SDS-PAGE, an arrow highlights the position of globular adiponectin.

Several of the double mutant proteins had dramatically improved expression and solubility properties. Of the 23 double variant proteins tested, variants Y122H/F184H, Y122S/I125E, Y122S/I125H, Y122S/V207K, I125E/V207E, I125E/V207K, I125H/F184H, I125T/F184H, and F184H/V207K had dramatic improvements. Starting with the purified product from SEC, gAd Y122S/I125E variant was pooled from two fractions to start with a concentration of 9 mg/mL, and was concentrated to 60 mg/mL. The gAd Y122S/I125E variant remained soluble after one week when stored at 4° C. in 10 mM $PO_4$, 150 mM NaCl buffer.

Wild-type gAd appears to have a solubility of approximately 0.5 mg/mL at 4° C. in aqueous buffer. While the maximum of solubility for the gAd variants described herein has not been determined, 60 mg/mL for gAd Y122S/I125E is at least a 50- to 100-fold increase in solubility relative to wild-type.

EXAMPLE 23

Solubility Analysis of Select Globular Adiponectin Double Amino Acid Substitution Variants in the Absence Of Detergent Variants Y122H/F184H, Y122S/I125E, Y122S/V207K, I125E/V207E, I125E/V207K, I125H/F184H, I125T/F184H, and F184H/V207K were subjected to the same protein solubility analysis as described in Example 21. FIG. 30*a* shows the SDS-PAGE loading for the lysates prepared from the double variants and native proteins, the highest expressing single variant F184H was included as an additional control. FIG. 30*b* shows two SDS-PAGE gels that contained the results of the solubility analysis in the absence of detergent. Upon lysis of the bacteria by sonication, there is an increase of both total and soluble protein released for the gAd double variants when compared to the native protein.

The majority of these variants have a nearly equal partitioning of protein between the soluble and insoluble fractions, suggesting approximately 50% solubility. Variants Y122H/F184H, I125T/F184H, and I125E/V207K appear to have even greater than 50% solubility. Finally, when compared to the native protein, there is a several orders of magnitude increase in the amount of total expressed and soluble globular adiponectin.

Figure 31B:
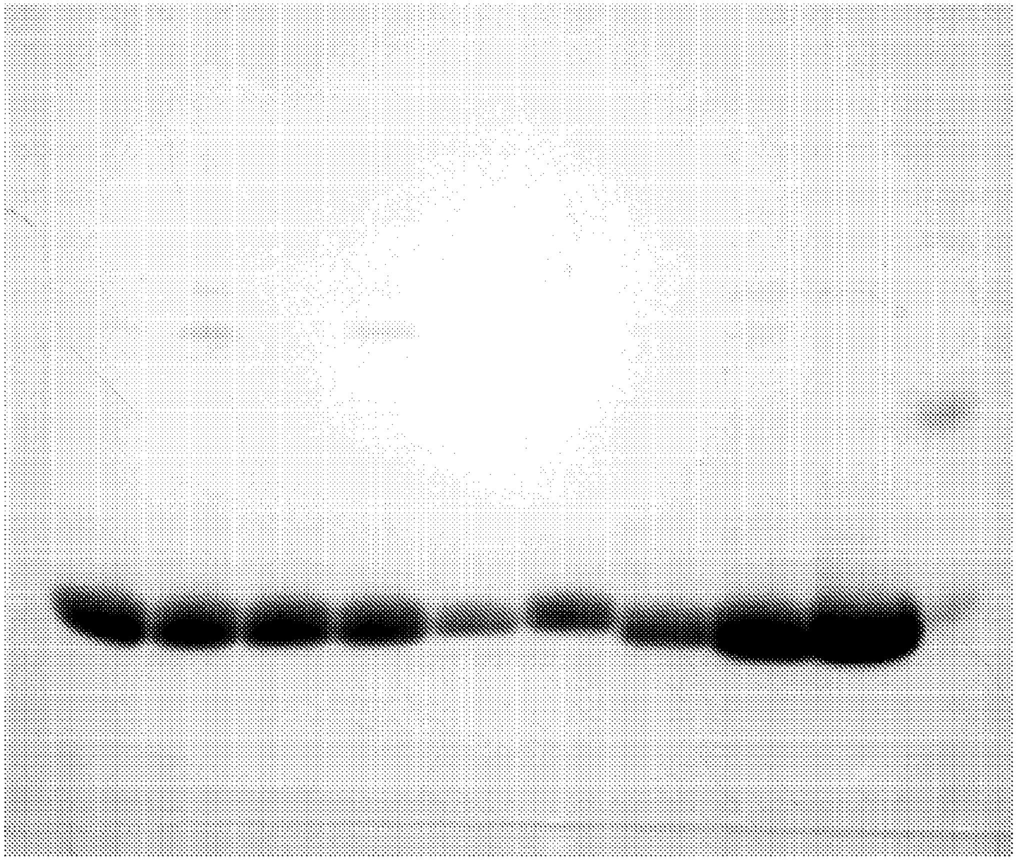
FIG. 31B is a table of soluble gAd variants showing in FIG. 31A. SEQ ID NO:1

FIG. 31*a* shows an SDS-PAGE of relative purification levels of the gAd variants listed in FIG. 31*b*. Variants I125E/V207K and I122S/I125E showed the greatest amount of protein after purification.

FIG. 32 shows an SDS-PAGE that contained the detergent-free soluble lysates from native and I125E/V207E gAd. The native gAd and variant gAd lysates were both diluted 12.5-fold, the variant gAd lysate was additionally diluted 2- to 128-fold compared to the native gAd lysate. It is clear from this analysis that there is more than a 100-fold difference in the amount of soluble protein generated by the I125E/V207E gAd variant relative to native gAd.

EXAMPLE 24

Solubility Analysis of Select gAd C152 Variants

Figures 33A, 33B:
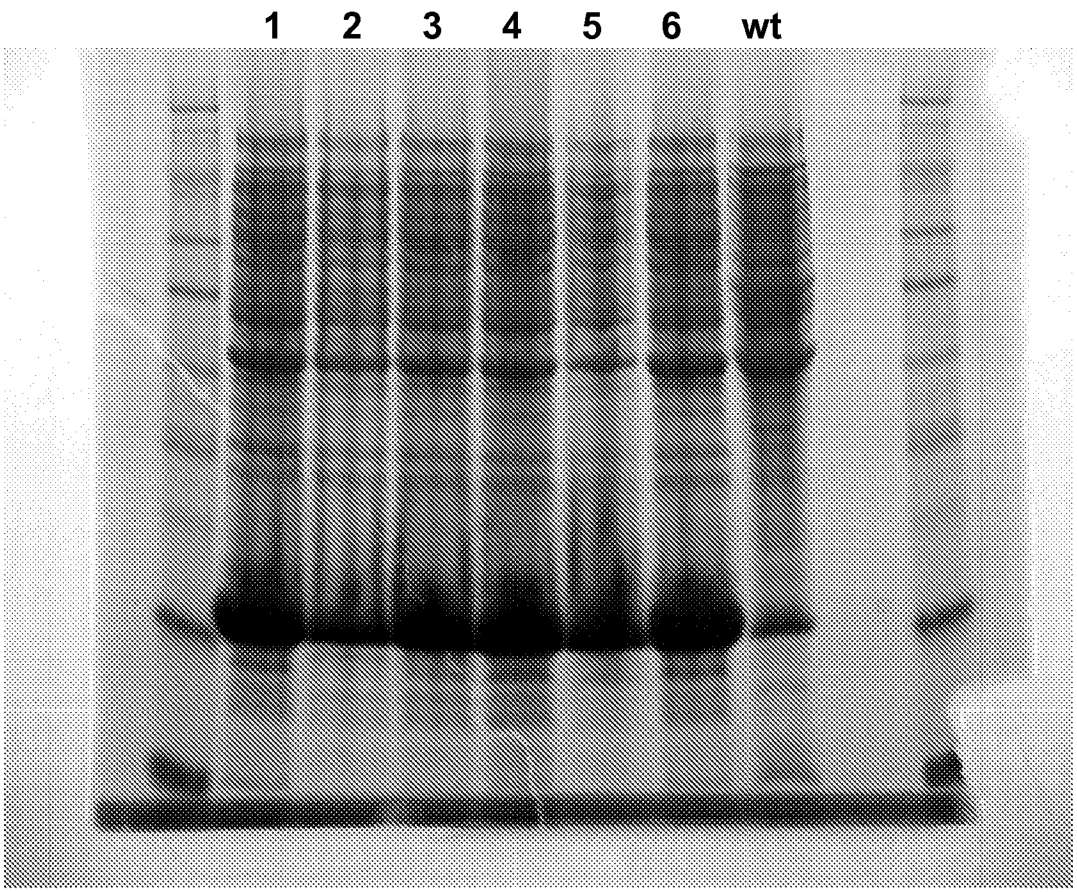
FIG. 33A shows SDS-PAGE gel of total protein expression of I125E/V207E/C152x variants.
FIG. 33B is a table of gAd variants in FIG. 33A. SEQ ID NO:1
Figures 34A, 34B:
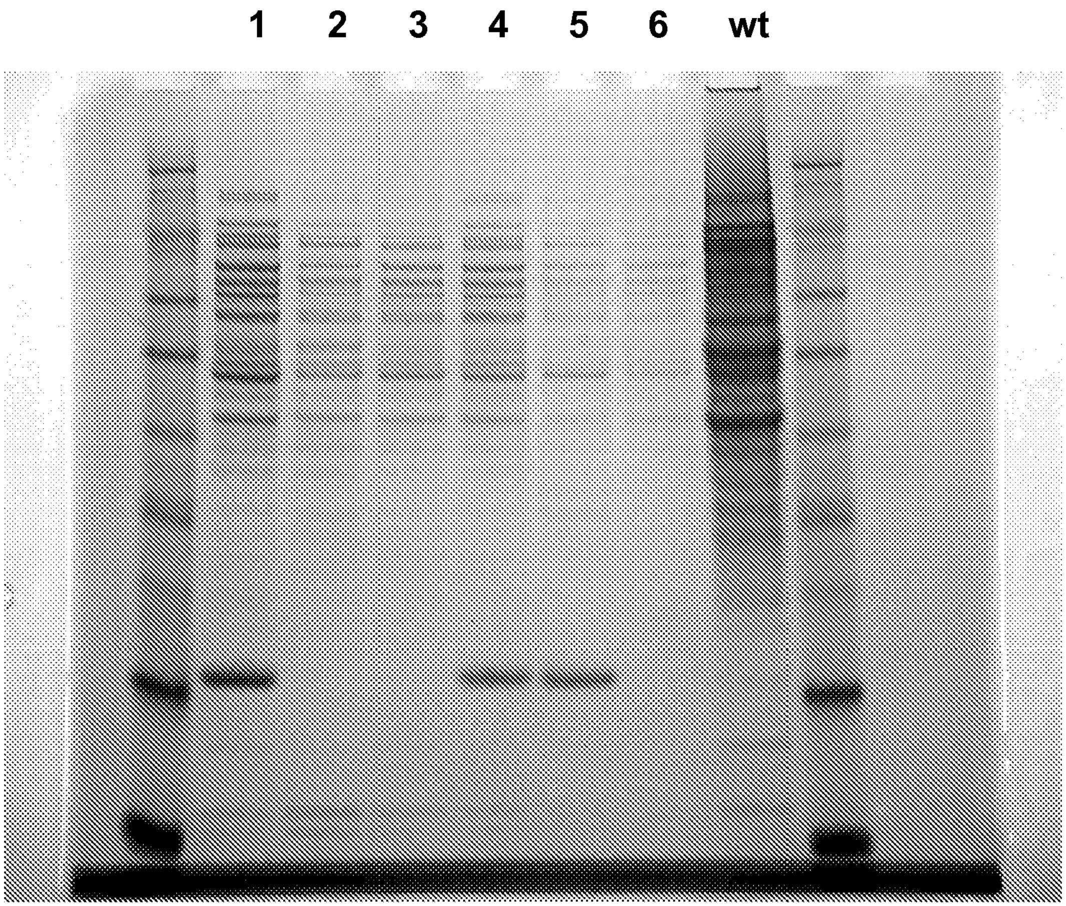
FIG. 34A shows SDS-PAGE gel of soluble protein of I125E/V207E/C152x variants.
FIG. 34B is a table of soluble gAd variants in FIG. 34A. SEQ ID NO:1

Variant I125E/V207E was used as a background for making six C152 variants, C152A, C152F, C152L, C152S, C152T and C152V. The variants were made and expressed as described in Example 20 and subjected to the same protein solubility analysis as described in Example 21. FIG. 33A and FIG. 34A show an SDS-PAGE that contained the detergent-free soluble lysates from the variants listed in FIG. 33B.

EXAMPLE 25 gAd Double Variants Induce AMPK Phosphorylation in Differentiated Mouse C2C12 Cells To measure the biological activity of select gAd variants, it was necessary to purify the recombinant gAd proteins away for the *E. Coli* host cell contaminants. We developed a conventional chromatography process that consisted of three separate column steps. Briefly, gAd variants were grown and processed into lysate as described in Example 20, the soluble fraction was applied to a DEAE column and eluted with an isocratic step at 200 mM NaCl. This material was passed over Q column as a non-binding step (i.e., the gAd flowed through the column but protein contaminants and endotoxin were bound), and finally polished using a preparative S-100HR gel filtration column. For the gAd variants this process would routinely yield 100-300 mg of purified protein per liter of *E. Coli* culture.

Figure 36:
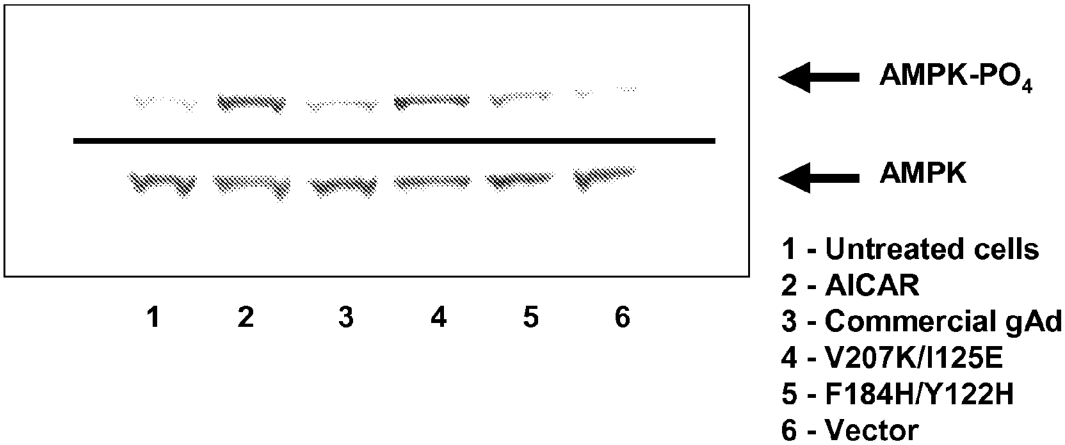
FIG. 36 shows treatment of C2C12 myotubes with gAd variants and controls. SEQ ID NO:1

We used C2C12 cells differentiated into myotubes to measure gAd-induced phosphorylation of AMP Kinase (AMPK). Murine C2C12 cells were grown in culture as described by the ATCC. Differentiation was induced by transferring the cells to a growth media containing 2% horse serum. The cells were maintained in this media for up to seven days. During this time, the cells elongated and fused together to form polynuclear myotubes that visibly twitched when observed under light microscopy. FIG. 35 shows a series of phase contrast microscopy images that show a low magnification (10×) view of the differentiation process at days 1, 3, 4, and 7. A high magnification view of the cells at day 4 clearly shows the presence of multi-nucleated tubular structures. C2C12 myotubes were left as is or treated with 30 μg/mL of the double amino acid gAd variants I125E/V207K and Y122H/F184H for 60 minutes. As controls for this experiment, myotubes were also treated with 30 μg/mL commercial native gAd (BioVision; Mountain View, Calif.). AICAR (a chemical activator of AMPK) was used as a positive control and an empty vector control lysate (that was processed through the identical chromatography scheme as the gAd variants) was used as the negative control. After treatment, the C2C12 cells were processed into lysate and the amount of both total AMPK and phosphorylated AMPK (pAMPK) was determined by Western blotting with either total or phosphorylation site-speicific AMPK antibodies. FIG. 36 shows that the positive control, AICAR, induced a potent increase in pAMPK, while untreated cells and the vector did not. Commercial native gAd generated a mild increase in pAMPK and the two engineered gAd variants were even more effective. From this experiment we conclude that the gAd variants I125E/V207K and Y122H/F184H have retained biological activity at least equal to or greater than native gAd.

Figure 37:
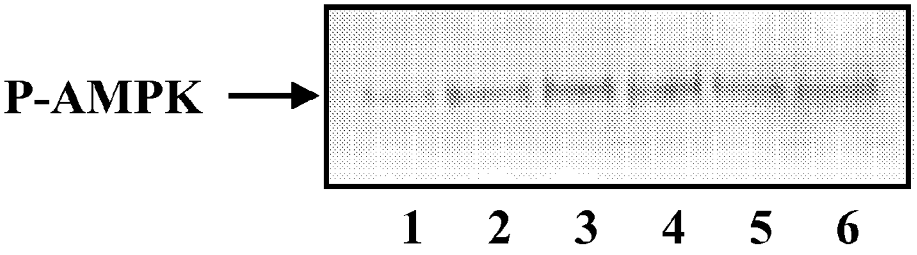
FIG. 37 shows that treatment of differentiated human muscle cells with gAd variants induces AMPK phosphorylation. SEQ ID NO:1

EXAMPLE 26 gAd Double Variants Induce AMPK Phosphorylation in Differentiated Human Muscle Cells The ability of gAd variants to induce pAMPK in differentiated human muscle cells was measured. Pre-screened Human Skeletal Muscle Cells (HSkMC) were obtained from Cell Applications, Inc. and propagated in Skeletal Muscle Cells Growth Medium according to the manufacturer's instructions. To induce differentiation of HSkMC into myotubes, the medium of 90% confluent cell cultures in 6-well plates was replaced by appropriate volume of Skeletal Muscle Differentiation Medium from the same supplier. Differentiation Medium was changed every other day and multinucleated myotubes were observed by the fourth day of differentiation. Differentiation Medium was finally changed 18 hours prior to gAd treatment. On the day of gAd treatment, the cells were washed and incubated in Skeletal Muscle Cells Growth Medium for three hours prior to the addition of adiponectin variants. HSkMC myotubes were left untreated or treated with 50 μg/mL of the gAd variants F184H, I125H/F184H, I125T/F184H, I125E/V207K, and Y122S/I125E for 15 minutes. After the incubation, cells were washed two times with ice-cold PBS, then 200 ml of pre-heated (90° C.) 1×SDS sample buffer supplemented with phosphatase inhibitors was added to each well and the plates were placed on a shaker for two minutes to solubilize the cells and generate a crude cell lysate. This material was harvested and transferred to 1.5 mL eppendorf tubes, heated for an additional 10 minutes at 95° C. and stored overnight at −20° C. On the next day, samples were thawed and passed through a 27-gauge syringe three times followed by centrifugation at 20000 g for 15 min. 20 ml of each sample was loaded on NuPAGE 7% Tris-Acetate Gel (1.0 mm×10 well) and the gels were run in Tris-Acetate buffer at 150 V constant for 80 min. Upon completion, the gels were incubated in 2× transfer buffer with 0.01% SDS for 20 min followed by transfer to PVDF membranes using 100 V constant for 1 hour. PVDF membranes were incubated with TBS+Tween 20 blocking buffer for 20 min. Anti-Phospho-AMPK antibodies were added in 1:1000 dilution in TBST buffer and membranes were incubated O/N at 40° C. After washes (3 times, 15 min each), membranes were treated with alkaline phosphatase-coupled secondary antibodies for 1 hour at room temperature. Proteins were visualized by using NBT/BCIP alkaline phosphatase substrate. The results of this experiment are presented in FIG. 37; all the variants tested produced an approximately two-fold increase in pAMPK levels relative to the untreated control.

EXAMPLE 27

Identification of Preferred Substitutions to gAd Using PDA® Technology

PDA® technology calculations were performed to identify alternate residues that are compatible with the structure of human gAd. At each position, energies were calculated for the wild-type residue and alternate residues.

Point mutation calculations were run for the model along each monomer chain independently. The energy of each alternate amino acid in its most favorable rotameric conformation was compared to the energy of the wild-type residue; all reported energies in FIG. 38 are the average of [E(wild-type)−E(variant)]. Only amino acids exhibiting energies with better energy than wild-type amino acid (<0.0 kcal/mol) are listed in FIG. 38.

EXAMPLE 28

Identification of Hydrophobic Surface Patches in Adiponectin Collagen Region Variants of adiponectin Y122H, Y122S, I125E, I125H, I125T, F184H, V207E, and V207K were previously shown to have improved solubility properties. Recent work by Shanahan and Thornton (Shanahan and Thornton (2004) *Bioinformatics.* 20:2197-204; Shanahan and Thornton (2005) *Biopolymers.* 78:318-28, both entirely incorporated by reference) has shown that instead of looking at single exposed hydrophobic residues, it is also useful to analyze the extent of hydrophobic patches on the surface of proteins. Therefore, we have added a third term "proximity" to our original analysis and analyze hydrophobic surface patches by calculating a "residue hydrophobic density (RHD)":

$$RHD_i = \sum_i proximity_i * \text{solvent\_exposure}_i * hydrophobicity_i$$

The globular adiponectin domain was analyzed to identify hydrophobic surface patches by calculating the RHD for each residue as defined above. The absolute and fractional solvent-exposed hydrophobic surface area of each residue of each chain was calculated using the method of Lee and Richards ((1971) *J. Mol. Biol.* 55:379-400, entirely incorporated by reference) using an add-on radius of 1.4 Å (Angstroms). Hydrophobic surface patches comprising the improved variants were identified by modeling mutations at each variant position using Protein Design Automation® (PDA®) technology and identifying the residues affected by said mutation. Using this method the hydrophobic surface patches containing the improved solubility variant positions were identified and are listed in FIG. 39.

By engineering mutations at positions in the hydrophobic surface patch it is possible to lower the hydrophobicity score (RHD score) of the patch to one that is equal to or more favorable than the previously identified variants. PDA® technology was used to construct all possible mutations at each position in the identified hydrophobic surface patch and the mean RHD for the patch was calculated. Those variants that have mean RHD patch values equal to or lower than the previously identified variant, and are thus predicted to have improved solubility and other properties, are listed in FIG. 40.

For each predicted favorable variant, energies were calculated with PDA® technology for the wild type residue and alternate residues which decreased the RHD for the hydrophobic patch. Calculations were run using the homology-derived human gAd trimer. First, point mutation calculations were run for the model along each monomer chain independently; no trimer symmetry was imposed to constrain identical rank orders of amino acids. The energy of each alternate amino acid in its most favorable rotameric conformation was compared to the energy of the wild type residue in the crystallographically observed rotameric conformation. The calculated energies are listed in FIG. 41.

EXAMPLE 29 gAd Variants Antagonize cAMP-induced Lipolysis in Primary Human Adipocytes

In adipocytes, the breakdown of triglycerides into free fatty acids (FFA) leads to either FFA release into the circulation or the cells consume the FFAs via fatty acid oxidation. Since circulating FFAs induce insulin resistance in both in vitro and in vivo experimental systems it follows that triglyceride breakdown inhibitors may provide an effective therapy for the treatment of metabolic disease. Even more desirable are compounds that induce triglyceride breakdown with the FFAs being consumed via the fatty acid oxidation pathway, such compounds would both reduce circulating FFAs and promote weight loss. Our studies demonstrated that gAd and the gAd variants described in this invention effectively induce AMPK activation and AMPK is known to negatively regulate lipolysis by inhibiting the activity of key lipolytic enzymes. Thus we measured the ability of gAd to inhibit agonist-induced lipolysis in differentiated primary human adipocytes.

Pooled primary human preadipocytes (Zen-Bio, lot# SL0028, average age—43, gender—female, average BMI—27.25) were differentiated for two weeks. The cells were washed in PBS and exposed to either vehicle or increasing doses of gAd variants for 2 hours, at which time 1 μM isoproterenol was added to induce lipolysis for an additional three hours. After treatment the culture media was assayed for non-esterified fatty acids (NEFA) using a standard spectroscopic assay. The results of these studies showed that pretreatment of differentiated primary human adipocytes with the four tested gAd variants could inhibit isoproterenol-induced lipolysis. Of these variants I125E/V207K appeared the most effective in this assay, see FIG. 42.

EXAMPLE 30 gAd Y122S/I125E Induction of Glucose Uptake in Primary Human Adipocytes

AMPK activation is known to promote the mobilization of glucose transport protein to the cell surface to promote glucose uptake. To determine if gAd-stimulated AMPK could promote glucose uptake we treated differentiated primary human adipocytes with increasing doses of gAd and measured radioactive glucose (2-DOG) uptake.

Pooled primary human preadipocytes (Zen-Bio, lot# SL0028, average age—43, gender—female, average BMI—27.25) were differentiated for two weeks. The cells were incubated overnight in glucose-free media, washed in PBS and exposed to either vehicle, insulin, or increasing doses of gAd Y122S/I125E for 2 hours followed by an additional 2 hour treatment with a cocktail of radioactive (2-DOG) and cold glucose (FIG. 43, open bars). In a parallel experiment we used AraA, a known chemical inhibitor of AMPK to determine if AMPK mediates the Y122S/I125E-induced glucose uptake (FIG. 43, gray bars). To measure glucose uptake after treatment the cells were washed, lysed, and intracellular 2-DOG was measured using liquid scintillation counting. The results of these studies showed that pretreatment of differentiated primary human adipocytes with increasing doses Y122S/I125E induced glucose uptake with similar efficacy to the insulin control. AraA treatment inhibited gAd-induced glucose uptake suggesting that gAd-induced AMPK is essential for gAd-stimulated glucose uptake, FIG. 43. AraA treatment had no effect on insulin-stimulated glucose uptake.

EXAMPLE 31

Time Course and Dose Response of gAd Y122S/I125E-Induced AMPK and ACC Phosphorylation in L6 Myotubes FIGS. 44-46 show Western blots that measure AMPK phosphorylation and ACC phosphorylation in differentiated rat L6 myotubes treated with either a time course (FIGS. 44 and 46) or dose response (FIG. 45) of gAd Y122S/I125E. Rat L6 cells were induced to differentiate during a four day culture. The cells were treated with either 100 μg/mL Y122S/I125E for 5 to 15 minutes; or 10, 50, or 100 μg/mL Y122S/I125E for 15 minutes. AICAR was used a positive control for these experiments. After treatment the cells were processed for SDS-PAGE followed by western blot with phosphorylation site-specific antibodies to AMPK and ACC. The western blots demonstrate that both AICAR and Y122S/I125E induced a dose-dependent phosphorylation of AMPK and ACC within 5 minutes of treatment.

EXAMPLE 32

Dose Response and Time Course of gAd Y122S/I125E-Induced AMP Kinase Activity gAd Y122S/I125E treatment of differentiated rat L6 myotubes increases AMP Kinase activity. Rat L6 cells were induced to differentiate during a four day culture. Rat L6 myotubes were treated with either a time course (5, 15, 30, or 60 minutes) of 5 μg/mL Y122S/I125E or a dose response (5, 10, or 50 μg/mL) of gAd Y122S/I125E; and measured for AMPK activity with a conventional in vitro kinase assay using the SAMS peptide substrate. AICAR and buffer (B) were used as positive and negative controls for these studies. Results are shown in FIG. 46. The data demonstrate that Y122S/I125E effectively stimulates AMPK activity within 5 minutes of treatment even at the lowest concentration (5 μg/mL) tested.

EXAMPLE 33

Time Course and Dose Response of gAd Y122S/I125E-Induced Palmitate Oxidation in L6 Myotubes gAd Y122S/I125E treatment of differentiated rat L6 myotubes increases fatty acid oxidation. Rat L6 cells were induced to differentiate during a four day culture. Rat L6 myotubes were treated with either a time course (5, 15, 30, or 60 minutes) of 5 μg/mL Y122S/I125E or a dose response (5, 10, or 50 μg/mL) of gAd Y122S/I125E; and measured for palmitate oxidation using a conventional fatty acid oxidation assay. AICAR and buffer (B) were used as positive and negative controls for these studies. Results are shown in FIG. 47. The data demonstrate that Y122S/I125E effectively stimulates fatty acid oxidation within 5 minutes of treatment even at the lowest concentration (5 μg/mL) tested.

EXAMPLE 34 gAd Y122S/I125E Stimulated Glucose Uptake in L6 Myotubes gAd Y122S/I125E treatment of differentiated rat L6 myotubes increases glucose uptake. Rat L6 cells were induced to differentiate during a four day culture. Rat L6 myotubes were untreated or treated insulin or 10 and 50 μg/mL Y122S/I125E for 30 minutes (FIG. 48, gray bars) or two hours (FIG. 48, checkered bars). Glucose uptake was measured as described in Example 29 except that AraA was not included in these experiments. A 30 minute treatment of 10 μg/mL Y122S/I125E induced a 1.4-fold increase in glucose uptake relative to the control.

EXAMPLE 35

Pharmacokinetic Study of gAd Y122S/I125E in Female C57BL/6 Mice gAd Y122S/I125E was formulated in PBS and delivered to female C57BL/6 mice at 1 and 6 mg/kg dose levels via IP, SC, and IV routes. Serum was collected over multiple time points and the serum gAd levels were determined by standard ELISA methods. The ELISA was confirmed to be specific for human gAd and not cross-react against endogenous mouse adiponectin. FIGS. 49 and 50 show the representative serum gAd versus time plots for the two dose levels. The serum gAd levels were subjected to noncompartmental pharmacokinetic analysis using WinNonlin. FIG. 51 shows a table of derived PK parameters.

EXAMPLE 36 gAd Y122S/I125E Efficacy in Male db/db Mice gAd Y122S/I125E efficacy was evaluated in a monogenic mouse model of type 2 diabetes. Male db/db mice were treated with 0.1 or 0.3 mg/kg Y122S/I125E and 10 mg/kg Rosiglitazone was used as a positive control. C57BL/6 mice were treated with vehicle as non-diseased control group. All administrations were given daily SC injection for a 19 day treatment period. Mice were measured for fed state glucose levels (using hand-held glucometer) and weight gain throughout the duration of treatment. FIGS. 52 and 53 show the results of the in-life measurements, fed state glucose levels and weight gain, respectively. The mice were subjected to glucose tolerance tests at prior to and at the conclusion of treatment (FIGS. 54A and 54B). The 0.3 mg/kg Y122S/I125E treatment group had improved fed state glucose levels relative to the 0.1 mg/kg group, gained less weight than the Rosiglitazone group, and had improved glucose clearance in the glucose tolerance test.

EXAMPLE 37

Effect of gAd Y122S/I125E on Phosphorylation of AMPK, ACC and NOS in Arota and Myocardium Cells Male C57BL/6 mice were given a single intraperitoneal injection of gAd Y122S/I125E at a dose level of 5 mg/kg. Saline was used as a control. Mice were sacrificed at 2, 4, 8, 12, and 24 hour after Y122S/I125E administration. Aorta and myocardium were harvested and processed for SDS-PAGE and western blot analysis using anti-phosphorylation site specific antibodies to AMPK, ACC, and NOS. Phosphorylated ACC and NOS were detected as early as 4 hours after drug administration and remained phosphorylated through the 24 hour time point. Results are shown in FIG. 55.

While the foregoing has been described in considerable detail and in terms of preferred embodiments, these are not to be construed as limitations on the disclosure or claims to follow. Modifications and changes that are within the purview of those skilled in the art are intended to fall within the scope of the invention.

What is claimed is:

1. A composition comprising an adiponectin variant comprising amino acids 110-244 of human adiponectin as set forth in SEQ ID NO: 1 with the exception of mutations Y122S and I125E, at a concentration of at least 2.0 mg/mL, and a pharmaceutically acceptable carrier, wherein less than 20% of said adiponectin variant becomes insoluble after storage at 4° C. for one week in 10 mM $PO_4$, 150 mM NaCl buffer.

2. The composition comprising an adiponectin variant of claim 1, wherein said concentration is at least 5.0 mg/mL.

3. The composition comprising an adiponectin variant of claim 1, wherein said concentration is at least 10 mg/mL.

4. The composition comprising an adiponectin variant of claim 1, wherein said concentration is at least 20 mg/mL.

5. The composition comprising an adiponectin variant of claim 1, wherein said concentration is at least 30 mg/mL.

6. The composition comprising an adiponectin variant of claim 1, wherein said concentration is at least 50 mg/mL.

7. The composition comprising an adiponectin variant of claim 6, wherein less than 5% of said adiponectin variant becomes insoluble after storage at 4° C. for one week in 10 mM $PO_4$, 150 mM NaCl buffer.

8. The composition comprising an adiponectin variant of claim 1, wherein said concentration is at least 60 mg/mL.

* * * * *